(12) United States Patent
Marchant et al.

(10) Patent No.: US 10,426,772 B2
(45) Date of Patent: Oct. 1, 2019

(54) USE OF ERGOT ALKALOIDS AS AN ANTHELMINTIC AGENT

(71) Applicant: Regents of the University of Minnesota, Minneapolis, MN (US)

(72) Inventors: Jonathan Stephen Marchant, St Paul, MN (US); John David Chan, St Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/596,776

(22) Filed: May 16, 2017

(65) Prior Publication Data
US 2018/0021334 A1    Jan. 25, 2018

Related U.S. Application Data

(60) Provisional application No. 62/337,088, filed on May 16, 2016.

(51) Int. Cl.
| | | |
|---|---|---|
| *A61K 31/48* | (2006.01) | |
| *A61K 31/522* | (2006.01) | |
| *A61K 31/4985* | (2006.01) | |
| *A23L 33/10* | (2016.01) | |
| *A23K 20/132* | (2016.01) | |
| *A61K 31/47* | (2006.01) | |

(52) U.S. Cl.
CPC ........ *A61K 31/4985* (2013.01); *A23K 20/132* (2016.05); *A23L 33/10* (2016.08); *A61K 31/47* (2013.01); *A61K 31/48* (2013.01); *A61K 31/522* (2013.01); *A23V 2002/00* (2013.01); *Y02A 50/423* (2018.01)

(58) Field of Classification Search
CPC .. A61K 31/48; A61K 31/522; A61K 31/4985; A23L 33/10; A23K 20/132
See application file for complete search history.

(56) References Cited

U.S. PATENT DOCUMENTS

| 8,431,155 B1 | 4/2013 | Cincotta et al. |
| 2015/0366198 A1 | 12/2015 | Meng et al. |

OTHER PUBLICATIONS

"Bromocriptine Mesylate—Generic Drug Details", [online]. © Copyright 2002-2018 think Biotech LLC. Retrieved from the Internet: <URL: https://www.drugpatentwatch.com/p/generic-api/BROMOCRIPTINE+MESYLATE>, (2018), 7 pgs.

Abdulla, Maha-Hamadien, et al., "Drug Discovery for Schistosomiasis: Hit and Lead Compounds Identified in a Library of Known Drugs by Medium-Throughput Phenotypic Screening", PLoS Negl Trop Dis 3(7): e478, (Jul. 2009), 1-14.

Akerboom, Jasper, et al., "Genetically encoded calcium indicators for multi-color neural activity imaging and combination with optogenetics", Front Mol. Neurosci., 6:(2), (2013), 1-29.

Anderson, Leticia, et al., "*Schistosoma mansoni* Egg, Adult Male and Female Comparative Gene Expression Analysis and Identification of Novel Genes by RNA-Seq", PLoS Negl Trop Dis 9(12): e0004334, (2015), 1-26.

Aragon, Anthony D., "Towards an understanding of the mechanism of action of Praziquantel", HHS Public Access, Author Manuscript, published in final edited form as: Molecular and Biochemical Parasitology, 164(1), (2009), 57-65, (Mar. 2009), 19 pgs.

Arunlakshana, O., et al., "Some quantitative uses of drug antagonists", Br. J. Pharmacol. Chemother. 14(1), (1959), 48-58.

Berriman, Matthew, et al., "The genome of the blood fluke *Schistosoma mansoni*", Nature, 460, (2009), 352-358.

Binkowski, Brock F., et al., "A Luminescent Biosensor with Increased Dynamic Range for Intracellular cAMP", ACS Chem. Biol., 6(11), (2011), 1193-1197.

Bueding, Ernest, et al., "Metabolic Requirements of Schistosomes", Journal of Parasitology, 68(2), (1982), 208-212.

Buttle, G. A. H., et al., "An Antigen in Malignant and in Embryonic Tissues", Nature, 194, (1962), p. 780.

Campos, Tulio D. L., et al., "Identification of G protein-coupled receptors in *Schistosoma haematobium* and *S. mansoni* by comparative genomics", Parasit. Vectors, 7: 242, (2014), 1-11.

Chan, John D., et al., "'Death and Axes': Unexpected $Ca^{2+}$ Entry Phenolgs Predict New Anti-schistosomal Agents", PLoS Pathogens, 10:e1003942, (2014), 1-13.

Chan, John D., et al., "A Miniaturized Screen of a Schistosoma mansoni Serotonergic G Protein-Coupled Receptor Identifies Novel Classes of Parasite-Selective Inhibitors", PLoS Pathog 12(5): e1005651., (2016), 26 pgs.

Chan, John D., et al., "$Ca^{2+}$ channels and praziquantel: A view from the free world", Parasitology International, 62(6), (2013), 619-628.

Chan, John D., et al., "Ergot Alkaloids (Re)generate New Leads as Antiparasitics", PLoS Negl. Trop. Dis., 9(9): e0004063, (2015), 1-18.

Colley, Daniel G., et al., "Human schistosomiasis", The Lancet, 383(9936), (2014), 2253-2264.

Day, T. A., et al., "Serotonin and its requirement for maintenance of contractility in muscle fibres isolated from Schistosoma mansoni", Parasitology, 108(4), (1994), 425-432.

El-Shehabi, Fouad, et al., "A Novel G Protein-Coupled Receptor of *Schistosoma mansoni* (SmGPR-3) Is Activated by Dopamine and Is Widely Expressed in the Nervous System", PLoS Negl. Trop. Dis., 6(2): e1523, (2012), 1-15.

Fan, Frank, et al., "Novel Genetically Encoded Biosensors Using Firefly Luciferase", ACS Chem. Biol., 3(6), (2008), 346-351.

Gilissen, Julie, et al., "Forskolin-free cAMP assay for Gi-coupled receptors", Biochemical Pharmacology, 98(3), (2015), 381-391.

(Continued)

*Primary Examiner* — Zohreh A Fay

(74) *Attorney, Agent, or Firm* — Schwegman Lundberg & Woessner, P.A.

(57) ABSTRACT

Methods for preventing, inhibiting or treating parasitic flatworm infection in a vertebrate are provided that include administering an effective amount of a composition comprising one or more ergot alkaloids, one or more lysergic acid amides, or one or more dimethoxyisoquinoline derivatives.

20 Claims, 31 Drawing Sheets

Specification includes a Sequence Listing.

(56) References Cited

OTHER PUBLICATIONS

Greenburg, Robert M., et al., "New approaches for understanding mechanisms of drug resistance in schistosomes", Parasitology, 140(12), (Oct. 2013), 1534-1546.
Harder, A., et al., "Praziquantel impairs the ability of exogenous serotonin to stimulate carbohydrate metabolism in intact *Schistosoma mansoni*", Parasitology Research, 73(5), (Sep. 1987), 442-445.
Hines-Kay, Jarrett, "Transcriptional analysis of Schistosoma mansoni treated with praziquantel in vitro", NIH Public Access, Author Manuscript, published in final edited form as: Molecular and Biochemical Parasitology, 186(2), (2012), 87-94, (Dec. 2012), 18 pgs.
Huang, Stanley C.-C., et al., "Fatty Acid Oxidation Is Essential for Egg Production by the Parasitic Flatworm *Schistosoma mansoni*", PLoS Pathog 8(10): e1002996, (Oct. 2012), 1-7.
Kasschau, Margaret R., et al., "Adenylate cyclase in adults and cercariae of Schistosoma mansoni", Molecular and Biochemical Parasitology, 5(2), (1982), 107-116.
Kasschau, Margaret R., et al., "Serotonin-activated adenylate cyclase during early development of Schistosoma mansoni", (Abstract Only), Nature, 296(5852), 1982,66-68, (1982), 1 pg.
Kenakin, T., "Drugs and receptors. An overview of the current state of knowledge", Drugs, 40(5), (1990), 666-687.
King, Charles H., "Utility of Repeated Praziquantel Dosing in the Treatment of Schistosomiasis in High-Risk Communities in Africa: A Systematic Review", PLoS Negl. Trop. Dis., 5(9): e1321, (2011), 1-15.
Knight, Jesica A., et al., "Pharmacological Analysis of the Novel, Rapid, and Potent Inactivation of the Human 5-Hydroxytryptamine$_7$ Receptor by Risperidone, 9-OH-Risperidone, and Other Inactivating Antagonists", Molecular Pharmacology, 75, (2009), 374-380.
Kroeze, Wesley K., et al., "PRESTO-Tango as an open-source resource for interrogation of the druggable human GPCRome", Nat. Struct. Mol. Biol., 22, (2015), 362-369.
Lovell, Peter J., et al., "A Novel, Potent, and Selective 5-HT$_7$ Antagonist: (R)-3-(2-(2-(4-Methylpiperidin-1-yl)ethyl)pyrrolidine-1-sulfonyl)phenol (SB-269970)", Journal of Medicinal Chemistry, 43, (2000), 342-345.
MacDonald, Kevin, et al., "A constitutively active G protein-coupled acetylcholine receptor regulates motility of larval *Schistosoma mansoni*", HHS Public Access, Author Manuscript, published in final edited form as: Molecular and Biochemical Parasitology, 202(1), (2015), 29-37, (2015), 22 pgs.
Mansour, Tag E., "Chemotherapy of parasitic worms: new biochemical strategies", Science, 205(4405), (1979), 462-469.
Mansour, Tag E., "Serotonin receptors in parasitic worms", (Abstract Only), Advances in Parasitology, 23, (1985), 1-36, (1985), 1 pg.
Mehlhorn, H., et al., "In vivo and in vitro Experiments on the Effects of Praziquantel on Schistosoma mansoni. A light and electron microscopic study.", Arzneimittel-Forschung, 31(I), Nr. 3a, (1981), 544-554.
Newmark, Phillip A., et al., "Not your father's planarian: a classic model enters the era of functional genomics", Nature Rev. Genetics, 3(3), (Apr. 2002), 210-219.
Ni, Y. G., et al., "Blockage of 5HT$_{2c}$ serotonin receptors by fluoxetine (Prozac)", Proc. Natl. Acad. Sci. USA, 94(5), (1997), 2036-2040.
Nichols, David E., et al., "Stereoselective pharmacological effects of lyserguc acid amides possessing chirality in amide substituent", Behavioral Brain Research, 73, (1996), 117-119.
Nogi, Taisaku, et al., "A Novel Biological Activity of Praziquantel Requiring Voltage-Operated $Ca^{2+}$ Channel β Subunits: Subversion of Flatworm Rwgenerative Polarity", PLoS Negl. Trop. Dis., 3:e464, (2009), 1-13.
Olliaro, Piero, et al., "The little we know about the pharmacokinetics and pharmacodynamics of praziquantel (racemate and R-enantiomer)", J. Antimic. Chem., 69(4), (2014), 863-870.
Overington, John P., et al., "How many drug targets are there?", Nat. Rev. Drug Discov., 5(12), (2006), 993-996.

Patocka, Nicholas, et al., "Serotonin Signaling in *Schistosoma mansoni*: A Serotonin-Activated G Protein-Coupled Receptor Controls Parasite Movement", PLoS Pathogens, 10(1): e1003878, (Jan. 2014), 1-15.
Patocka, Nicholas, et al., "The functional role of a serotonin transporter in Schistosoma mansoni elucidated through immunolocalization and RNA interference (RNAi)", (Abstract Only), Molecular and Biochemical Parasitology, 187(1) (Jan. 2013), 32-42, (2013), 1 pg.
Pax, Ralph A., et al., "*Schistosoma mansoni*: Differences in acetylcholine, dopamine, and serotonin control of circular and longitudinal parasite muscles", Experimental Parasitology, 58(3), (1984), 314-324.
Pearce, Edward J., "The metabolic control of schistosome egg production", Cellular Microbiology, 17(6), (2015), 796-801.
Pellegrino, J., et al., "Experimental Chemotherapy of Schistosomiasis Mansoni. XIII. Activity of praziquantel, an isoquinoline-Pyrazino Derivative, on Mice, Hamsters and Cebus Monkeys", Z. Parasitenkd., 52(2), (1977), 151-168.
Pellegrino, J., et al., "The Oogram method for the screeing of drugs in Schistosomiasis mansoni", American Journal of Tropical Medicine and Hygiene, 14(3), (1965), 363-369.
Protasio, Anna V., et al., "A Systematically Improved High Quality Genome and Transcriptome of the Human Blood Fluke *Schistosoma mansoni*", PLoS Negl. Trop. Dis., 6(1): e1455, (2012), 1-13.
Rahman, M. Saidur, "*Schistosoma mansoni*: Effects of in Vivo Serotonin (5-HT) on Aerobic and Anaerobic Carbohydrate Metabolism", Experimental Parasitology, 60, (1985), 10-17.
Salvador-Recatala, Vicenta, et al., "Calcium channels of schistosomes: unresolved questions and unexpected answers", Wiley Interdiscip. Rev. Membr. Transp. Signal., 1, (2012), 85-93.
Schiller, Everett L., "Aerobic and Anaerobic Carbohydrate Metabolism and Egg Production of *Schistosoma mansoni* in vitro", The Journal of Parasitology, 61(3), (Jun. 1975), 385-389.
Semeyn, David R., "Surface Electrical Activity from *Schistosoma mansoni*: A Sensitive Measure of Drug Action", Journal of Parasitology, 68(3), (1982), 353-362.
Smith, Carol, et al., "Risperidone Irreversibly Binds to and Inactivates the h5-HT$_7$ Serotonin Receptor", Molecular Pharmacology, 70(4), (2006), 1264-1270.
Smith, Carol, et al., "Risperidone-Induced Inactivation and Clozapine-Induced Reactivation of Rat Cortical Astrocyte 5-Hydroxytryptamine? Receptors: Evidence for In Situ G Protein-Coupled Receptor Homodimer Protomer Cross-Talk", Molecular Pharmacology, 79(2), (2011), 318-325.
Tomosky, Thomas K., et al., "Tryptaminergic and dopaminergic responses of Schistosoma mansoni", Journal of Pharmacology and Experimental Therapeutics, 190(2), (1974), 260-271.
Tucker, Matthew S., et al., "Unit 19.1 Schistosomiasis", NIH Public Access, Author Manuscript, published in final edited form as: Curr. Protoc. Immunol., Unit-19 1, (May 2001), 80 pgs.
Wacker, Daniel, et al., "Crystal Structure of an LSD-Bound Human Serotonin Receptor", Cell, 168, (2016), 377-389.
Wang, Jia Bei, et al., "L-Tetrahydropalamatine: A Potential New Medication for the Treatment of Cocaine Addiction", NIH Public Access, Author Manuscript, published in final edited form as: Future Med. Chem., 49(2), (2012), 177-186, (2012), 16 pgs.
Wang, Wei, et al., "Susceptibility or resistance of praziquantel in human schistosomiasis: a review", Parasitology Research, 111(5), (Oct. 2012), 1871-1877.
Willcockson, W. S., et al., "Drug effects on the 5-HT response of *Schistosoma mansoni*", Comparative Biochemistry and Physiology C: Comparative Pharmacology, 77(1), (1984), 199-203.
Witchley, Jessica N., et al., "Muscle Cells Provide Instructions for Planarian Regeneration", Cell Reports, 4(4), (2013), 633-641.
Zamanian, Mostafa, et al., "The repertoire of G protein-coupled receptors in the human parasite Schistosoma mansoni and the model organism *Schmidtea mediterranea*", BMC Genomics, 12: 596, (2011), 1-21.
Zhang, Dan, et al., "Opposing Roles of Voltage-Gated $Ca^{2+}$ Channels in Neuronal Control of Regenerative Patterning", Journal of Neuroscience, 31(44), (2011), 15983-15995.

(56) References Cited

OTHER PUBLICATIONS

Zhang, Ji-Hu, et al., "A Simple Statistical Parameter for Use in Evaluation and Validation of High Throughput Screening Assays", J. Biomol. Screen, 4(2), (1999), 67-73.

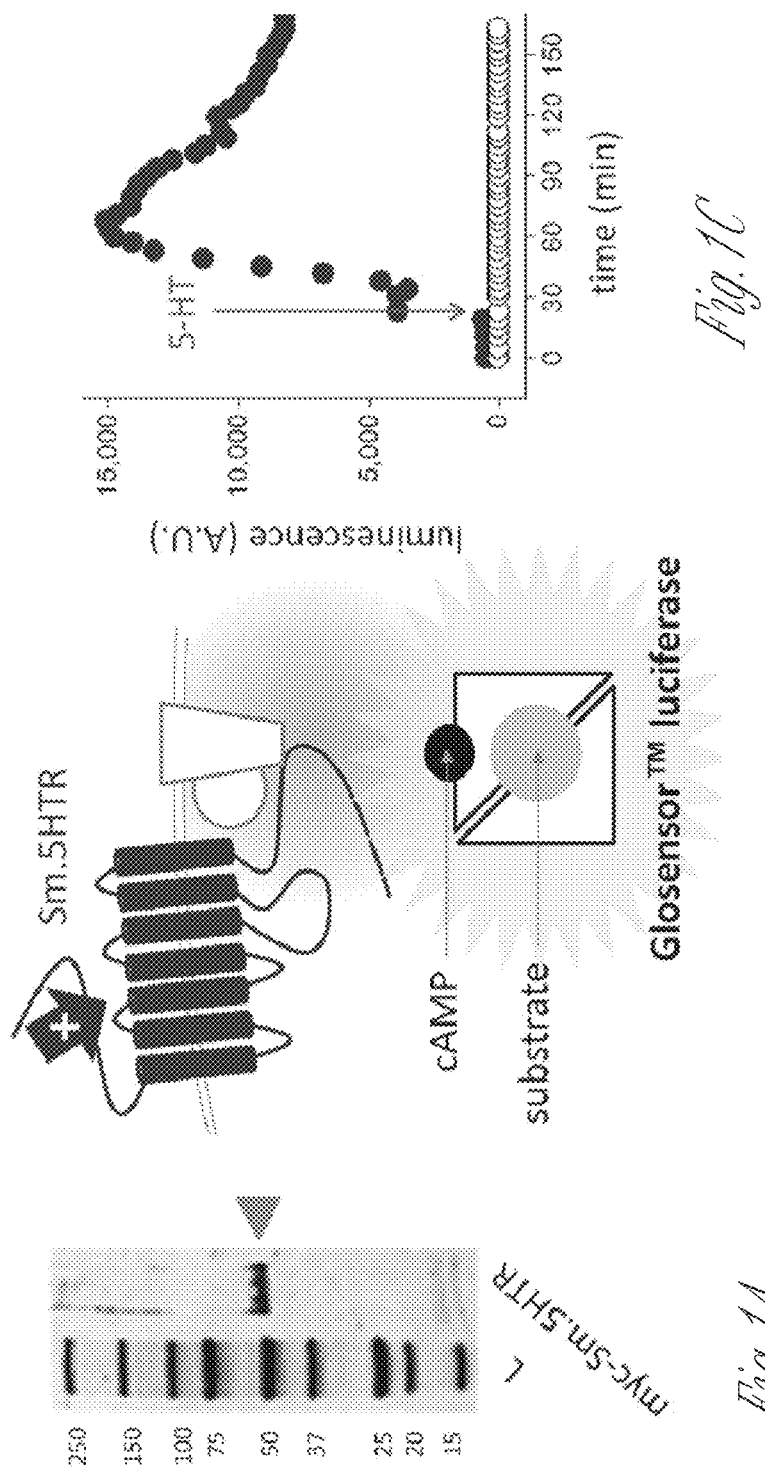

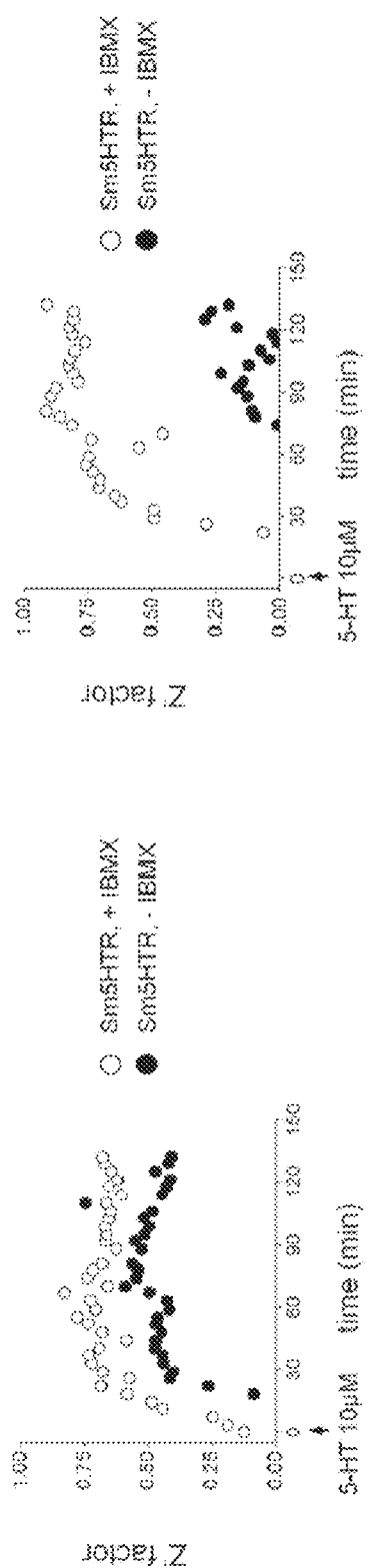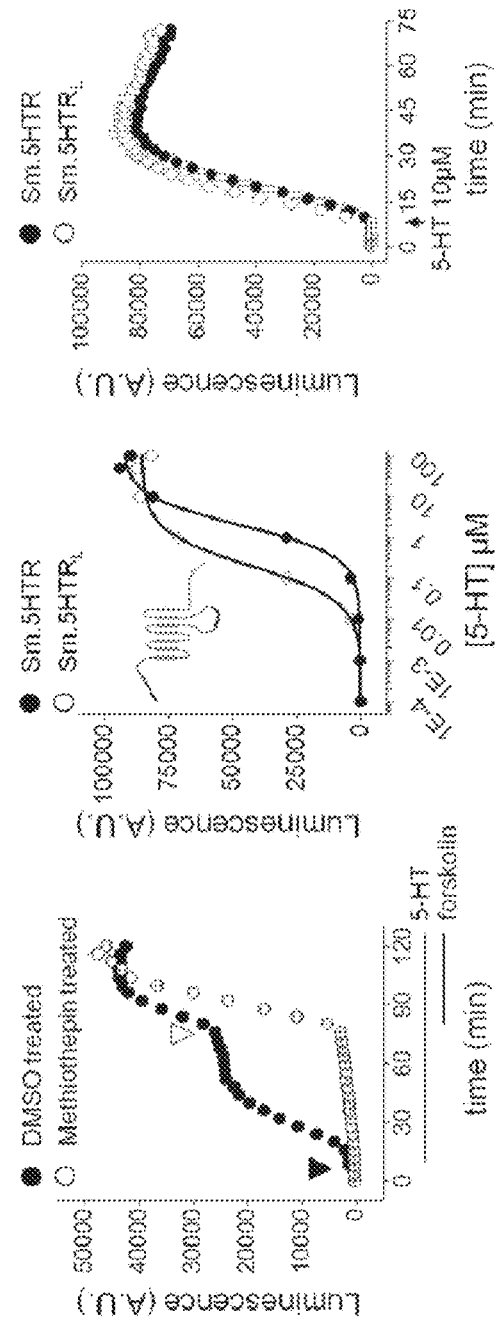

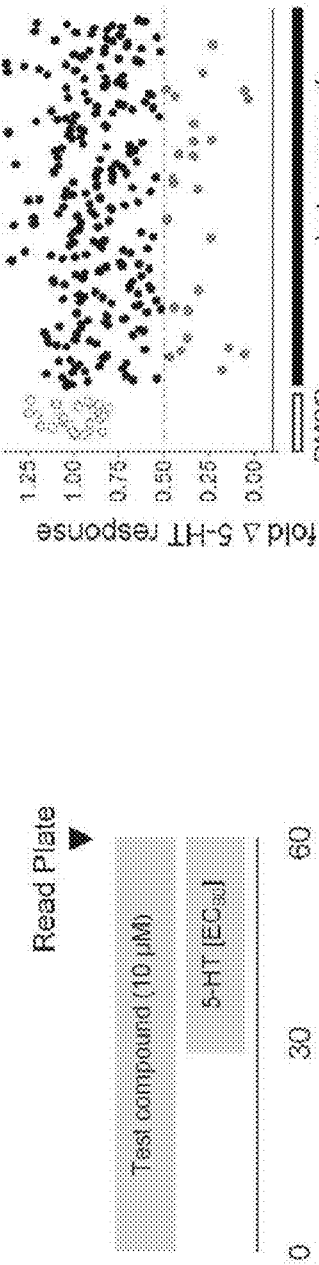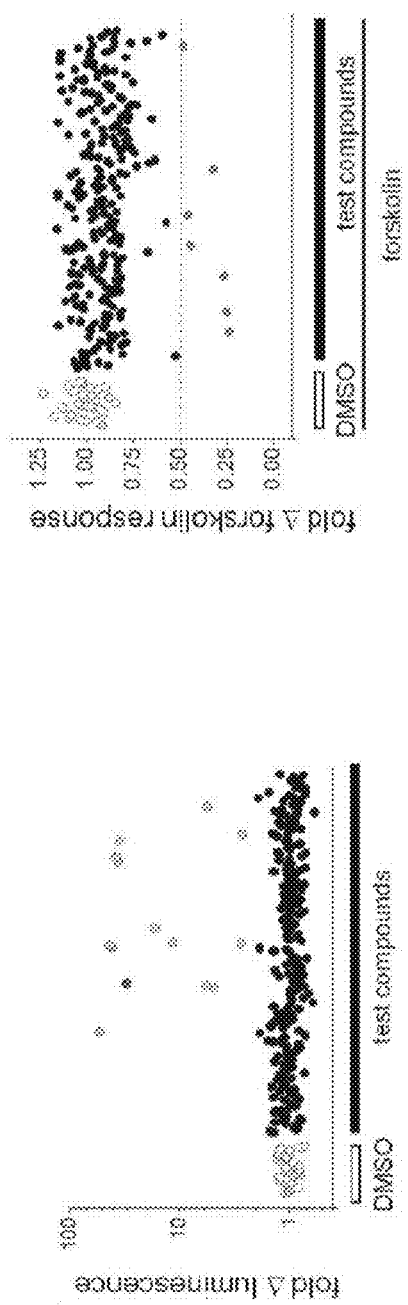

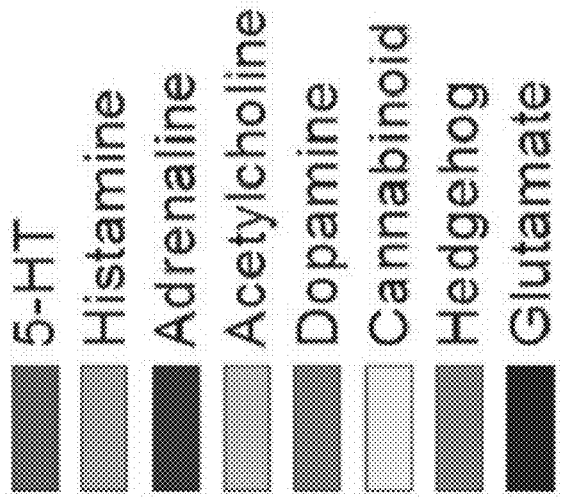
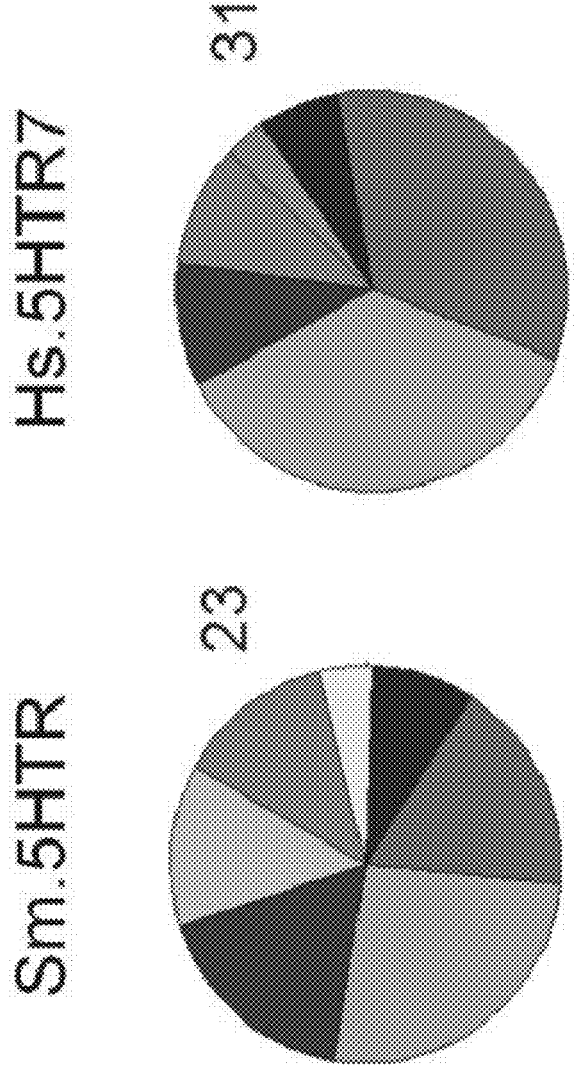
Fig. 6

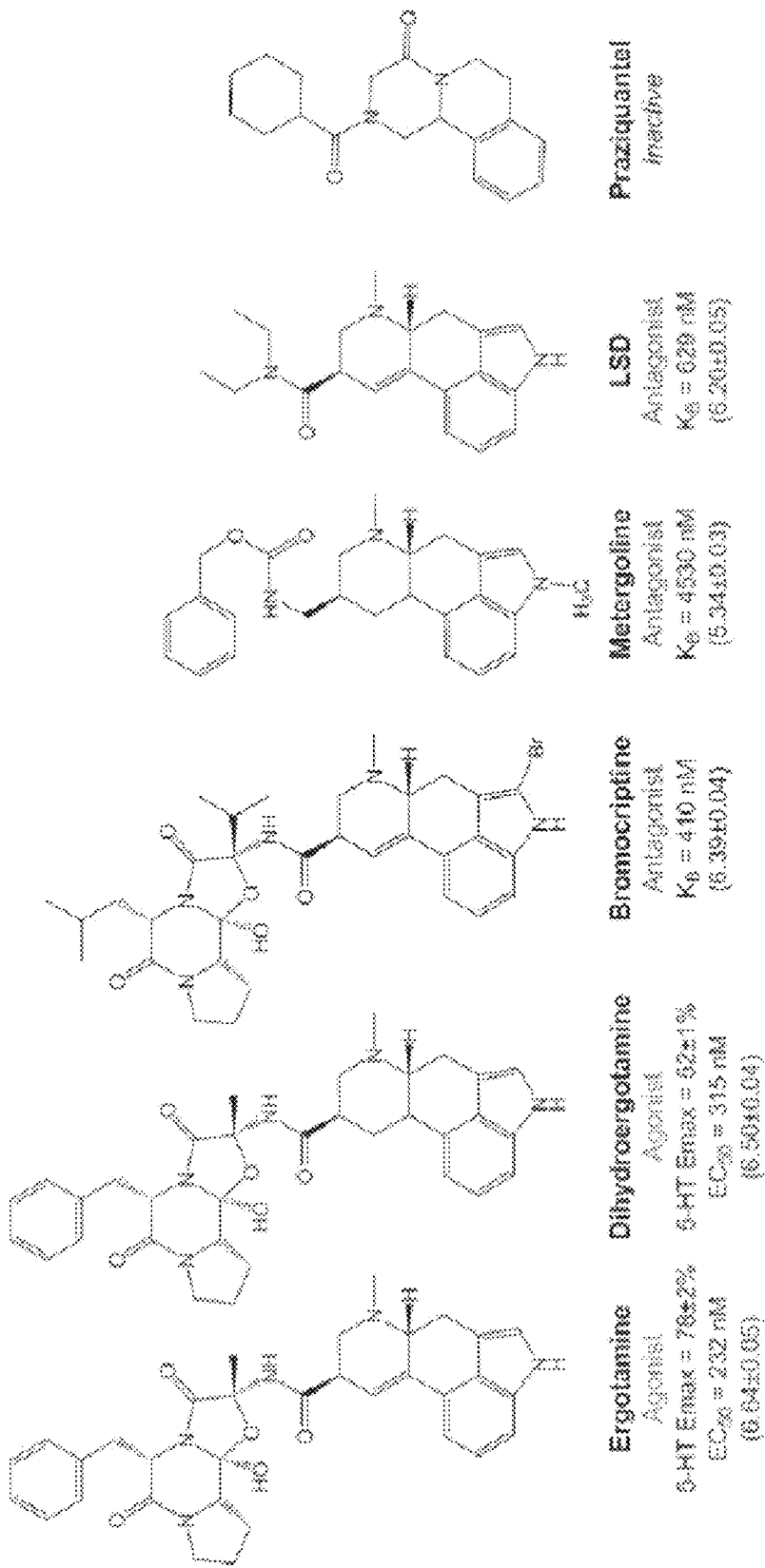

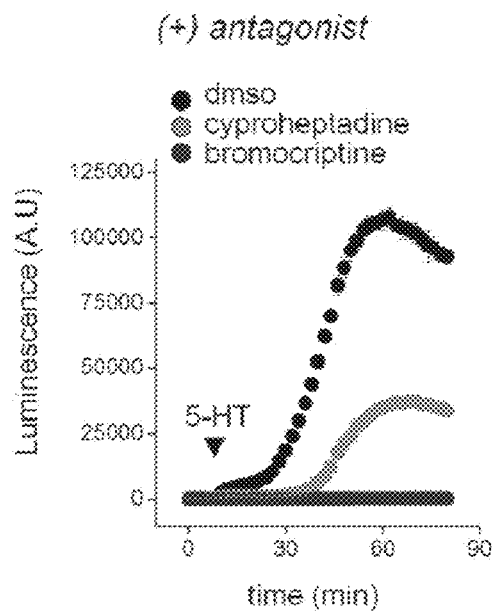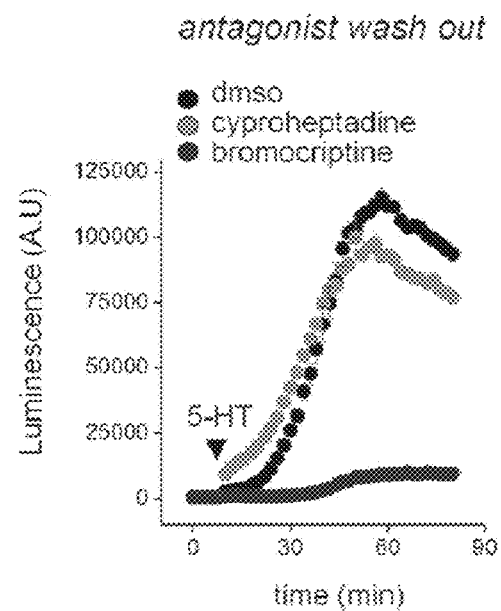
*Fig. 11A*  *Fig. 11B*
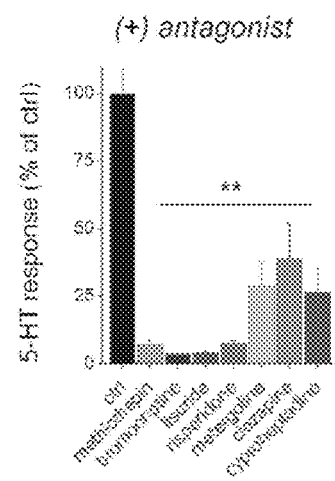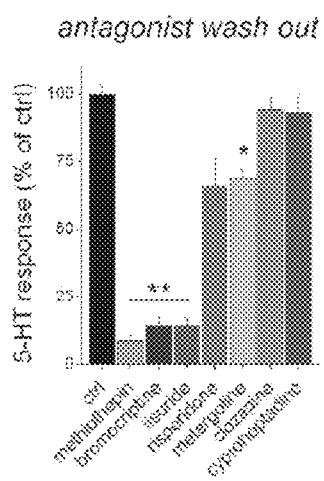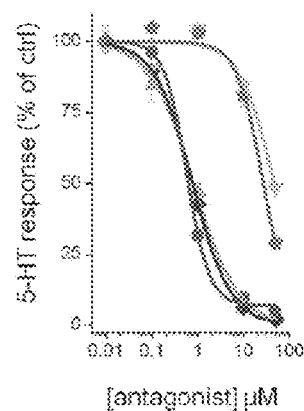
*Fig. 11C*  *Fig. 11D*  *Fig. 11E*

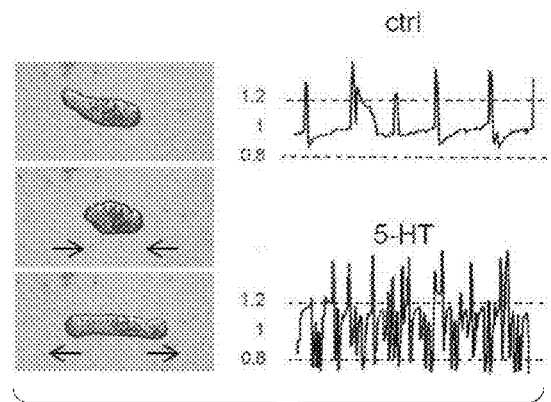 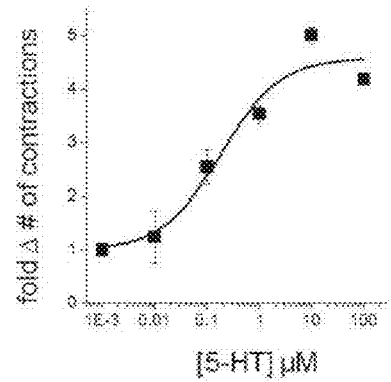
*Fig. 14A*  *Fig. 14B*
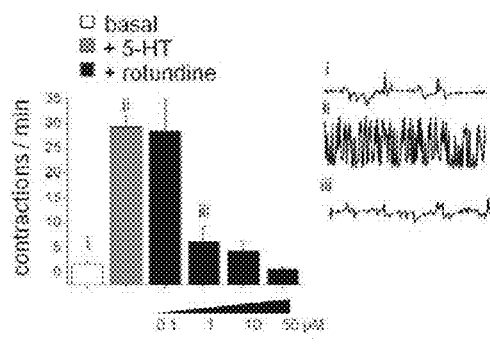 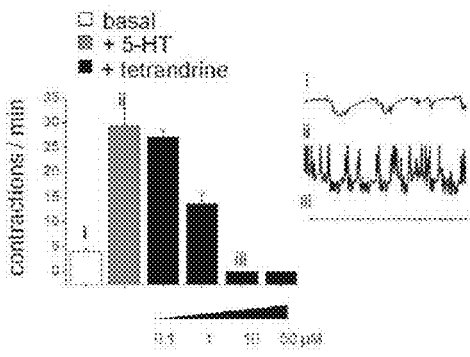
*Fig. 14C*  *Fig. 14D*
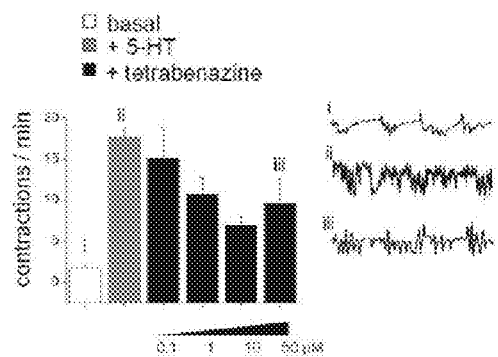 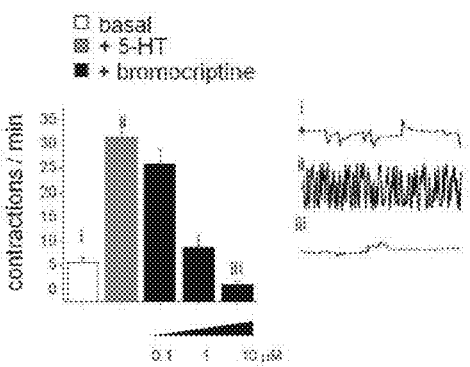
*Fig. 14E*  *Fig. 14F*

```
ATGTGGTATATTCCAACAAAACATGAACATTGGTTTAAATTATTATTCTATTATTTATTTATTTCATGTAATGGTTTA
TTGATAATTGTGAATTCTTTGGATATATCTTACTGGATAATTGAAGATACAAAAATGACAATCTCACAATTGGATAA
TTCTAGTATTAAATCAACATTATCAATGAATAAATCAAATACCTCAGAATGTATCAGTGAAAATGATTCTGTATTGA
TTACAGGGATAATTTTTATTTTATCATTAATTGTTGCAATAGCTACTGCTGGAGGAAATTTTTTAGTAATTTTAGCC
GTGATACTTGTGAAAAAACTTCAAACACCAAGTAATATTCTTATTGGAAGTTTAGCATTCAGTGATTTCTTTGTGG
CTCTATTAGTTTTACCGTTTACAATAATTGATGCATATCAAGGTTATTGGCCGTTCAATGAGGGTTTATGCGGATAT
GTATATATCTTTCGATGTATTATTGTGTACTGCATCAATACTAAATCTTTGTGCTATTTCCATTGATCGATATTTGG
TTATCACAAAACCACTGACATATGCAAGTAGACGAACACCACAACGTATGGCTGCTATGATAGCTACTGCATGGA
TAGGTTCAGCATTAATAAGTATACCACCAAATTTTGGGGTGGAAAGATCCATTTCAAAAATGTGCCTGCGAGTATA
GTAAAAATGTTGGTTATCAGGTGTATGCAACATTTTTCGCATTTTATGTACCACTTATCGTGATGATTATTCTGTAT
GGTAGGATATTTAAATTGGCTAGAGAAATGTCACGTAGTGGTCAGTCAAAAATGACAGCAGGCATATCACGTAAG
TCAACTGAAGTGCCAGAAACTGTATCTAATAATTCACATTCAGAACGGATATTAGATAAGAGTATACAGGAATTAC
AAATTACAAGTACAAATATAACTGAATATGTACAGTCAGATGATGAGCATTTAGTAACTAAAGCAATTAATAATGG
TGTGAAAAAGGATGGACATACAAATGATATCTGTAAAGCAAGAGAATATGATAAAAGATTAAACTCTTACTCATCA
AGAAAACTATTAACTGATTCTATGAATGTGACCAGTGAATTGTCCAGAGAAGCTCATGGAAGAAGATCTCGTGGG
AATTCCGATACGAAAGTAATTAAAACACTTGGAGTTATAATGGGATGTTTTTGTCTTTGCTGGCTTCCATTTTTTAT
GATACAGCTACTTTTGGCCCTTTTAAGTGCAGCTGGTTACAACACTGTGAACATGATTCCAGTTAGTGTATTTCGA
TTTTTACAATGGTTAGGTTACGTGAACAGTTTTCTCAATCCACTTATATATGCCAAATTCGATCGTGAATTCGTG
GTCCTTTTAAAATGATACTTCTGTGTCACTGTCGTAATATTAATGCACGATTACGTGCAGTTCACTATTCTGCTCA
ATACGGTCTACCAAGTTCATCAAGTAAGCGTCAAAGCATTGTTGTATCTTCACCTTATACACGTAATGATACAGCT
TCAAGATGGTTAGGGAAGTCTGTAAATCAAAGATGTACAAGTGCCGTACCTATACGGCCACGTCGAAGACCTCA
AATGAATTTCAGAAACGCTATTTCAGGTCAAACGGATGAAAGATGA (SEQ ID NO:1)
```

*Fig. 17A*

```
MWYIPTKHEHWFKLLFYYLFISCNGLLIIVNSLDISYWIIEDTKMTISQLDNSSIKSTLSMNKSNTSECISENDS
VLITGIIFILSLIVAIATAGGNFLVILAVILVKKLQTPSNILIGSLAFSDFFVALLVLPFTIIDAYQGYWPFNEGLCD
MYISFDVLLCTASILNLCAISIDRYLVITKPLTYASRRTPQRMAAMIATAWIGSALISIPPNFGWKDPFQKCACE
YSKNVGYQVYATFFAFYLPLIVMIILYGRIFKLAREMSRSGQSKMTAGISRKSTEVPETVSNNSHSEPILDKSI
QELQITSTNITEYVQSDDEHLVTKAINNGVKKDGDTNDICKAREYDKRLNSYSSRKLLTDSMNVTSELSREA
HGRRSRGNSDTKVIKTLGVIMGCFCLCWLPFFMIQLLLALLSAAGYNTVNMIPVSVFRFLQWLGYVNSFLNP
LIYAKFDREFRGPFKMILLCHCRNINARLRAVHYSAQYGLPSSSSKRQSIVVSSPYTRNDTASRWLGKSVN
QRCTSAVPIRPRRRPQMNFRNAISGQTDER (SEQ ID NO:2)
```

*Fig. 17B*

\>Schistosoma_mansoni_5HTR
MWYIPTKHEHWFKLLFYYLFISCNGLLIIVNSLDISYWIIEDTKMTISQLDNSSIKSTLS
MNKGNTSECISENDSVLITGIIFILSLIVAIATAGGNFLVILAVILVKKLQTPSNILIGS
LAFSDFFVALLVLPFTIIDAYQGYWPFNEGLCDMYISFDVLLCTASILNLCAISIDRYLV
ITKPLTYASRRTPQRMAAMIATAWIGSALISIPPNFGWKDPFQKCACEYSKNVGYQVYAT
FFAFYLPLIVMIILYGRIFKLAREMSRSGQSKMTAGISRKSTEVPETVSNNSHSEPILDK
SIQELQITSTNITEYVQSDDEHIVTKAINNGVKKDGDTNDICKAREYDKRLNSYSSRKLL
TDSMNVTSELSREAHGRRSRGNSDTKVIKTLGVIMGCFCLCWLPFFMIQLLLALLSAAGY
NTVNMIPVSVFRFLQWLGYVNSFLNPLIYAKFDREFRGPFKMILLCHCRNINARLRAVHY
SAQYGLPSSSSKRQSIVVSPYTRNDTASRWLGKSVNQRCTSAVPIRFRRRPQMNFRNAI
SGQTDER- (SEQ ID NO:3)

*Fig. 17C*

\>Schistosoma_haematobium_5HTR
MWYILTKHEHRFKLLIHLFTSYNGLFTNVNSLNTSYWIIDNTNMTISQQNNSSIKSTLS
INNLNTSECISENDSALITGIIFILSLIVAIATAGGNFLVILAVILVKKLQTPSNILIGS
LAFSDFFVALLVLPFTIIDAYQGYWPFNEGLCDMYISFDVLLCTASILNLCAISIDRYLV
ITKPLTYASRRTPQRMAAMIATAWIGSALISIPFNFGWKEPFQKCACEYSKNVGYQVYAT
FFAFYLPLIVMIILYGRIFKLAREMSRSGQSKMTPCTSCKSTEVPETISNNSHSEPILDK
NIQELQITSINIVEYVQSDDEHIVTNAINNGVKKDGGTNDICEAIENDKRLNSYSSRKLL
TDSMNLTNELSREAHGRRSRGNSDTKVIKTLGVIMGCFCLCWLPFFMIQLLLALLSAAGY
NTANMIPVSVFRFLQWLGYVNSFLNPLIYAKFDREFRGPFKMILLCHCRNINARLRAVHY
SAQYGLPSSSSKRQSIVVPSLYTRNDMASRCLGQSVNQRCSSAVPIRPRRRPQMNFRNAI
SGRTDER- (SEQ ID NO:4)

*Fig. 17D*

\> Schistosoma_japonicum_5HTR
MKYIPLSYKHSFKSLLIYLFFVYNTLFTIVNALNVPDWIVEERD
LTAPQLTISNNESILSVNNSSNIECISENTSASVTGIIFILSLIAAIATAGGNFLVILAV
ILVKKLQTPSNILIGSLAFSDFFVALLVLPFTIIDAYQGYWPFNEGLCDMYISFDVLLCT
ASILNLCAISIDRYLVITKPLTYASRRTPQRMATMIAAAWIGSALISIPPNFGWKEPFQK
CACEYSKNVGYQVYAIFFAFYLPLIVMITLYGRIFKLAREMSRSGQSKVTPSTIRKSTGI
SENVSNNSPVLEEKLQRDLQITDTNIAEFVQLNDEHVVTIETSNGIKNEGNIKAIPELKE
KDKRLNSYSSRKLLTDSMNANNELSRDAPGRRSRSNSDTKVIRTLGVIMGCFCLCWLPFF
MTQLLLALLSAAGYNTTNIIPVSVFRFLQWLGYVNSFLNPLIYAKFDREFRGPFKMILLC
HCRNINARLRAAHYSAQYGLPSSSNKRQSIVAGSLYSRSDLASKWFGRSLNQGCTSTLPN
RPRPRPQLNFRNTISTEPDKR- (SEQ ID NO:5)

*Fig. 17E*

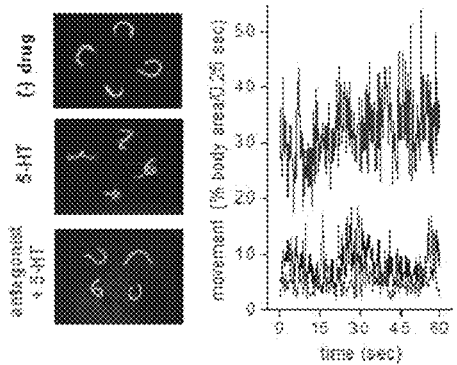
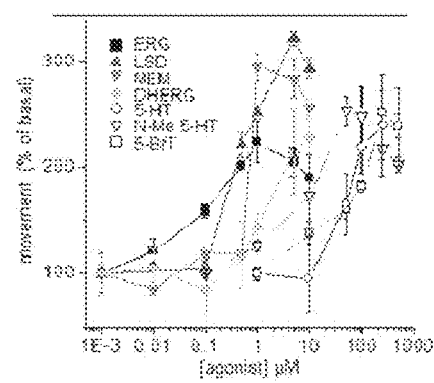
*Fig. 19A*　　　　　　　　*Fig. 19B*
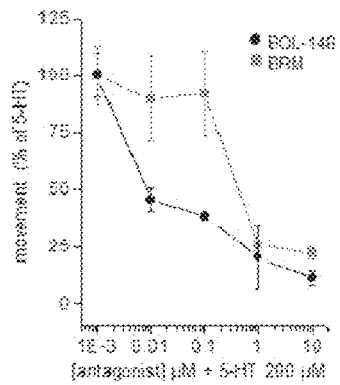
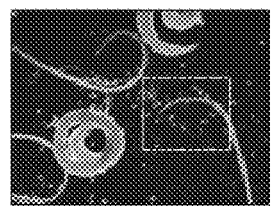
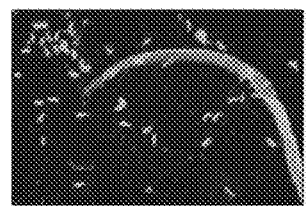
*Fig. 19D*　　　*Fig. 19E*
*Fig. 19C*
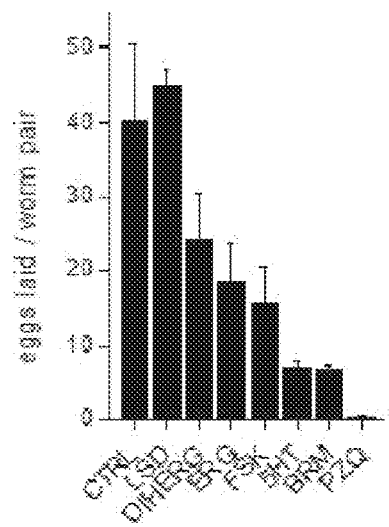
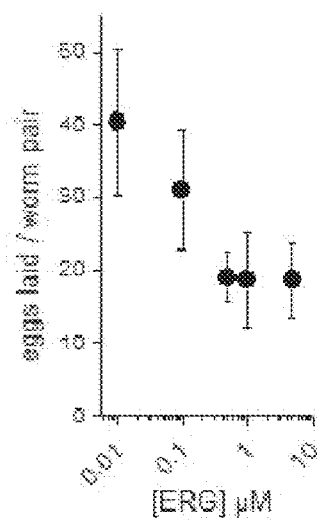
*Fig. 19F*　　　　*Fig. 19G*

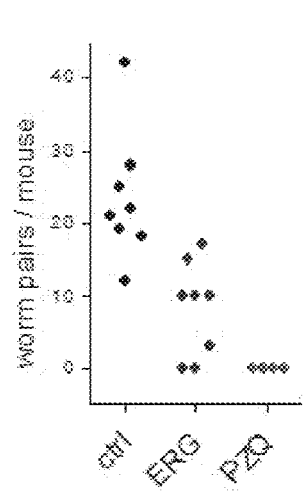
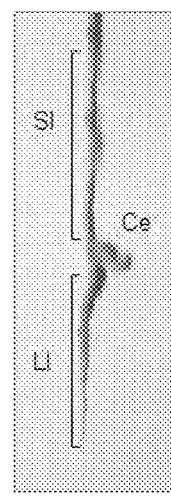
Fig. 20G                    Fig. 20H
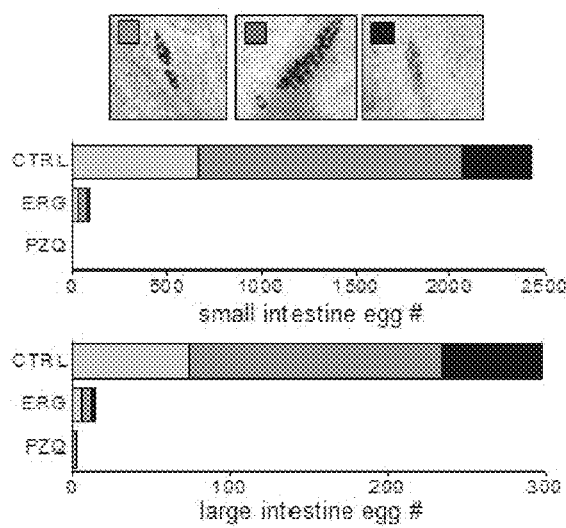
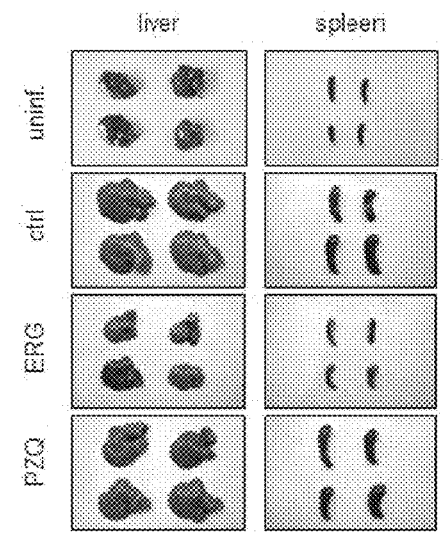
Fig. 20I                    Fig. 20J

SEQUENCE LISTING

```
<160> NUMBER OF SEQ ID NOS: 5

<210> SEQ ID NO 1
<211> LENGTH: 1644
<212> TYPE: DNA
<213> ORGANISM: Schistosoma mansoni

<400> SEQUENCE: 1
atgtggtata ttccaacaaa acatgaacat tggtttaaat tattattcta ttatttattt    60
```

| | |
|---|---|
| atttcatgta atggtttatt gataattgtg aattctttgg atatatctta ctggataatt | 120 |
| gaagatacaa aaatgacaat ctcacaattg gataattcta gtattaaatc aacattatca | 180 |
| atgaataaat caaatacctc agaatgtatc agtgaaaatg attctgtatt gattacaggg | 240 |
| ataattttta ttttatcatt aattgttgca atagctactg ctggaggaaa ttttttagta | 300 |
| attttagccg tgatacttgt gaaaaaactt caaacaccaa gtaatattct tattggaagt | 360 |
| ttagcattca gtgatttctt tgtggctcta ttagttttac cctttacaat aattgatgca | 420 |
| tatcaaggtt attggccgtt caatgagggt ttatgcgata tgtatatatc tttcgatgta | 480 |
| ttattgtgta ctgcatcaat actaaatctt tgtgctattt ccattgatcg atatttggtt | 540 |
| atcacaaaac cactgacata tgcaagtaga cgaacaccac aacgtatggc tgctatgata | 600 |
| gctactgcat ggataggttc agcattaata agtataccac caaatttcgg gtggaaagat | 660 |
| ccatttcaaa atgtgcctg cgagtatagt aaaaatgttg gttatcaggt gtatgcaaca | 720 |
| ttttcgcat tttatctacc acttatcgtg atgattattc tgtatggtag gatatttaaa | 780 |
| ttggctagag aaatgtcacg tagtggtcag tcaaaaatga cagcaggcat atcacgtaag | 840 |
| tcaactgaag tgccagaaac tgtatctaat aattcacatt cagaaccgat attagataag | 900 |
| agtatacagg aattacaaat tacaagtaca aatataactg aatatgtaca gtcagatgat | 960 |
| gagcatttag taactaaagc aattaataat ggtgtgaaaa aggatggaga tacaaatgat | 1020 |
| atctgtaaag caagagaata tgataaaaga ttaaactctt actcatcaag aaaactatta | 1080 |
| actgattcta tgaatgtgac cagtgaattg tccagagaag ctcatggaag aagatctcgt | 1140 |
| gggaattccg atacgaaagt aattaaaaca cttggagtta taatgggatg ttttttgtctt | 1200 |
| tgctggcttc cattttttat gatacagcta cttttggccc ttttaagtgc agctggttac | 1260 |
| aacactgtga acatgattcc agttagtgta tttcgatttt tacaatggtt aggttacgtg | 1320 |
| aacagttttc tcaatccact tatatatgcc aaattcgatc gtgaatttcg tggtcctttt | 1380 |
| aaaatgatac ttctgtgtca ctgtcgtaat attaatgcac gattacgtgc agttcactat | 1440 |
| tctgctcaat acggtctacc aagttcatca gtaagcgtc aaagcattgt tgtatcttca | 1500 |
| ccttatacac gtaatgatac agcttcaaga tggttaggga gtctgtaaa tcaaagatgt | 1560 |
| acaagtgccg tacctatacg gccacgtcga agacctcaaa tgaatttcag aaacgctatt | 1620 |
| tcaggtcaaa cggatgaaag atga | 1644 |

<210> SEQ ID NO 2
<211> LENGTH: 547
<212> TYPE: PRT
<213> ORGANISM: Schistosoma mansoni

<400> SEQUENCE: 2

```
Met Trp Tyr Ile Pro Thr Lys His Glu His Trp Phe Lys Leu Leu Phe
1               5                   10                  15

Tyr Tyr Leu Phe Ile Ser Cys Asn Gly Leu Leu Ile Ile Val Asn Ser
            20                  25                  30

Leu Asp Ile Ser Tyr Trp Ile Ile Glu Asp Thr Lys Met Thr Ile Ser
        35                  40                  45

Gln Leu Asp Asn Ser Ser Ile Lys Ser Thr Leu Ser Met Asn Lys Ser
    50                  55                  60

Asn Thr Ser Glu Cys Ile Ser Glu Asn Asp Ser Val Leu Ile Thr Gly
65                  70                  75                  80

Ile Ile Phe Ile Leu Ser Leu Ile Val Ala Ile Ala Thr Ala Gly Gly
                85                  90                  95
```

```
Asn Phe Leu Val Ile Leu Ala Val Ile Leu Val Lys Lys Leu Gln Thr
            100                 105                 110

Pro Ser Asn Ile Leu Ile Gly Ser Leu Ala Phe Ser Asp Phe Phe Val
            115                 120                 125

Ala Leu Leu Val Leu Pro Phe Thr Ile Ile Asp Ala Tyr Gln Gly Tyr
        130                 135                 140

Trp Pro Phe Asn Glu Gly Leu Cys Asp Met Tyr Ile Ser Phe Asp Val
145                 150                 155                 160

Leu Leu Cys Thr Ala Ser Ile Leu Asn Leu Cys Ala Ile Ser Ile Asp
                165                 170                 175

Arg Tyr Leu Val Ile Thr Lys Pro Leu Thr Tyr Ala Ser Arg Arg Thr
            180                 185                 190

Pro Gln Arg Met Ala Ala Met Ile Ala Thr Ala Trp Ile Gly Ser Ala
        195                 200                 205

Leu Ile Ser Ile Pro Pro Asn Phe Gly Trp Lys Asp Pro Phe Gln Lys
    210                 215                 220

Cys Ala Cys Glu Tyr Ser Lys Asn Val Gly Tyr Gln Val Tyr Ala Thr
225                 230                 235                 240

Phe Phe Ala Phe Tyr Leu Pro Leu Ile Val Met Ile Ile Leu Tyr Gly
                245                 250                 255

Arg Ile Phe Lys Leu Ala Arg Glu Met Ser Arg Ser Gly Gln Ser Lys
            260                 265                 270

Met Thr Ala Gly Ile Ser Arg Lys Ser Thr Glu Val Pro Glu Thr Val
        275                 280                 285

Ser Asn Asn Ser His Ser Glu Pro Ile Leu Asp Lys Ser Ile Gln Glu
    290                 295                 300

Leu Gln Ile Thr Ser Thr Asn Ile Thr Glu Tyr Val Gln Ser Asp Asp
305                 310                 315                 320

Glu His Leu Val Thr Lys Ala Ile Asn Asn Gly Val Lys Lys Asp Gly
                325                 330                 335

Asp Thr Asn Asp Ile Cys Lys Ala Arg Glu Tyr Asp Lys Arg Leu Asn
            340                 345                 350

Ser Tyr Ser Ser Arg Lys Leu Leu Thr Asp Ser Met Asn Val Thr Ser
        355                 360                 365

Glu Leu Ser Arg Glu Ala His Gly Arg Arg Ser Arg Gly Asn Ser Asp
    370                 375                 380

Thr Lys Val Ile Lys Thr Leu Gly Val Ile Met Gly Cys Phe Cys Leu
385                 390                 395                 400

Cys Trp Leu Pro Phe Phe Met Ile Gln Leu Leu Ala Leu Leu Ser
                405                 410                 415

Ala Ala Gly Tyr Asn Thr Val Asn Met Ile Pro Val Ser Val Phe Arg
        420                 425                 430

Phe Leu Gln Trp Leu Gly Tyr Val Asn Ser Phe Leu Asn Pro Leu Ile
    435                 440                 445

Tyr Ala Lys Phe Asp Arg Glu Phe Arg Gly Pro Phe Lys Met Ile Leu
    450                 455                 460

Leu Cys His Cys Arg Asn Ile Asn Ala Arg Leu Arg Ala Val His Tyr
465                 470                 475                 480

Ser Ala Gln Tyr Gly Leu Pro Ser Ser Ser Lys Arg Gln Ser Ile
                485                 490                 495

Val Val Ser Ser Pro Tyr Thr Arg Asn Asp Thr Ala Ser Arg Trp Leu
            500                 505                 510
```

```
Gly Lys Ser Val Asn Gln Arg Cys Thr Ser Ala Val Pro Ile Arg Pro
            515                 520                 525

Arg Arg Arg Pro Gln Met Asn Phe Arg Asn Ala Ile Ser Gly Gln Thr
530                 535                 540

Asp Glu Arg
545

<210> SEQ ID NO 3
<211> LENGTH: 547
<212> TYPE: PRT
<213> ORGANISM: Schistosoma mansoni

<400> SEQUENCE: 3

Met Trp Tyr Ile Pro Thr Lys His Glu His Trp Phe Lys Leu Leu Phe
1               5                   10                  15

Tyr Tyr Leu Phe Ile Ser Cys Asn Gly Leu Leu Ile Ile Val Asn Ser
            20                  25                  30

Leu Asp Ile Ser Tyr Trp Ile Ile Glu Asp Thr Lys Met Thr Ile Ser
        35                  40                  45

Gln Leu Asp Asn Ser Ser Ile Lys Ser Thr Leu Ser Met Asn Lys Ser
    50                  55                  60

Asn Thr Ser Glu Cys Ile Ser Glu Asn Asp Ser Val Leu Ile Thr Gly
65                  70                  75                  80

Ile Ile Phe Ile Leu Ser Leu Ile Val Ala Ile Ala Thr Ala Gly Gly
                85                  90                  95

Asn Phe Leu Val Ile Leu Ala Val Ile Leu Val Lys Lys Leu Gln Thr
            100                 105                 110

Pro Ser Asn Ile Leu Ile Gly Ser Leu Ala Phe Ser Asp Phe Phe Val
        115                 120                 125

Ala Leu Leu Val Leu Pro Phe Thr Ile Ile Asp Ala Tyr Gln Gly Tyr
    130                 135                 140

Trp Pro Phe Asn Glu Gly Leu Cys Asp Met Tyr Ile Ser Phe Asp Val
145                 150                 155                 160

Leu Leu Cys Thr Ala Ser Ile Leu Asn Leu Cys Ala Ile Ser Ile Asp
                165                 170                 175

Arg Tyr Leu Val Ile Thr Lys Pro Leu Thr Tyr Ala Ser Arg Arg Thr
            180                 185                 190

Pro Gln Arg Met Ala Ala Met Ile Ala Thr Ala Trp Ile Gly Ser Ala
        195                 200                 205

Leu Ile Ser Ile Pro Pro Asn Phe Gly Trp Lys Asp Pro Phe Gln Lys
    210                 215                 220

Cys Ala Cys Glu Tyr Ser Lys Asn Val Gly Tyr Gln Val Tyr Ala Thr
225                 230                 235                 240

Phe Phe Ala Phe Tyr Leu Pro Leu Ile Val Met Ile Ile Leu Tyr Gly
                245                 250                 255

Arg Ile Phe Lys Leu Ala Arg Glu Met Ser Arg Ser Gly Gln Ser Lys
            260                 265                 270

Met Thr Ala Gly Ile Ser Arg Lys Ser Thr Glu Val Pro Glu Thr Val
        275                 280                 285

Ser Asn Asn Ser His Ser Glu Pro Ile Leu Asp Lys Ser Ile Gln Glu
    290                 295                 300

Leu Gln Ile Thr Ser Thr Asn Ile Thr Glu Tyr Val Gln Ser Asp Asp
305                 310                 315                 320

Glu His Leu Val Thr Lys Ala Ile Asn Asn Gly Val Lys Lys Asp Gly
                325                 330                 335
```

```
Asp Thr Asn Asp Ile Cys Lys Ala Arg Glu Tyr Asp Lys Arg Leu Asn
            340                 345                 350

Ser Tyr Ser Ser Arg Lys Leu Leu Thr Asp Ser Met Asn Val Thr Ser
            355                 360                 365

Glu Leu Ser Arg Glu Ala His Gly Arg Arg Ser Arg Gly Asn Ser Asp
            370                 375                 380

Thr Lys Val Ile Lys Thr Leu Gly Val Ile Met Gly Cys Phe Cys Leu
385                 390                 395                 400

Cys Trp Leu Pro Phe Phe Met Ile Gln Leu Leu Ala Leu Leu Ser
                    405                 410                 415

Ala Ala Gly Tyr Asn Thr Val Asn Met Ile Pro Val Ser Val Phe Arg
            420                 425                 430

Phe Leu Gln Trp Leu Gly Tyr Val Asn Ser Phe Leu Asn Pro Leu Ile
            435                 440                 445

Tyr Ala Lys Phe Asp Arg Glu Phe Arg Gly Pro Phe Lys Met Ile Leu
            450                 455                 460

Leu Cys His Cys Arg Asn Ile Asn Ala Arg Leu Arg Ala Val His Tyr
465                 470                 475                 480

Ser Ala Gln Tyr Gly Leu Pro Ser Ser Ser Lys Arg Gln Ser Ile
            485                 490                 495

Val Val Ser Ser Pro Tyr Thr Arg Asn Asp Thr Ala Ser Arg Trp Leu
            500                 505                 510

Gly Lys Ser Val Asn Gln Arg Cys Thr Ser Ala Val Pro Ile Arg Pro
            515                 520                 525

Arg Arg Arg Pro Gln Met Asn Phe Arg Asn Ala Ile Ser Gly Gln Thr
            530                 535                 540

Asp Glu Arg
545

<210> SEQ ID NO 4
<211> LENGTH: 547
<212> TYPE: PRT
<213> ORGANISM: Schistosoma haematobium

<400> SEQUENCE: 4

Met Trp Tyr Ile Leu Thr Lys His Glu His Arg Phe Lys Leu Leu Leu
1                   5                   10                  15

Ile His Leu Phe Ile Ser Tyr Asn Gly Leu Phe Thr Asn Val Asn Ser
            20                  25                  30

Leu Asn Ile Ser Tyr Trp Ile Ile Asp Asn Thr Asn Met Thr Ile Ser
            35                  40                  45

Gln Gln Asn Asn Ser Ser Ile Lys Ser Thr Leu Ser Ile Asn Asn Leu
            50                  55                  60

Asn Thr Ser Glu Cys Ile Ser Glu Asn Asp Ser Ala Leu Ile Thr Gly
65                  70                  75                  80

Ile Ile Phe Ile Leu Ser Leu Ile Val Ala Ile Ala Thr Ala Gly Gly
                    85                  90                  95

Asn Phe Leu Val Ile Leu Ala Val Ile Leu Val Lys Lys Leu Gln Thr
            100                 105                 110

Pro Ser Asn Ile Leu Ile Gly Ser Leu Ala Phe Ser Asp Phe Val
            115                 120                 125

Ala Leu Leu Val Leu Pro Phe Thr Ile Ile Asp Ala Tyr Gln Gly Tyr
            130                 135                 140

Trp Pro Phe Asn Glu Gly Leu Cys Asp Met Tyr Ile Ser Phe Asp Val
```

-continued

```
        145                 150                 155                 160
    Leu Leu Cys Thr Ala Ser Ile Leu Asn Leu Cys Ala Ile Ser Ile Asp
                        165                 170                 175
    Arg Tyr Leu Val Ile Thr Lys Pro Leu Thr Tyr Ala Ser Arg Arg Thr
                        180                 185                 190
    Pro Gln Arg Met Ala Ala Met Ile Ala Thr Ala Trp Ile Gly Ser Ala
                        195                 200                 205
    Leu Ile Ser Ile Pro Pro Asn Phe Gly Trp Lys Glu Pro Phe Gln Lys
                        210                 215                 220
    Cys Ala Cys Glu Tyr Ser Lys Asn Val Gly Tyr Gln Val Tyr Ala Thr
    225                 230                 235                 240
    Phe Phe Ala Phe Tyr Leu Pro Leu Ile Val Met Ile Ile Leu Tyr Gly
                        245                 250                 255
    Arg Ile Phe Lys Leu Ala Arg Glu Met Ser Arg Ser Gly Gln Ser Lys
                        260                 265                 270
    Met Thr Pro Gly Thr Ser Cys Lys Ser Thr Glu Val Pro Glu Thr Ile
                        275                 280                 285
    Ser Asn Asn Ser His Ser Glu Pro Ile Leu Asp Lys Asn Ile Gln Glu
                        290                 295                 300
    Leu Gln Ile Thr Ser Thr Asn Ile Val Glu Tyr Val Gln Ser Asp Asp
    305                 310                 315                 320
    Glu His Ile Val Thr Asn Ala Ile Asn Asn Gly Val Lys Lys Asp Gly
                        325                 330                 335
    Gly Thr Asn Asp Ile Cys Glu Ala Ile Glu Asn Asp Lys Arg Leu Asn
                        340                 345                 350
    Ser Tyr Ser Ser Arg Lys Leu Leu Thr Asp Ser Met Asn Leu Thr Asn
                        355                 360                 365
    Glu Leu Ser Arg Glu Ala His Gly Arg Arg Ser Arg Gly Asn Ser Asp
                        370                 375                 380
    Thr Lys Val Ile Lys Thr Leu Gly Val Ile Met Gly Cys Phe Cys Leu
    385                 390                 395                 400
    Cys Trp Leu Pro Phe Phe Met Ile Gln Leu Leu Ala Leu Leu Ser
                        405                 410                 415
    Ala Ala Gly Tyr Asn Thr Ala Asn Met Ile Pro Val Ser Val Phe Arg
                        420                 425                 430
    Phe Leu Gln Trp Leu Gly Tyr Val Asn Ser Phe Leu Asn Pro Leu Ile
                        435                 440                 445
    Tyr Ala Lys Phe Asp Arg Glu Phe Arg Gly Pro Phe Lys Met Ile Leu
    450                 455                 460
    Leu Cys His Cys Arg Asn Ile Asn Ala Arg Leu Arg Ala Val His Tyr
    465                 470                 475                 480
    Ser Ala Gln Tyr Gly Leu Pro Ser Ser Ser Lys Arg Gln Ser Ile
                        485                 490                 495
    Val Val Pro Ser Leu Tyr Thr Arg Asn Asp Met Ala Ser Arg Cys Leu
                        500                 505                 510
    Gly Gln Ser Val Asn Gln Arg Cys Ser Ser Ala Val Pro Ile Arg Pro
                        515                 520                 525
    Arg Arg Arg Pro Gln Met Asn Phe Arg Asn Ala Ile Ser Gly Arg Thr
    530                 535                 540
    Asp Glu Arg
    545

<210> SEQ ID NO 5
```

<211> LENGTH: 545
<212> TYPE: PRT
<213> ORGANISM: Schistosoma japonicum

<400> SEQUENCE: 5

```
Met Lys Tyr Ile Pro Leu Ser Tyr Lys His Ser Phe Lys Ser Leu Leu
1               5                   10                  15

Ile Tyr Leu Phe Phe Val Tyr Asn Thr Leu Phe Thr Ile Val Asn Ala
            20                  25                  30

Leu Asn Val Pro Asp Trp Ile Val Glu Glu Arg Asp Leu Thr Ala Pro
        35                  40                  45

Gln Leu Thr Ile Ser Asn Asn Glu Ser Ile Leu Ser Val Asn Asn Ser
    50                  55                  60

Ser Asn Ile Glu Cys Ile Ser Glu Asn Thr Ser Ala Ser Val Thr Gly
65                  70                  75                  80

Ile Ile Phe Ile Leu Ser Leu Ile Ala Ala Ile Ala Thr Ala Gly Gly
                85                  90                  95

Asn Phe Leu Val Ile Leu Ala Val Ile Leu Val Lys Lys Leu Gln Thr
            100                 105                 110

Pro Ser Asn Ile Leu Ile Gly Ser Leu Ala Phe Ser Asp Phe Phe Val
        115                 120                 125

Ala Leu Leu Val Leu Pro Phe Thr Ile Ile Asp Ala Tyr Gln Gly Tyr
    130                 135                 140

Trp Pro Phe Asn Glu Gly Leu Cys Asp Met Tyr Ile Ser Phe Asp Val
145                 150                 155                 160

Leu Leu Cys Thr Ala Ser Ile Leu Asn Leu Cys Ala Ile Ser Ile Asp
                165                 170                 175

Arg Tyr Leu Val Ile Thr Lys Pro Leu Thr Tyr Ala Ser Arg Arg Thr
            180                 185                 190

Pro Cys Arg Met Ala Thr Met Ile Ala Ala Ala Trp Ile Gly Ser Ala
        195                 200                 205

Leu Ile Ser Ile Pro Pro Asn Phe Gly Trp Lys Glu Pro Phe Gln Lys
    210                 215                 220

Cys Ala Cys Glu Tyr Ser Lys Asn Val Gly Tyr Gln Val Tyr Ala Thr
225                 230                 235                 240

Phe Phe Ala Phe Tyr Leu Pro Leu Ile Val Met Ile Thr Leu Tyr Gly
                245                 250                 255

Arg Ile Phe Lys Leu Ala Arg Glu Met Ser Arg Ser Gly Gln Ser Lys
            260                 265                 270

Val Thr Pro Ser Thr Ile Arg Lys Ser Thr Gly Ile Ser Glu Asn Val
        275                 280                 285

Ser Asn Asn Ser Pro Val Leu Glu Glu Lys Leu Gln Arg Asp Leu Gln
    290                 295                 300

Ile Thr Asp Thr Asn Ile Ala Glu Phe Val Gln Leu Asn Asp Glu His
305                 310                 315                 320

Val Val Thr Ile Glu Thr Ser Asn Gly Ile Lys Asn Glu Gly Asn Ile
                325                 330                 335

Lys Ala Ile Pro Glu Leu Lys Gly Lys Asp Lys Arg Leu Asn Ser Tyr
            340                 345                 350

Ser Ser Arg Lys Leu Leu Thr Asp Ser Met Asn Ala Asn Asn Glu Leu
        355                 360                 365
```

-continued

```
Ser Arg Asp Ala Pro Gly Arg Arg Ser Arg Ser Asn Ser Asp Thr Lys
    370                 375                 380

Val Ile Arg Thr Leu Gly Val Ile Met Gly Cys Phe Cys Leu Cys Trp
385                 390                 395                 400

Leu Pro Phe Phe Met Thr Gln Leu Leu Leu Ala Leu Leu Ser Ala Ala
                405                 410                 415

Gly Tyr Asn Thr Thr Asn Ile Ile Pro Val Ser Val Phe Arg Phe Leu
            420                 425                 430

Gln Trp Leu Gly Tyr Val Asn Ser Phe Leu Asn Pro Leu Ile Tyr Ala
        435                 440                 445

Lys Phe Asp Arg Glu Phe Arg Gly Pro Phe Lys Met Ile Leu Leu Cys
    450                 455                 460

His Cys Arg Asn Ile Asn Ala Arg Leu Arg Ala Ala His Tyr Ser Ala
465                 470                 475                 480

Gln Tyr Gly Leu Pro Ser Ser Ser Asn Lys Arg Gln Ser Ile Val Ala
                485                 490                 495

Ser Ser Leu Tyr Ser Arg Ser Asp Leu Ala Ser Lys Trp Phe Gly Arg
            500                 505                 510

Ser Leu Asn Gln Gly Cys Thr Ser Thr Leu Pro Asn Arg Pro Arg Pro
        515                 520                 525

Arg Pro Gln Leu Asn Phe Arg Asn Thr Ile Ser Thr Glu Pro Asp Lys
    530                 535                 540

Arg
545
```

USE OF ERGOT ALKALOIDS AS AN ANTHELMINTIC AGENT

CROSS-REFERENCE TO RELATED APPLICATIONS

The present application claims the benefit of the filing date of U.S. application Ser. No. 62/337,088, filed on May 16, 2016, the disclosure of which is incorporated by reference herein.

STATEMENT OF GOVERNMENT RIGHTS

This invention was made with government support under AI125821 awarded by the National Institutes of Health. The government has certain rights in the invention.

BACKGROUND

The neglected tropical disease Schistosomiasis is the most socioeconomically devastating helminth infection, and the second most burdensome parasitic infection behind malaria, infecting over 200 million people worldwide (Colley et al., 2014). Clinical outcomes span gastrointestinal and liver pathologies, genitourinary disease, anemia, undernutrition, growth retardation and a heightened risk for comorbidities. Infection increases the risk of HIV transmission, making effective drug therapy for schistosomiasis a healthcare priority. Overall, the schistosomiasis disease burden encumbers third world economies with an annual loss of up to 70 million disability-adjusted life years. Infected individuals are treated by the drug praziquantel (PZQ), the mainstay therapeutic for disease control.

PZQ was originally developed during the 1970s, and the continued effectiveness of this agent over four decades of usage for treating a variety of parasitic infections has proven critically impactful (Colley et al., 2014). Indeed this clinical efficacy has ironically proven to be a factor that has restrained efforts to develop alternative therapies, and at the most basic level, define how PZQ works. However, several features of PZQ remain less than ideal and require improvement. First, the lack of a mechanistic understanding of how PZQ works has proved a roadblock in the rational design of new drugs. There is a need to identify new druggable targets that exploit broader vulnerabilities within PZQ-sensitive pathways (Chan et al., 2013; Salvador-Recatala and Greenberg, 2012; Aragon et al., 2009). Second, the inability to improve on PZQ by chemical derivatization of the drug. All PZQ derivatives synthesized to date are less effective than the parent compound. The need is to identify novel structural pharmacophores that impair parasite viability. Third, the inability of PZQ to kill all parasitic life cycle stages. Juvenile worms are refractory to PZQ (Greenberg, 2013; Hines-Kay et al., 2012), possibly a contributory factor driving development of drug resistance (Greenberg, 2013; Wang et al., 2012). The need is to identify new targets expressed throughout all lifecycle stages that are ideally conserved in other PZQ-sensitive parasites. Fourth, suboptimal cure rates in the field: PZQ requires multiple drug dosings to achieve maximal cure rates for schistosomiasis, a regimen which is not always executed in mass drug administration efforts (King et al., 2011; Olliaro et al., 2014). Therefore, there is clear opportunity to improve on the clinical penetrance of PZQ. These issues support efforts to identify new, druggable targets for development of next generation anthelmintics.

During regeneration of the planarian flatworm *D. japonica*—a widely used regenerative biology model (Newmark and Sanchez-Alvarado, 2002)—PZQ miscued polarity signaling to cause regeneration of bipolar ('two-headed') worms with dual, integrated organ systems (Nogi et al., 2009). This visually striking phenotype, coupled with the tractability of the planarian system to in vivo allowed the pathways engaged by PZQ in vivo to be defined (Nogi et al., 2009; Zhang et al., 2011; Chan et al., 2015; Chan et al., 2014). These studies culminated in a model where PZQ acts as an ergomimetic (Chan et al., 2015) with in vivo PZQ efficacy regulated by the opposing functionality of dopaminergic and serotonergic neurons (Nogi et al., 2009; Zhang et al., 2011; Chan et al., 2015; Chan et al., 2014), known regulators of muscular activity, the tissue where planarian polarity determinants reside (Witchley et al., 2013). The serotonergic and dopaminergic G protein coupled receptors (GPCRs) engaged by activity of these bioaminergic neurons therefore represent potential downstream PZQ effectors.

This is an important realization as flatworm G protein coupled receptors (GPCRs) are logical candidates for antischistosomal drug development efforts. Over one quarter of current therapeutics target rhodopsin-like GPCRs (Overington et al., 2006). However, barriers have been a lack of understanding of the physiology of specific GPCRs from within the broad GPCR portfolio (about 75-120 in *S. mansoni* (Campos et al., 2014; Zamanian et al., 2011; Berriman et al., 2009)) expressed by these organisms, as well as struggles optimizing functional expression of individual flatworm GPCRs in heterologous assay systems. However, several groups have now begun to define a role for specific GPCRs within the chemotherapeutically vulnerable excitable cell niche (Chan et al., 2015; Patocka et al., 2014; El-Shehabi et al., 2012; MacDonald et al., 2015), highlighting the key challenge of optimizing robust platforms for pharmacologically profiling these GPCRs in a miniaturized format compatible with high throughput screening (HTS). Prior studies have simply relied on interrogation of expressed GPCRs against handfuls of ligands selected around inferred agonist specificity.

SUMMARY

As described hereinbelow, a schistosome serotonergic GPCR (Sm.5HTR) implicated as a downstream modulator of PZQ efficacy was pharmcologically profiled, in a miniaturized screening assay compatible with high content screening. This approach employed a split luciferase based biosensor sensitive to cellular cAMP levels that resolves the proximal kinetics of GPCR modulation in intact cells. The data evidence the extent of pharmacological divergence between the schistosome receptor and the human $5-HT_7$-receptor homolog (Hs.5HT7R), and revealed new ligands and compound series selective for the parasitic GPCR. Despite these differences in ligand selectivity, conservation of an unusual antagonist-evoked inactivation mechanism for Sm.5HTR, a pharmacological phenomenon also exhibited at Hs.5HT7R (Smith et al., 2006; Knight et al., 2009), where exposure to a subset of antagonists results in a prolonged inactivation of signaling activity from the receptor was observed. This property enhances the attractiveness of Sm.5HTR as an anthelmintic drug target. Overall, these data underscore the feasibility of profiling flatworm GPCRs in a high throughput screening format competent to resolve different classes of GPCR modulators. Further, these data underscore the promise of Sm.5HTR as a chemotherapeutically vulnerable node for development of next generation anthelmintics.

The disclosure provides a method of preventing, inhibiting or treating parasitic flatworm infection in a vertebrate including a mammal or aquatic vertebrate, such as fish. The method includes administering an effective amount of a composition comprising one or more ergot alkaloids, ergopeptines or lysergic acid amides, e.g., which are agonists of a serotonergic receptor or antagonists of a serotonergic receptor or that inhibit contractility, viability, egg-laying or egg-production of the flatworm, or one or more dimethoxy-isoquinoline derivatives, or any combination thereof. In one embodiment, the composition comprises a compound of formula (I):

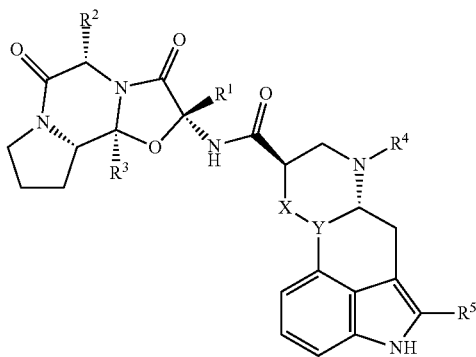

wherein, $R^1$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^2$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^3$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^4$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^5$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond;

deuterated analogs thereof, or pharmaceutically acceptable salts thereof.

In one embodiment, the composition comprises a compound of formula (II):

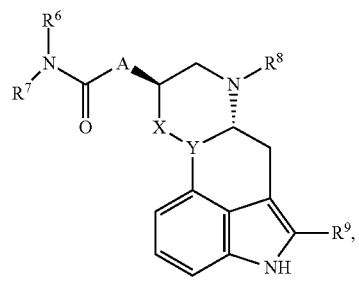

wherein, $R^6$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^7$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^8$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^9$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond;

A is a bond or $NR^x$;

deuterated analogs thereof, or pharmaceutically acceptable salts thereof.

In one embodiment, the composition comprises an agonist or partial agonist including but not limited to ergotamine, dihydroergotamine, lysergic acid methyl propyl amide (LAMPA), lysergic acid diethylamide (LSD), 6-NOR LSD, ergonovine, alpha-ergocriptine, pergolide, elymocalvine, dihydroergotoxine, or lisuride, or a combination thereof. In one embodiment, the composition does not include an ergoline. In one embodiment, the composition includes an ergoline such as pergolide but not an indole compound. In one embodiment, the composition comprises an antagonist. In one embodiment, the composition comprises an antagonist that is an ergopeptine and optionally that ergopeptine is not administered in conjunction with an indole containing compound, e.g., one having anthelminth activity. In one embodiment, the composition comprises bromocriptine, metergoline, methiothepin, risperidone, LSD, methylsergide, ergonovine, lysergic acid, lisuride, turgeride, rotundine, tetrabenazine, tetrandrine, or nicergoline, or a combination thereof. In one embodiment, the antagonist or derivative is selective for Sm.5HTR over Hs.5HTR. In one embodiment, the $IC_{50}$ selectivity ratio is less than 0.5, 0.1, 0.05, or 0.02 Sm.5HTR/Hs.5HTR (or greater than 2, 5, 10, 50 or 90 Hs.5HTR/Sm.5HTR). In one embodiment, the derivative comprises rotundine, altuzosin, tetrabenazine or tetrandrine. In one embodiment, the antagonist comprises bromocriptine, methiothepin, lisuride, risperidone or metgoline. In one embodiment, the composition is orally administered. In one embodiment, the composition is rectally administered, e.g., using a suppository. In one embodiment, the composition is administered using an inhaler. In one embodiment, the composition is a tablet. In one embodiment, the alkaloid or dimethoxyisoquinoline derivative is delivered in animal feed. In one embodiment, the mammal is a human. In one embodiment, the mammal is a livestock mammal, e.g., a bovine, porcine, caprine, or ovine. In one embodiment, livestock which are infected with tapeworm (e.g., sheep, cattle), or fish infected with flukes are treated. In one embodiment, the mammal is an equine, canine or feline. In one embodiment, the amount is effective to reduce schistosomiasis, neurocystcicerosis or clonochiasis. In one embodiment, the composition comprises an irreversible antagonist of serotonergic receptor. In one embodiment, the composition inhibits juvenile flatworm or adult flatworm growth or viability, or both. In one embodiment, the worm is Turbellaria, Trematoda, Monogenea or Cestoda (Neodermata). In one embodiment, the worm is Trematoda or Monogenea. In one embodiment, the composition is administered daily. In one embodiment, the composition is administered twice weekly. In one embodiment, the composition is administered weekly. In one embodiment, a combination of compounds, e.g., one or more ergopetines and one or more lysergic acid amides, for instance, ergotamine, dihydroergotamine and lisuride, is administered sequentially or concurrently. In one embodiment, an inhaler is employed to administer the one or more compounds.

Also provided is a method for treating a parasitic worm or helminth infection in a subject, e.g., a human. In one embodiment, the method includes administering to the subject a therapeutically effective amount of an ergot alkaloid, ergopeptine, lysergic acid amide or a dimethoxyisoquinoline derivative. In one embodiment, the parasitic worm or helminth infection is caused by a parasitic worm or helminth selected from the group consisting of Roundworm, Whipworm, Hookworm, Ascaris, Pinworm, Strongyloides, Schistosome, and Trematodes. In one embodiment, the parasitic worm or helminth infection is caused by Trematodes.

In one embodiment, a method for treating a parasitic worm or helminth infection caused by a worm or helminth resistant to praziquantel in a vertebrate is provided. The method includes administering to the vertebrate a therapeutically effective amount of an ergot alkaloid agonist or antagonist or a dimethoxyisoquinoline derivative. In one embodiment, the worm is S. masoni, S. haematoboium, S. japonicum, S. mekongi or S. intercalatum. In one embodiment, is a Trematoda. In one embodiment, the antagonist or derivative inhibits the juvenile worm. In one embodiment, the worm is Trematoda or Monogenea. In one embodiment, the worm is Turbellaria, Trematoda or Cestoda. (Neodermuta). In one embodiment, the vertebrate is a human, fish, bovine or ovine, Further provided is a method to identify compounds useful to selectively inhibit parasitic worm or helminth infection. The method includes contacting one or more compounds with Sm.5HTR and with Hs.5HTR and detecting compounds that selectively binds Sm.5HTR over Hs.5HTR. In one embodiment, the compound is an antagonist of Sm.5HTR. In one embodiment, the compound is an ergot alkaloid that is an antagonist. In one embodiment, the compound is a dimethoxy isoquinoline derivative. In one embodiment, the Sm.5HTR and Hs.5HTR are each independently expressed in cells. In one embodiment, one or more compounds and a cAMP sensitive optically detectable marker are contacted individually with recombinant Sm.5HTR and with recombinant Hs.5HTR, and a change in the optically detectable marker associated with the recombinant Sm.5HTR and with the recombinant Hs.5HTR is detected, wherein a change is indicative of inhibition. Optionally, compounds that selectively inhibit or bind the recombinant Sm.5HTR over the recombinant Hs.5HTR are identified. In one embodiment, the compound is an antagonist of one or more of Sm.5HTR, Sh.5HTR or Sj.5HTR. In one embodiment, the compound is an agonist of one or more of Sm.5HTR, Sh.5HTR or Sj.5HTR. In one embodiment, the compound is an ergot alkaloid. In one embodiment, the compound is an ergopeptine. In one embodiment, the compound is a lysergic acid amide derivative. In one embodiment, wherein the compound is a dimethoxy isoquinoline derivative. In one embodiment, the Sm.5HTR and the Hs.5HTR are recombinantly expressed in human cells. In one embodiment, the Sm.5HTR has at least 90% amino acid sequence identity to SEQ ID NO:2.

BRIEF DESCRIPTION OF THE FIGURES

FIGS. 1A-C. Functional expression of Sm.5HTR. (A) Western blot of myc-tagged Sm.5HTR (Genbank KF444051.1) in HEK293 cells. L, ladder. (B) Schematic of GloSensor™ assay depicting generation of cAMP by activation of Sm.5HTR (blue) which couples to endogenous G proteins and adenylate cyclase to increase cAMP levels. cAMP binding to the permuted luciferase construct leads to enhanced luminescence in the presence of substrate. (C) Functional expression of Sm.5HTR using this assay. In cells transfected with the biosensor (22F variant) addition of 5-HT (10 µM) caused an increase in luminescence in Sm.5HTR transfected (blue symbols), but not control cells (open symbols).

FIGS. 2A-2I. Optimization of cAMP bioluminescent sensor for monitoring Sm.5HTR activity. (A-B) Time course of cAMP changes following application of 5-HT (10 µM) HEK293 cells transfected with Sm.5HTR (circles) or untransfected controls (triangles). Assays are shown in the presence (open symbols) and absence (solid symbols) of a phosphodiesterase inhibitor (IBMX, 200 µM). Luminescence values were recorded every 3 minutes in cells transfected with the high affinity (F20, left) or low affinity (F22, right) cAMP biosensor. Inset shows data for Sm.5HTR in the absence of IBMX on a resealed y-axis. (C-D) 5-HT dose response curves from experiments such as those described in (A) for F20 (left) and F22 (right) in the presence (open) or absence (solid) of IBMX. Control data using untransfected cells are also shown (triangles). Note log scale for responses with 22F. (E-F) Z' values calculated for 5-HT evoked signals over time under the conditions described previously. (G) Real time comparison of methiothepin pretreatment on 5-HT evoked changes in cAMP. One cohort of cells was preincubated with methiothepin (10 µM, open circles), prior to addition of 5-HT (10 µM) and IBMX (200 µM, closed triangle) and then forskolin (20 µM, open triangle). (H) 5-HT dose response curves for Sm.5HTR (solid) and Sm.5HTR$_L$ (open). Inset, schematic comparison of schistosome HIT receptor isoforms. Sm.5HTR$_L$ is a longer isoform with additional sequence at the N-terminus and third intracellular loop. (I) Kinetics of 5-HT response (10 µM) for Sm.5HTR and Sm.5HTR$_L$.

FIGS. 5A-E. Pharmacological profiling of Sm.5HTR. (A) Schematic of assay workflow for screening a library of known GPCR ligands against HEK293 cells expressing either Sm.5HTR, or Hs.5HT7. Cells transfected with either 5HTR, and F22 cAMP biosensor were plated in 96-well format and exposed to test compounds (10 μM). 5-HT was added after 30 mins (at an $EC_{80}$ concentration) after which luminescence values were recorded (time=60 minutes). (B) Scatter plots summarizing effects of test compounds on the Sm.5HTR response to 5-HT (dotted line highlights threshold for defining compound 'hits'). Hits were defined at a threshold of ≥50% inhibition relative to control wells (DMSO only, open symbols). (C) Compounds were also screened against HEK293 cells expressing the F22 sensor alone (no Sm.5HTR) to screen for cAMP generation at endogenous receptors. For reference, a forskolin data point is shown in red. (D) Compounds were also screened against forskolin (20 μM) evoked changes in luminescence relative to control samples (DMSO, open circles), (E) Heat map of all test compounds screened against S. mansoni Sm.5HTR (left) and human Hs.5HT7 (middle). Each colored box represents the fold change in luminescence in response to an individual test compound (253 in total) keyed by the pseudocolor scale. Compounds showing activity against endogenous receptors in cells transfected with the 22F biosensor alone (21 compounds total) were masked (black). Right, Venn diagram summarizing selectivity of antagonist 'hits' against either Sm.5HTR, Hs.5HT7R, or both 5-HT receptors. In total, 23 ligands were classified as potential 'hits' at Sm.5HTR and 31 ligands as 'hits' at Hs.5HTR7, with 7 in common.

FIG. 6. Comparison of ligand class specificities against Sm.5HTR and Hs.5HT7R. Categorized ligand specificities of individual compounds that block Sm.5HTR and Hs.5HTR7 from classification index of the screened library. While Sm.5HTR and Hs.5HTR7 show distinct selectivity profiles to the 23 and 31 ligands identified as 'hits', the broader classification of these ligands is similar.

FIGS. 10A-F. Effects of ergot alkaloids on Sm.5HTR. (A) Dose response relationship for various bioaminergic ligands reveals ergotamine and dihydroergotamine act as partial agonists at Sm.5HTR. (B-D) Bromocriptine (B), metergoline (C) and LSD (D) act as competitive antagonists of Sm.5HTR. (E) PZQ lacks antagonist activity at Sm.5HTR. (F) Structure-activity-relationship for various ergoline ligands at the Sm.5HTR. Data in parentheses represent $pEC_{50}$±S.E.M or $pK_B$±S.E.M.

FIGS. 11A-E. Long lasting inhibition of Sm.5HT7R evoked by a subset of ligands. Sm.5HTR displays an inactivating antagonist property reported for human 5HT7R. (A) Both the 'inactivating antagonist' bromocriptine (10 μM, blue) and the competitive antagonist cyproheptadine (10 μM, grey) acutely inhibit the effect of 5-HT (10 μM) at Sm.5HTR (5-HT alone, black). (B) Sm.5HTR remains insensitive to 5-HT following washout of bromocriptine but not cyproheptadine. Cells were preincubated with antagonists as in (A) for 30 minutes, followed by solution exchange, and the assay for 5-HT responsiveness 1 hour later. (C) Inhibition of 5-HT response at Sm.5HTR by both 'inactivating antagonists' established at Hs.5HT7R (methiothepin, bromocriptine, lisuride, risperidone, metergoline) and competitive antagonists (clozapine, cyproheptadine). All drugs were tested at 10 μM for 30 minutes. , p<0.01. (D) Persistent effects of antagonists (10 μM) shown in (C) after washout and subsequent assay for 5-HT response (1 hour later). , p<0.01, *, p<0.05. (E) Titration of these 'inactivating antagonists' revealed the dose-response relationship for Sm.5HTR inhibition after washout. Colors correspond to drug identity in C&D. Data represent mean±s.e.m., n=3 (C-E).

13, desloratadine; 14, rupatadine; 15, vortioxetine; 16, amitriptyline; 17, risperidone; 18, domperidone; 19, chlorprothixene; 20, clemastine; 21, aripiprazole; 22, ketanserin; 23, ifenprodil; 24, tripelennamine; 25, fluoxetine; 26, atomoxetine; 27, orphenadrine; 28, lisuride, 29, benztropine; 30, cyclizine; 31, tetrandrine; 32, tetrabenazine; 33, berberine; 34, 6, 7-diethoxy-1, 2, 3, 4-tetrahydroisoquinoline; 35, corynoline; 36, alfuzosin, 37, rotundine; 38, fanchinoline; 39, bromocriptine; 40, metergoline; 41, LY215840; 42, nicergoline; 43, mesulergine; 44, dihydroergocristine.

FIGS. 14A-14F. Small molecule inhibitors of Sm.5HTR antagonize 5-HT stimulation of schistosomule contractility. Effects of selected ligands on schistosomules. (A) 5-HT stimulates basal contractility in S. mansoni schistosomules resolved through measurements of body length over time (1 minute recording duration). A contractile cycle is defined when a deviation of ≥20% of the average body length (dashed lines) occurs. (B) Dose-response curve for 5-HT stimulation of contractility, (C-F) Schistosomule movement was quantified for basal mobility (i, no 5-HT addition; white bars), after addition of 5-HT ((ii, 10 µM 5-HT; grey bars), and subsequent exposure to Sm.5HTR inhibitors in the presence of 5-HT (iii, indicated doses; black bars). Representative body length traces over one minute for individual schistosomules are shown for indicated conditions (right). Bar graphs represent mean±s.e.m. of independent samples, n=3. Drugs assayed represent ligands identified as Sm.5HTR antagonists in the GPCR screen (rotundine), and follow up testing of methoxyisoquinoline compounds (tetrandrine, tetrabenazine) and the ergot alkaloid bromocriptine.

FIGS. 15A-15I. Sm.5HTR inhibitors antagonize basal and 5-HT stimulated movement in adult schistosomes. (A-B) Movement of adult male (top) and female (bottom) schistosomes under basal conditions (no 5-HT) and in the presence of 5-HT (100 µM, arrow). Traces represent one minute of recorded movement for each condition. Scale, 1 cm. (C) Dose response curves showing movement of male (solid circles) and female (open circles) schistosomes exposed to increasing concentrations of 5-HT. (D-F) Left, effect of bromocriptine (10 µM) on the basal movement of adult male and female schistosomes. Representative traces showing the movement of WOMB in the absence of drug (black) and the presence of bromocriptine (red). Right, quantification of basal movement for male (solid bars) and female (open bars) worms exposed to the indicated compounds. (G-I) Left, effect of bromocriptine (10 µM) on 5-HT (100 µM) stimulated movement of adult schistosomes. Representative movement of worms exposed to 5-HT alone (black) or bromocriptine and 5-HT (red). Right, quantification of 5-HT stimulated movement for male (solid bars) and female (open bars) worms exposed to the indicated compounds. n≥3 independent experiments. * p<0.05, ** p<0.01.

Figure 16A:
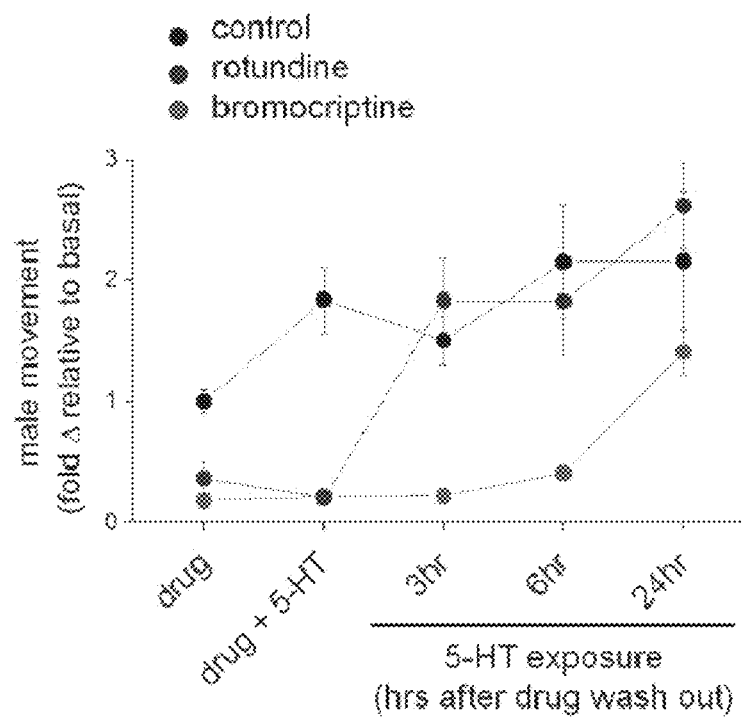
Figure 16B:
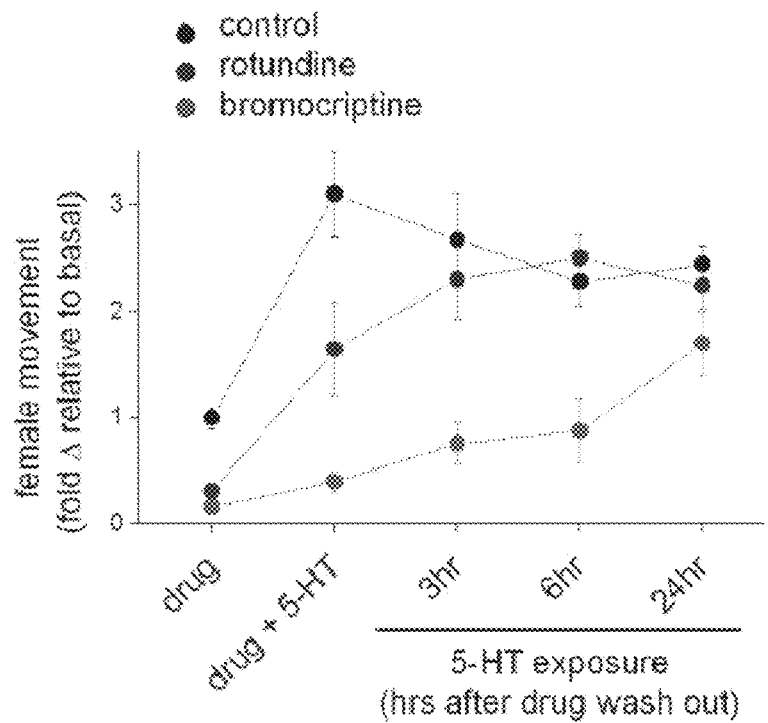

FIG. 16A-B. Long lasting inhibition of schistosome movement caused by bromocriptine.

FIGS. 17A-17E. A) Nucleotide sequence (SEC) II) NO:1) and amino acid sequence (SEQ ID NO:2) for Sm.5HTR. B) Amino acid sequences for S. mansoni, S. haematiobium and S. japonicm 5HTRs (SEQ II) Nos. 3-5).

Figure 18A:
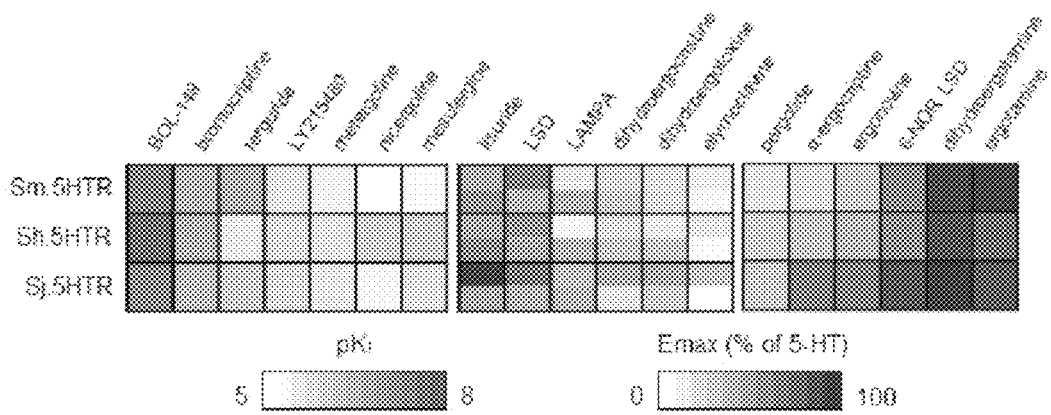
Figure 18B:
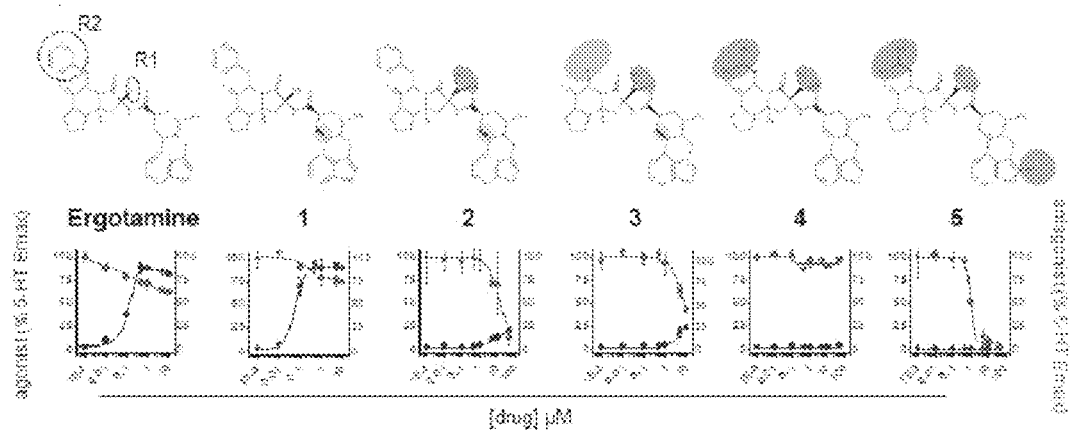
Figure 18C:
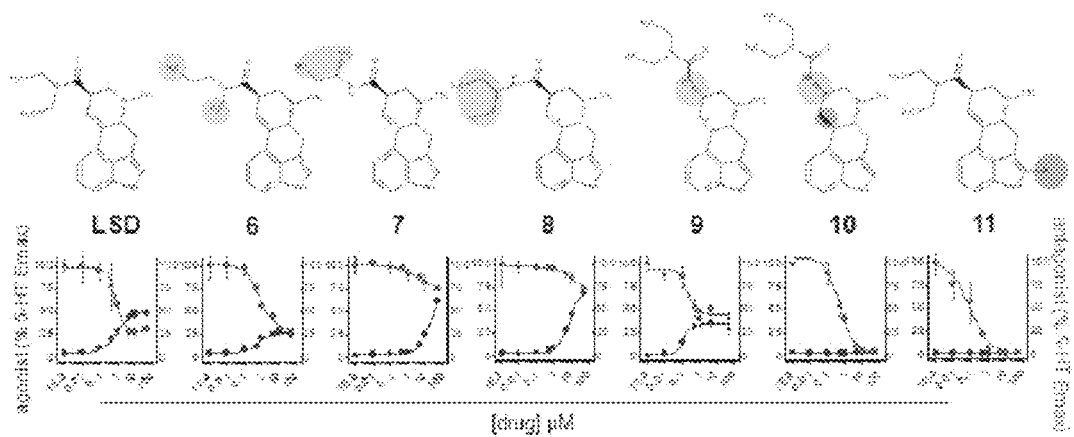

FIGS. 18A-C. Structure activity screen of ergot alkaloids. (A) Activity of various ergot alkaloids at S. mansoni, S. haematobium and S. japonicum 5HTRs. Left—compounds with antagonist activity lacking any agonism (red). Middle—partial agonists also displaying antagonist activity. Right agonists with no antagonist activity (blue). Agonist activity calibrated to maximal response of the full agonist serotonin. (B) Structure activity screen of ergopeptides. Modifications to the full agonist ergotamine that retain agonist activity are highlighted in blue, modifications that cause a loss of agonist activity are highlighted in red. 1=dihydroergotamine, 2=dihydroergocristine, 3=dihydroergotoxine, 4=α-ergocryptine, 5=bromocriptine. (C) Structure activity screen of lysergic acid amide chemical series based off of lysergic acid diethylamide (LSD) Chemical structures (top) display varying degrees of partial agonist or antagonist activity (dose response curves, bottom). Modifications to the amide group of the LSD structure that retain partial agonism are highlighted in blue, and modifications to the ergoline ring core eliminate agonist activity are highlighted in red. 6=LAMPA (lysergic acid methyl propyl amide), 7=ergometrine, 8=methylergometrine, 9=lisuride, 10=terguride, 11=BOL-148 (2-bromo-lysergic acid diethylamide).

FIGS. 19A-19I. Efficacy of alkaloid hit compounds against adult S. mansoni parasites in vitro. (A) Mobility assay in cultured adult Schistosoma mansoni. Movement of worms in vitro is stimulated by serotonin (5-HT 200 µM, blue trace) relative to basal activity (black trace). This can be blocked by treatment with a Sm.5HTR antagonist (bromocriptine 1 µM+5-HT 200 µM, red trace). (B) Sm.5HTR agonists stimulate schistosome mobility in a dose-dependent manner-solid symbols=ergot alkaloids, open symbols=tryptamines (5-HT shown in blue). (C) Sm.5HTR antagonists inhibit 5-HT (200 µM) evoked movement. (D-E) S. mansoni cultured in vitro. Dotted region with female worn) and eggs shown enlarged to the right. (F) Effect of Sm.5HTR ligands on schistosome egg production. Lysergic acid diethylamide (LSD, 10 µM), nuciferine (NUC, 10 µM), dihydroergotamine (DIHERG, 10 µM), ergotamine (ERG, 5 µM), forskolin (FSK, 100 µM), serotonin (5-HT, 100 µM), bromocriptine (BRM, 10 µM) and praziquantel (PZQ, 1 µM). (G) Dose response curve for ergotamine (ERG) inhibition of egg production. (h) Morphology of eggs laid by worms exposed to Sm.5HTR ligands. Top—eggs produced by control and ergotamine (1 µM) treated worms. Bottom—quantification of average egg size following treatment with various Sm.5HTR ligands. (I) Scatter plot of egg dimensions following drug treatment shown in G. ERG=ergotamine, LSD=lysergic acid diethylamide, MEM=methylergometrine, DHERG=dihydroergotamine, 5-HT=serotonin, N-Me 5-HT=N-methylserotonin, 5-BrT=5-bromotryptamine, BOL-148=2-bromo-lysergic acid diethylamide, BRM=bromocriptine.

FIGS. 20A-20L. Efficacy of ergot alkaloids against S. mansoni infection in vivo. (A) Schematic of the murine model of schistosomiasis used to validate anthelmintic activity of ergot alkaloids in vivo. Mice are infected with S. mansoni cerceria, which mature, mate (3-4 weeks) and initiate the egg production (6-7 weeks) which drives schistosomiasis disease pathology (liver fibrosis and splenomegaly—bottom). Blue—window of drug dosing corresponding with patent infection. (B-F) Hepatic-shift assay for acute anti-schistosomal activity of ergot alkaloids. Top: Adult schistosomes reside in the portal venous system of the infected host (left). Upon exposure to anthelmintics, parasites shift from the mesenteric veins (M) to the portal vein (PV) and liver (L). Bottom: Quantification of worm location in untreated control infections and mice treated with praziquantel (PZQ 100 mg/kg) or various Sm.5HTR ligands; ergotamine (ERG, 95 mg/kg), dihydroergotamine (DHERG, 20 mg/kg), methylergometerine (MEM, 50 mg/kg), lisuride (LIS, 10 mg/kg) and dihydroergotoxine (DHTX, 60 mg/kg), (G-L) Efficacy of ergotamine dosed over one week at ameliorating schistosomiasis infection. (uG) Worm burdens of infected mice treated with vehicle control, ergotamine (ERG, 95 mg/kg) or praziquantel (PZQ, 50 mg/kg). (H-I) Intestinal oogram quantification following drug treatment. Left—regions of intestine analyzed (SI=small intestine, Ce=cecum, LI=large intestine). Right—Mean egg counts of intestines following drug treatment (CTRL=dmso, ERG=ergotamine, PZQ=praziquantel). (J-L) Effect of drug treatment on liver and spleen enlargement resulting from patent schistosome infection. Left—representative organs harvested from uninfected mice, and mice infected and treated with dmso control, ergotamine or praziquantel. Right—mean liver and spleen weights in of each cohort. n.s.=not significant. ** p value<0.001

DETAILED DESCRIPTION

Schistosomiasis is a tropical parasitic disease afflicting about 200 million people worldwide and current therapy depends on a single drug (praziquantel) which exhibits several non-optimal features. These shortcomings underpin the need for next generation anthelmintics, but the process of validating physiologically relevant targets ('target selection') and pharmacologically profiling them is challenging. Parasitic flatworms express a diverse array of G protein coupled receptors. Remarkably, even though over a quarter of current human therapeutics target rhodopsin-like G protein coupled receptors (GPCRs), no library screen of a flatworm GPCR has yet been reported.

The priorities for a platform were: first, a robustness for miniaturization into a multiwall plate format to permit chemical library screening, and second, use of a proximal readout of receptor activity within intact cells to enable real time monitoring of GPCR activity that can resolve different types of modulators partial and inverse agonists, allosteric modulators). One technology that fulfills these requirements employs a bioluminescent cAMP reporter to monitor the activity of $G_s$ and $G_i$-coupled GPCRs, marketed as GloSensor. The assay is based upon a permutated form of firefly luciferase incorporating a cAMP-binding domain from PKA, such that cAMP-binding causes a conformational change in the enzyme that enhances the luminescent signal (Binkowski et al., 2011). The dynamic range and sensitivity of the biosensor has been shown to be compatible with a variety of HTS assays (Binkowski et al., 2011; Gilissen et al., 2015).

This approach was applied to pharmacologically profile a *S. mansoni* serotonergic GPCR (Sm.5HTR) that has been shown in vitro to respond to 5-HT through elevation of cAMP (Patocka et al., 2014). Sm.5HTR is the parasitic homologue of the planarian serotonergic GPCR (S7.1) that was recently shown to modulate the efficacy of PZQ in vivo (Chan et al., 2015). However, as with most flatworm GPCRs, little is known about the pharmacology of this receptor. An initial characterization revealed blockade of 5-HT evoked signals in the presence of high concentrations (100 µM) of mammalian bioaminergic blockers (Patocka et al., 2014).

Data evidence a divergent pharmacological signature between the parasitic serotonergic receptor and the closest human GPCR homolog (Hs.5HTR7), supporting the feasibility of optimizing parasitic selective pharmacophores. Ligands and chemical series, with potency and selectivity for Sm.5HTR over Hs.5HTR7, were identified in vitro and validated for in vivo efficacy against schistosomules and adult worms. Sm.5HTR also displayed a property resembling irreversible inactivation, a phenomenon discovered at Hs.5HTR7, which enhances the appeal of this abundantly expressed parasite GPCR as a target for anthelmintic ligand design. Bromocriptine affords an improved alternative to PZQ as it is apotent and pharmacokinetically perdurant which offers an advantage for killing parasites with a single dosage in the field. As its mechanism of action is different from PZQ, it affords an alternative to the emergence of PZQ resistant strains. PZQ-resistant schistosome sarins emerge, bromociptine would be the best therapeutic alternative available.

Exemplary Methods

In one embodiment, a method of treating parasitic flatworm or helminth infection in a vertebrate is provided. In one embodiment, the infection is treated by administering one or more doses of an ergot alkaloid, e.g., a peptide alkaloid or a lysergic acid alkaloid, or a dimethoxyisoquinoline derivative. In one embodiment, the alkaloid is an agonist including a partial agonist of a serotonergic receptor, e.g., Sm.5HTR. In one embodiment, the alkaloid is an irreversible antagonist of a serotonergic receptor, e.g., Sm.5HTR or Hs.5HTR. In one embodiment, helminths to be treated with those agents include, but are not limited to tapeworms, flukes and roundworms (nematodes). In one embodiment, the compounds are employed to treat tapeworm, *Taenia Solium, Taenia Saginates, Hymenlepis* spp., *Echinococcus granulosus* or *milticepts multiceps*, infection in a mammal or fish. In one embodiment, the agents are employed to treat fluke, e.g., *S. mansoni, S. japonicum* or *Fasciola hepatica* infection. In one embodiment, a method of treating helminth infection in a vertebrate is provided. in one embodiment, the infection is treated by administering one or more anti-helmintic doses of an ergot alkaloid, e.g., a peptide alkaloid or a lysergic acid alkaloid, or a dimethoxyisoquinoline derivative.

In one embodiment, the compounds are employed to treat roundworm, e.g., *Ascaris, Onchocerca, Rhabditis, Trichuris, Necator americanus* or *Anchylostema duodenale* infection in a vertebrate.

In one embodiment, a method of inhibiting parasitic flatworm or helminth infection in a vertebrate is provided. In one embodiment, the infection is inhibited by administering one or more doses of an ergot alkaloid, e.g., a peptide alkaloid or a lysergic acid alkaloid, or a dimethoxyisoquinoline derivative. In one embodiment, the alkaloid is an agonist of a serotonergic receptor. in one embodiment, the alkaloid is an irreversible antagonist of a serotonergic receptor, e.g., Sm.5HTR or Hs.5HTR. In one embodiment, helminths to be inhibited with those agents include, but are not limited to tapeworms, flukes and roundworms (nematodes). In one embodiment, the compounds are employed to inhibit tapeworm, e.g., *Taenia Solium, Taenia Saginates, Hymenlepis* spp., *Echinococcus granulosus* or *milticepts multiceps*, infection in a mammal or fish. In one embodiment, the agents are employed to inhibit fluke, e.g., *S. mansoni, S. japonicum* or *Fasciola hepatica* infection. In one embodiment, a method of inhibiting helminth infection in a vertebrate is provided. In one embodiment, one or more anti-helmintic doses of an ergot alkaloid, e.g., a peptide alkaloid or a lysergic acid alkaloid, or a dimethoxyisoquinoline derivative, are employed.

In one embodiment, a method of inhibiting or treating praziquantel resistant adult parasitic flatworm or helminth infection in a vertebrate is provided. In one embodiment, the infection is inhibited or treated by administering one or more doses of an ergot alkaloid, e.g., a peptide alkaloid or a lysergic acid alkaloid, or a dimethoxyisoquinoline derivative. In one embodiment, the alkaloid is an agonist of a serotonergic receptor. In one embodiment, the alkaloid is an irreversible antagonist of a serotonergic receptor, e.g., Sm.5HTR or Hs.5HTR. In one embodiment, helminths to be inhibited or treated with those agents include, but are not limited to tapeworms, flukes and roundworms (nematodes). In one embodiment, the compounds are employed to inhibit or treat tapeworm, e.g., *Taenia Solium, Taenia Saginates, Hymenlepis* spp., *Echinococcus granulosus* or *milticeps multiceps*, infection in a mammal or fish. In one embodiment, the agents are employed to inhibit fluke, e.g., *S. mansoni, S. japonicum* or *Fasciola hepatica* infection.

Exemplary Compounds for Use in the Methods

In one embodiment, parasitic worm infection in a vertebrate, e.g., a mammal such as a human, bovine, canine, feline, swine, ovine, caprine or equine, is prevented, inhibited or treated with a composition having an effective amount of a compound of formula (I):

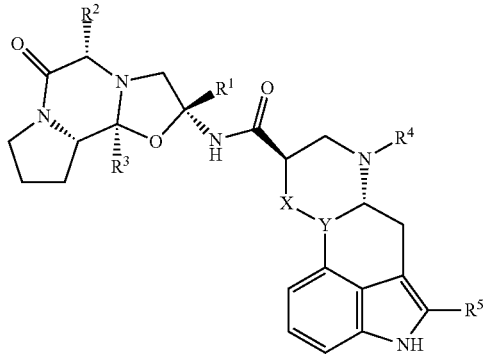

wherein, $R^1$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^2$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^3$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^4$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^5$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond; deuterated analogs thereof, or pharmaceutically acceptable salts thereof.

A composition having a compound of formula (I) may have at least 50%, 60%, 70%, 80%, 85%, 95% or more D at one or more deuterated positions.

In one embodiment, the compound of formula (I) can have the following structures:

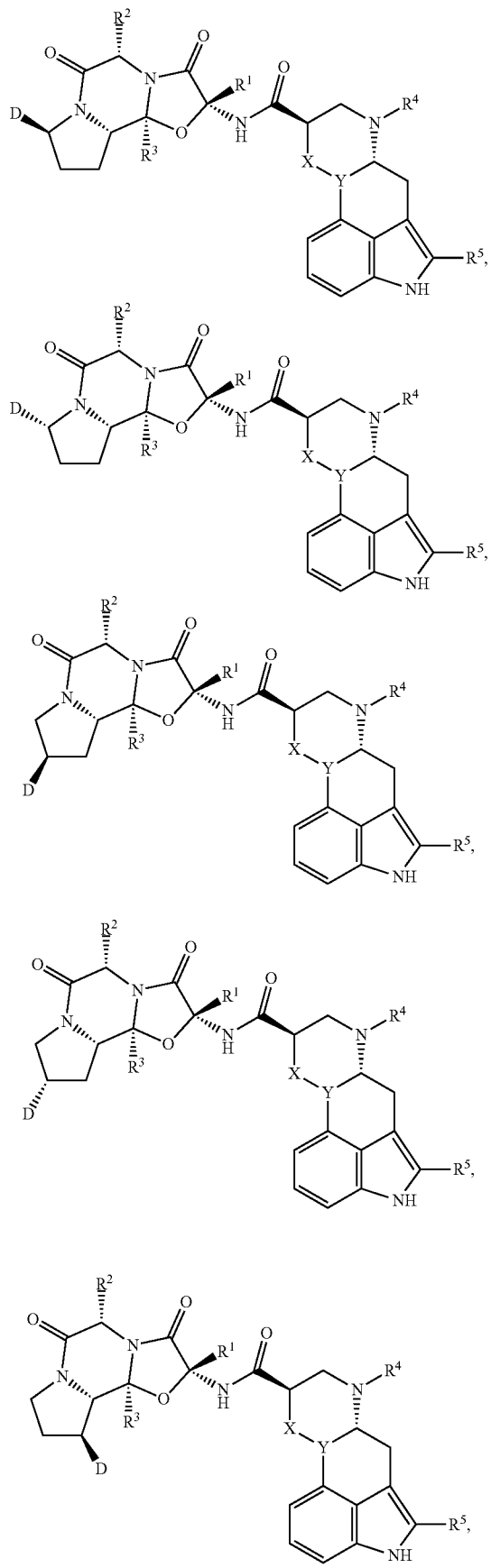

15
-continued

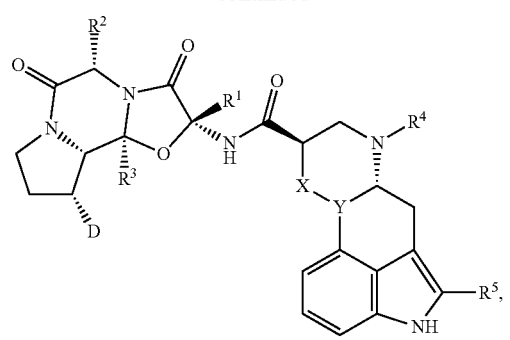

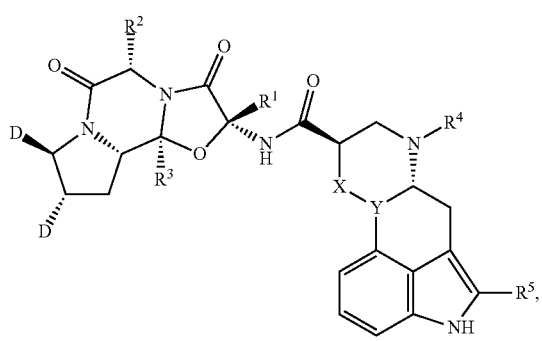

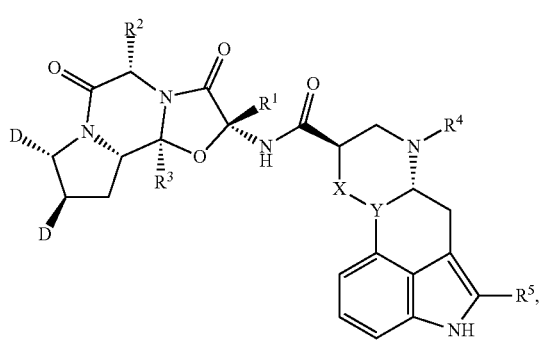

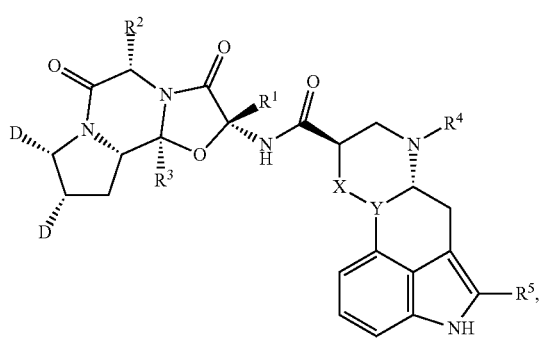

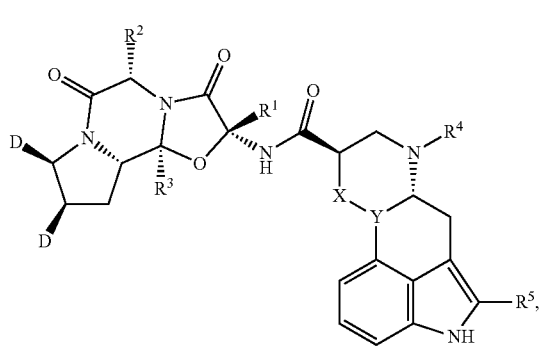

16
-continued

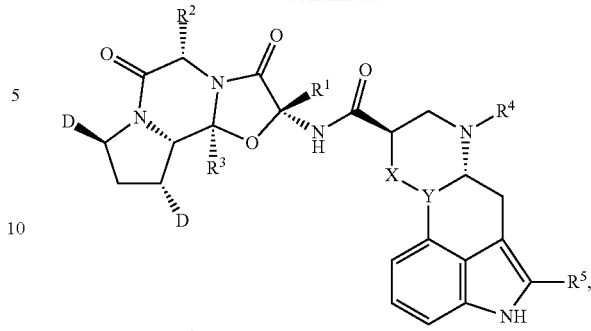

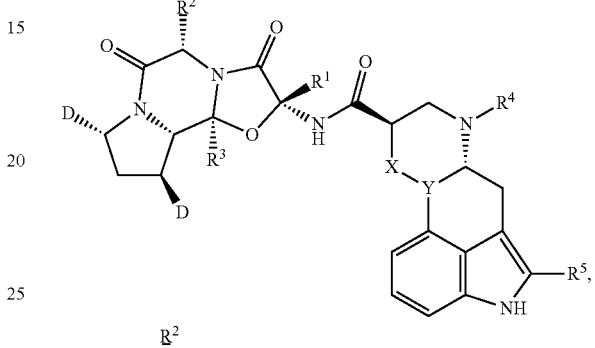

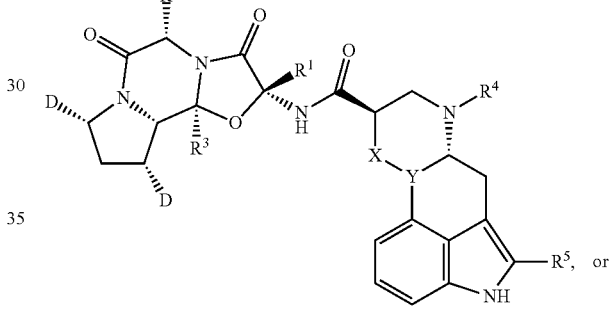

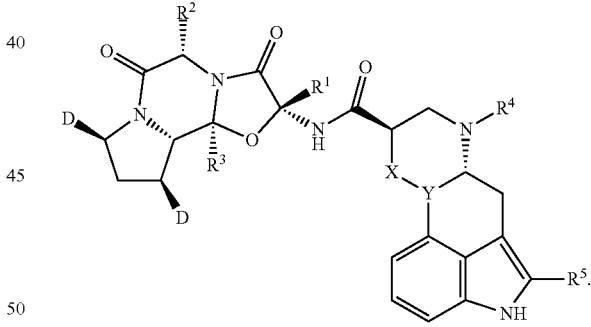

In one embodiment, $R^2$ is hydrogen, trifluoromethyl, halogen, cyano, nitro, methyl, ethyl, propyl, n-butyl, $C_{5-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$.

In one embodiment, $R^1$ is hydrogen, trifluoromethyl, methyl, ethyl, n-propyl, n-butyl, $C_{5-10}$ alkyl, $C_{2-10}$ alkenyl, $C_{2-10}$ alkynyl, $C_{3-10}$ cycloalkyl, aryl, or alkylaryl.

In one embodiment, $R^5$ is hydrogen, trifluoromethyl, fluoro, chloro, iodo, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^x$-$COR^y$, $NR^xCO_2R^y$, $NR^xSO_2R^y$, $COR^x$, or $CO_2R^x$.

In one embodiment, X—Y is a carbon-carbon single bond.

In one embodiment, $R^2$ is benzyl.
In one embodiment, $R^3$ is OH.
In one embodiment, $R^4$ is methyl.
In one embodiment, parasitic worm infection in a vertebrate, such as a mammal, is prevented, inhibited or treated with a composition having an effective amount of a compound of formula (II):

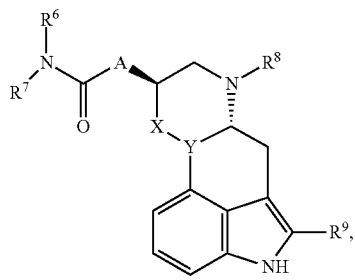

Formula (II)

wherein, $R^6$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^7$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^8$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^9$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond;

A is a bond or $NR^x$;

deuterated analogs thereof, or pharmaceutically acceptable salts thereof.

A composition having a compound of formula (II) may have at least 50%, 60%, 70%, 80%, 85%, 95% or more at one or more deuterated positions.

In one embodiment, X—Y is a carbon-carbon double bond.

In one embodiment, $R^9$ is hydrogen, trifluoromethyl, fluoro, chloro, iodo, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^x$-$COR^y$, $NR^xCO_2R^y$, $NR^xSO_2R^y$, $COR^x$, or $CO_2R^x$.

In one embodiment, A is NH.
In one embodiment, $R^6$ is H, methyl, or ethyl.
In one embodiment, $R^7$ is —$CH(CH_2CH_3)(CH_2OH)$.
In one embodiment, $R^7$ is ethyl, n-propyl, or

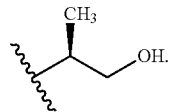 [SMILES: *[C@@H](C)CO]

Routes and Formulations

Administration of compositions having one or more ergot alkaloids, ergopeptines lysergic acid amides, or dimethoxy-isoquinoline derivatives, or any combination thereof, can be via any of suitable route of administration, particularly parenterally, for example, orally, intravenously, intra-arterially, intraperitoneally, intrathecally, intraventricularly, intraurethrally, intrasternally, intracranially, intramuscularly, or subcutaneously. Such administration may be as a single dose or multiple doses, or as a short- or long-duration infusion. Implantable devices (e.g., implantable infusion pumps) may also be employed for the periodic parenteral delivery over time of equivalent or varying dosages of the particular formulation. For such parenteral administration, the compounds may be formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

The compositions invention alone or in combination with other active agents can be formulated as pharmaceutical compositions and administered to a vertebrate host, such as a human patient in a variety of forms adapted to the chosen route of administration, e.g., orally or parenterally, by intravenous, intramuscular, topical or subcutaneous routes.

Thus, the compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the vertebrate's diet. For oral therapeutic administration, the composition optionally in combination with another active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of the compound and optionally other active compound in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound optionally in combination with another active compound may be incorporated into sustained-release preparations and devices.

The composition optionally in combination with another active compound may also be administered intravenously or intraperitoneally by infusion or injection. Solutions of the compound(s) optionally in combination with another active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms during storage can be brought about by various antibacterial and antifungal agents, for example, parabens, chlorobutanol, phenol, sorbic acid, thimerosal, and the like. In many cases, it may be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compound(s) in the required amount in the appropriate solvent with various of the other ingredients enumerated above, as required, followed by filter sterilization. In the case of sterile powders for the preparation of sterile injectable solutions, one method of preparation includes vacuum drying and the freeze drying techniques, which yield a powder of the active ingredient plus any additional desired ingredient present in the previously sterile-filtered solutions.

For topical administration, the compound(s) optionally in combination with another active compound may be applied in pure form, e.g., when they are liquids.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In addition, in one embodiment, the invention provides various dosage formulations of the compound(s) optionally in combination with another active compound for inhalation delivery. For example, formulations may be designed for aerosol use in devices such as metered-dose inhalers, dry powder inhalers and nebulizers.

Useful dosages can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) optionally in combination with another active compound in a liquid composition, may be from about 0.1-25 wt-%, e.g., from about 0.5-10 wt-%. The concentration in a semi-solid or solid composition such as a gel or a powder may be be about 0.1-5 wt-%, e.g., about 0.5-2.5 wt-%.

The active ingredient may be administered to achieve peak plasma concentrations of the active compound of, in one embodiment, from about 0.5 to about 75 $\mu$M, e.g., about 1 to 50 $\mu$M, such as about 2 to about 30 $\mu$M. This may be achieved, for example, by the intravenous injection of a 0.05 to 5% solution of the active ingredient, optionally in saline; or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the compound(s) optionally in combination with another active compound, or an active salt or derivative thereof, required for use in treatment may vary not only with the particular salt selected but also with the route of administration, the nature of the condition being treated and the age and condition of the patient and will be ultimately at the discretion of the attendant physician or clinician. In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for instance in the range of 6 to 90 mg/kg/day, e.g., in the range of 15 to 60 mg/kg/day.

The compound(s) optionally in combination with another active compound may be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual vertebrate. In general, the total daily dose range for an active agent for the conditions described herein, may be from about 1 mg to about 100 mg, from about 10 mg to about 50 mg, from about 10 mg to about 40 mg, from about 20 mg to about 40 mg, from about 20 mg to about 50 mg, from about 50 mg to about 5000 mg, in single or divided doses. In one embodiment, a daily dose range should be about 100 mg to about 4000 mg, e.g., about 1000-3000 mg, in single or divided doses, e.g., 750 mg every 6 hr of orally administered compound. This can achieve plasma levels of about 500-750 uM, which can be effective to kill cancer cells. In managing the patient, the therapy should be initiated at a lower dose and increased depending on the patients global response.

The invention will be described by the following non-limiting examples.

Example 1

Materials and Methods

Compounds and Reagents.

Serotonin (5-HT), 3-Isobutyl-1-methylxanthine (IBMX) and DMSO were purchased from Sigma Aldrich. The GPCR Compound Library was purchased from Selleck Chemicals (Catalog No. L2200) pre-dissolved in DMSO (10 mM). 5HT$_7$ ligands DR4485, LY215840, metergoline and 5-Carboxamidotryptamine (5-CT) were purchased from Tocris Bioscience. Methoxy-isoquninoline alkaloids (rotundine, tetrabenazine, berbine, palmatine, tetrandrine and berbamine) were purchased from Sigma Aldrich, while fangchinoline was purchased from AK Scientific.

Cell Culture and 5-FIT Receptor Expression.

HEK293 cells (ATCC CRL-1573.3) were cultured in DMEM supplemented with 10% fetal bovine serum (FBS), penicillin (100 units/mL), streptomycin (100 µg/mL), and L-glutamine (290 µg/mL). Cells were transiently transfected (ViaFect, Promega) as per the manufacturer's protocol at a density of $2 \times 10^6$ cells per T-25 cell-culture flask. Cells were transfected with plasmids encoding GloSensor (Promega) and either Sm.5HTR, (Smp_126730, GenBank accession number KF444051.1) or Sm.5HTR$_L$ (KX150867), both GPCRs being codon optimized for mammalian expression, or Hs.5HT7a (GenBank accession number NM_000872.4, R&D Systems) subcloned into pCS2(-). Cell culture reagents were from Invitrogen. Epitope tagged constructs were used to verify expression, and untagged constructs used for all luminescence assays.

Western Blotting.

HEK293 cells were transfected with Sm.5HTR subcloned into a pCS2(-) mammalian expression vector possessing an NFL-terminal 6×myc tag and harvested 24 hours post-transfection. Cell pellets were solubilized in 1% NP-40, protein was quantified using Bradford reagent (Pierce). Denatured sample (10 µg) was run on a Mini-PROTEAN TGX Precast Gel (BioRad) at 150V. Semi-dry transfer to PVDF membrane was performed using a Trans-Blot Turbo Mini-PVDF Transfer pack (Bio Rad) at 25V for 30 minutes. The membrane was blocked with 5% nonfat milk in TBST (Tris-buffered saline, 0.1% Tween 20) for 1 hour at room temperature, incubated with anti-myc antibody overnight at 4° C. (Santa Cruz, 1:500 dilution in 5% milk-TBST) prior to washing in TBST (3×10 minutes) and incubation with secondary antibody (LiCor Goat anti-mouse IRDye 800, 1:5000 dilution in 5% milk-TBST) for 1 hour at room temperature. After washing (3×10 minutes in TBST), membranes were visualized on a LiCor Odyssey imaging system.

Molecular Cloning.

Sequence for Sm.5HTR$^L$ was determined by cloning from an *Schistosoma mansoni* cDNA library (adult male and female NMRI strain, BEI cat #NR-36056) using high fidelity Advantage HD DNA polymerase (Clontech) and primers described in (Patocka et al., 2014). PCR products were ligated into the pGEM-T Easy vector system (Promega) prior to DNA sequencing. Additional sequence contained in the Sm.5HTR$_L$ isoform was verified by 5'/3' RACE (SMARTer RACE Kit, Clontech) using total RNA extracted from *S. mansoni* (Trizol reagent, Ambion). Products were cloned into the pRACE vector (In-Fusion HD Cloning Kit, Clontech) prior to DNA sequencing.

GloSensor cAMP Assays.

For assays performed on adherent cells, HEK-293 cells were transferred one day post transfection to 96 well, solid white plates (Corning, cat #3917) coated with 0.01% poly-L-lysine (Sigma Aldrich) at a density of $5 \times 10^4$ cells/well in DMEM supplemented with 1% dialyzed FBS (Gibco). After overnight culture (37° C./5% $CO_2$), media was decanted and replaced with 100 µL/well HBSS supplemented with 0.1% BSA, 20 mM HEPES (pH 7.4) and GloSensor™ reagent. Plates were allowed to equilibrate at room temperature for two hours prior to performing luminescence assays (Glo-Max-Multi Detection System plate reader, Promega). Conditions for individual assays were described as per figure legends. The standard assay to detect changes in cAMP utilized the F22 sensor in media supplemented with IBMX (200 µM). Ligands were added at a concentration of 20× per well for experiments (i.e., 5 µl of drug solution added to 100 µL of cells). A dose of 5-HT corresponding to the [$EC_{80}$] for the relevant receptor used for all antagonist screens. The average standard deviation of the 5-HT $E_{max}$ in internal, vehicle treated control wells (at least 8 per plate) was 13% for Sm.5HTR and 8% for Hs5HT7R. For the resazurin reduction assay for cellular viability, cells were incubated with resazurin (final concentration, 10 µM) and tested ligands with fluorescence measurements (560 nm excitation/590 nm emission) made at 1.5 hours intervals.

To test putative irreversible antagonists, assays on suspension cells were performed one day post transfection. Cells in a T-75 flask were trypsinized (0.25% w/v) and transferred to a 14 mL tube, centrifuged at 300 RCF, and resuspended in HBSS supplemented with 0.1% BSA, 20 mM HEPES. Compounds were added at 10 µM, and after 30 minutes incubation at room temperature cells were centrifuged (300 RCF, 5 minutes) and resuspended in fresh media. This wash step was repeated, and cells were resuspended in HBSS supplemented with 0.1% BSA, 20 mM HEPES and GloSensor reagent. Cells were gently rotated to prevent aggregation and settling over the course of the two hour equilibration period, after which time they were transferred to 96 well plates at a density of $8 \times 10^4$ cells/100 µL per well and assays described for adherent cells.

Schistosomule Assays.

*Biomphalaria glabrata* (M-line) snails exposed to *Schistosoma mansoni* miracidia (Strain PR-1) were obtained from BEI Resources (Cat. number NR-21961) and cercaria were shed following exposure to light (1.5 hours). Cercaria were manually transformed into schistosomula by vortexing (3×45 seconds, each separated by 3 minutes on ice) and tails were removed by gradient centrifugation (24 mL Percoll, 4 mL 10×EMEM, 1.5 ml penicillin-streptomycin, 1 mL of 1M HEPES in 0.85% NaCl, 9.5 ml distilled water) at 500 g/15 minutes at 4° C. Supernatant containing tails was discarded, and schistosomules were resuspended in Basch media and incubated (37° C., 5% $CO_2$) overnight before conducting mobility assays. For contractility experiments, somules were incubated in 5-HT free Basch media to resolve a basal contractility rate. To establish a dose response curve for 5-HT, serial dilutions of 5-HT were added to Basch media and somule contractile frequency recorded. In order to assess the effects of antagonists on somule movement, recordings were made of cohorts in 5-HT free Basch media, media supplemented with 5-HT (10 µM), and media supplemented with both 5-HT (10 µM) and the drugs indicated in FIG. 8. Schistosomules were incubated in 24 well plates (about 200 schistosomules/0.5 mL media per well) for 30 minutes (37° C./5% $CO_2$) prior to acquiring videos of schistosome movement (1 minute recordings/well) using a Nikon Coolpix 5700 camera affixed to a Nikon Eclipse TS100 microscope (10× objective). The WrmTrck plugin for ImageJ was used to quantify worm mobility (El-Shehabi et al., 2012). Briefly, the major axis of each schistosomule body length was extracted from the raw output of WrmTrck and an average length was determined for the duration of the recording. Contractions were quantified by determining the number of episodes during which the worm body length deviated from the average by over 20%. *S. mansoni* protocols were approved by the Iowa State University Institutional Biosafety Committee.

Adult Schistosome Mobility Assays.

Female Swiss Webster mice exposed to *Schistosoma mansoni* cerceria (Strain PR-1) at 5-7 weeks old were obtained from BEI Resources (Cat, number Ni-34792) and sacrificed 6-8 weeks post-infection. Mature *S. mansoni* were harvested from the mesenteric vasculature by portal perfusion (Tucker et al., 2013). Briefly, mice were anesthetized in a $CO_2$ chamber and sacrificed by cervical dislocation. Mice were perfused with sodium citrate (25 mM) and adult schistosomes were harvested from the mesenteric veins. Schistosomes were washed in RPMI media containing penicillin (1000 units/mL), streptomycin (1000 μg/mL) and 25 mM HEPES, then transferred to RPMI media supplemented with 2 mM glutamine and 5% heat inactivated MS. Worms were incubated overnight at 37° C., 5% $CO_2$ before conducting assays. Recordings of adult schistosome movement were captured using a Zeiss Discovery v20 stereomicroscope and a QiCAM 12-bit cooled color CCD camera. Videos were acquired at a rate of four frames per second for one minute. Recordings of female worms were acquired at 7.6× magnification, 30 mm field of view and recordings of male worms were acquired at a 5.1× magnification, 45 mm field of view. Analysis was performed in ImageJ as described previously (MacDonald et al., 2015). Briefly, image (.tiff) stacks of each recording were imported and processed by converting to binary format so that pixel measurements represent area of the worms' bodies. Mobility was quantified by measuring the difference in pixels resulting from subtracting the value of one frame (n) from those of the next frame in the sequence (n+1). This difference was expressed as a percentage of the pixels in the initial frame (n), providing a measurement of the worms' movement over a period of 0.25 seconds. This calculation was performed for each frame in the video, and the results were averaged over the length of the recording. Values reported represent the mean (±) standard error of at least three independent experiments. Animal work was carried out with the oversight and approval of the Laboratory Animal Resources facility at the Iowa State University College of Veterinary Medicine.

Results

No high throughput screen of a flatworm GPCR has been reported, even though these targets have precedent for high druggability and functionality in the chemotherapeutically vulnerable excitable cell niche. As discussed below, a method was established for profiling flatworm G protein coupled receptors that can be scaled to high content screening. Using this cAMP biosensor, a miniaturized screen was performed on a schistosome serotonergic GPCR that resolves new ligands that potently and selectivity block 5-HT receptor activity in vitro, and 5-HT evoked responses in schistosomules and adult worms. This approach evidences the pharmacological divergence of a parasitic GPCR from the closest human homolog, and a capacity for high content interrogation of flatworm GPCR properties and ligand specificities.

Functional Expression of a Schistosome 5-HT Receptor.

In schistosome parasites, 5-HT is myoexcitatory: exogenous addition of 5-HT to schistosomules causes an increase in basal contractility and 5-HT also increases mobility of adult worms (Pax et al., 1984; Willcockson and Hillman, 1984). While this action has long been known, it is only in the last several years that the relevant receptors mediating the effects of 5-HT in flatworms have been identified (Chan et al., 2015; Patocka et al., 2014). The most abundant schistosome 5-HT receptor in adult worms from transcriptomic analysis (Protasio et al., 2012), is a recently characterized GPCR christened Sm.5HTR (Patocka et al., 2014).

Expression of an epitope tagged Sm.5HTR construct in HEK293 cells resulted in expression of about 56 kDa product, consistent with the predicted size (FIG. 1A). To assess functionality of this receptor, the GloSensor cAMP assay was utilized as a real-time luminescent readout of cellular cAMP levels. This 'biosensor' monitors luminescence from a firefly luciferase that is engineered to be cAMP sensitive by incorporation of a cAMP binding domain into the recombinant luciferase. The presence of substrate and cAMP results in an enhanced luminescence from the transfected GloSensor™ construct (FIG. 1B), allowing real time monitoring of cAMP levels within intact cells. This can be seen in HEK293 cells transfected with both Sm.5HTR and GloSensor™, where application of 5-HT evoked an increase in luminescence values over time (FIG. 1C). No changes in cAMP were elicited in HEK.293 cells transfected with the biosensor alone (FIG. 1C).

Optimization of Assay Conditions.

Figure 2A:
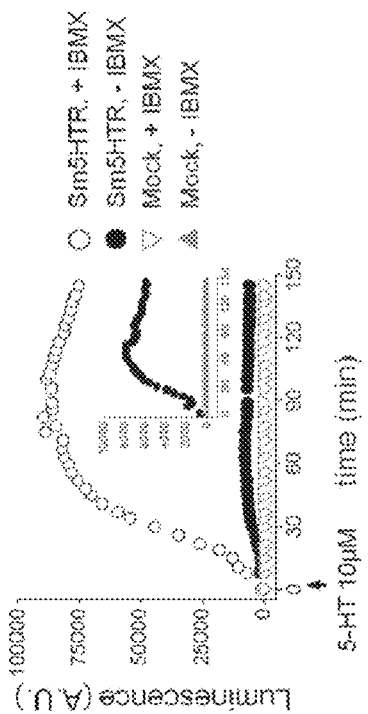
Figure 2B:
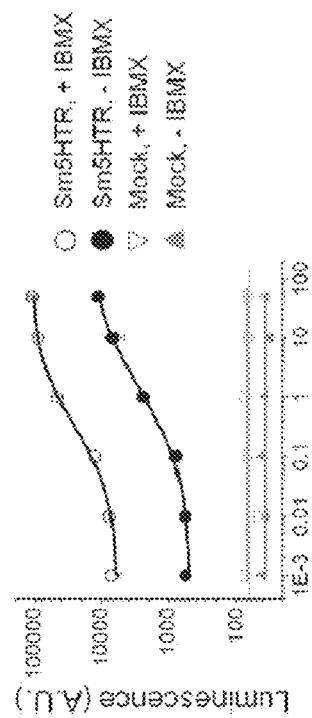
Figure 2C:
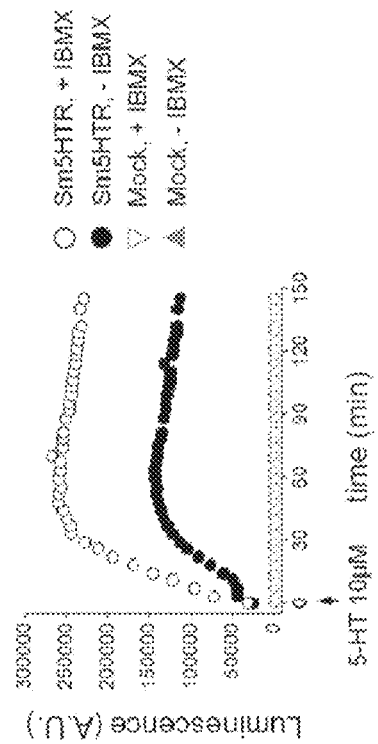
Figure 2D:
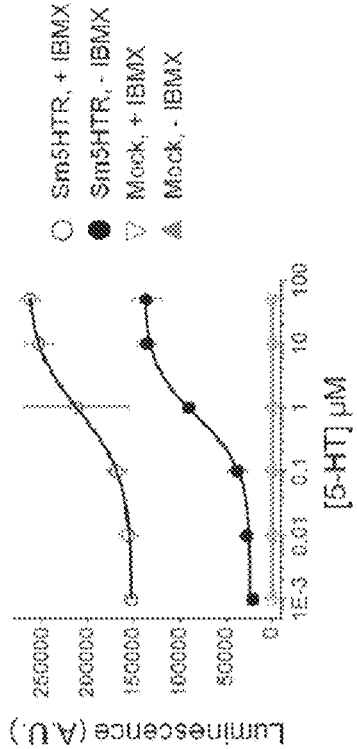

Measurements of assay sensitivity were made from 5-HT evoked luminescence signals in cells plated in 96-well plates transfected with cAMP biosensors exhibiting either high affinity ('F20' construct) or low affinity ('F22' construct) for cAMP (FIG. 2A-B). As expected, the magnitude of the luminescence signal varied with 5-HT application in a dose-dependent manner with both biosensor constructs in Sm.5HTR transfected cells (FIG. 2C-D). With the higher affinity 20F sensor, the $EC_{50}$ for cAMP generation was 703±90 nM (n=3, FIGS. 2C-D and Table 1), with the dose response relationship shifting to higher values with the 22F sensor as previously established (Binkowski et al., 2011). The magnitude of the response was greatest in media supplemented with 3-isobutyl-1-methylxanthine (IBMX, 200 μM) to block cAMP degradation. In the presence of IBMX, higher overall luminescence values were recorded with peak signal to background changes of about 1.7-fold and about 15.1-fold for 20F and 22F respectively (FIGS. 2A-D), providing a good signal to background window for monitoring receptor activation.

Figure 3A:
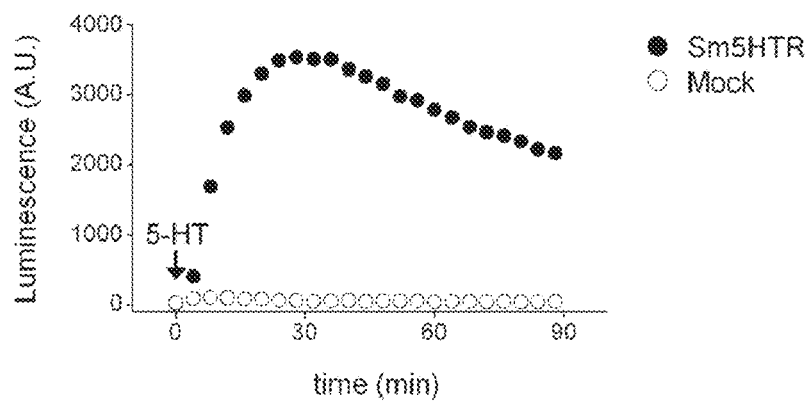
FIGS. 3A-C. Sm.5HTR GloSensor luciferase assay in 384 well plate format. (A) HEK293 cells transiently transfected with Sm.5HTR and the F22 cAMP biosensor were assayed for changes in luminescence in response to addition of 5-HT (10 µM, arrow). (B) Dose response curve depicting luminescence values assayed 60 mins following 5-HT addition. (C) Z'-scores over time illustrated for the representative experiment shown in (A). All experiments shown performed in the presence of IBMX (200 µM).
Figure 3B:
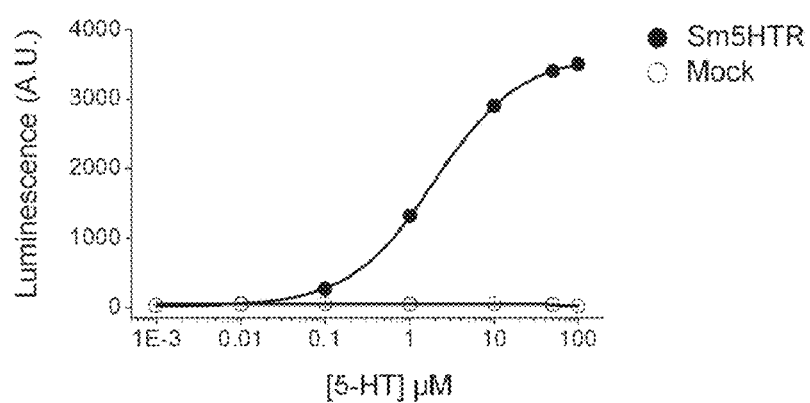
Figure 3C:
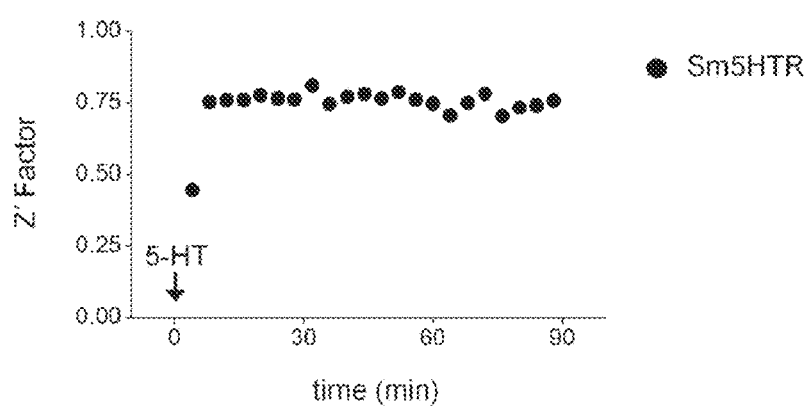

The robustness of these cAMP assays was assessed by calculating the Z' factor (Z'), a widely used indicator of assay quality in high throughput screening applications (Zhang et al., 1999). Z' values over 0.5 are considered a prerequisite for executing high throughput screens. Calculations of Z' were made at different timepoints during the agonist response, averaging 6 replicate wells within a 96 well plate. The highest Z' scores were obtained with the F22 sensor supplemented with IBMX (FIGS. 2E-F), and these conditions were used for all subsequent assays. Acceptable Z' values were also obtained with cells in suspension (Table 1) and under conditions of further miniaturization to 384-well plates (FIG. 3).

TABLE 1

Summary statistics for live cell GloSensor cAMP assays on Sm•5HTR. Z' factor, signal window and $EC_{50}$ were calculated at 60 minutes after delivery of 5-HT (10 μM).

|  | F20 | | F22 | |
| --- | --- | --- | --- | --- |
|  | (−) IBMX | (+) IBMX | (−) IBMX | (+) IBMX |
| Adherent Cells | | | | |
| Z' factor* | 0.4 | 0.7 | −0.1 | 0.7 |
| Signal window** | 3.1 | 3.6 | −0.3 | 12.3 |
| $EC_{50}$ | 0.7 μM | 0.9 μM | 16.1 μM | 2.0 μM |
| Suspension Cells | | | | |
| Z' factor* | 0.9 | 0.2 | 0.7 | 0.9 |
| Signal window** | 37.5 | 0.7 | 7.4 | 40.8 |
| $EC_{50}$ | 1.4 μM | 1.0 μM | 4.2 μM | 3.8 μM |

*Z' factor calculated for vehicle control and 5-HT (10 μM); $Z' = 1 - (3(stdev_{max} + stdev_{min})/(mean_{max} - mean_{min})$.
**Signal window calculated for vehicle control and 5-HT (10 μM), defined as $SW = (mean_{max} - mean_{min} - 3(stdev_{max} + stdev_{min}))/stdev_{max}$.

Figures 4A, 4B:
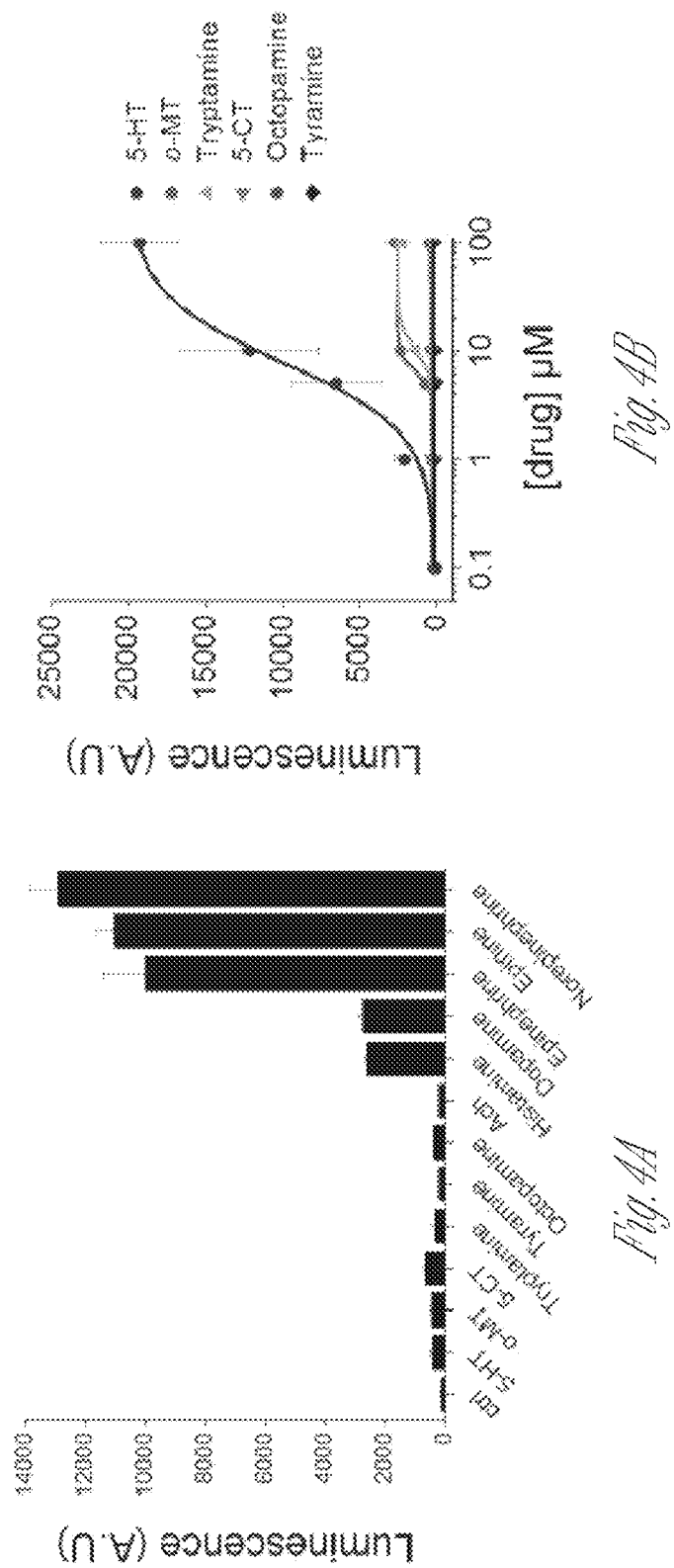
FIGS. 4A-B. Sm.5HTR response to bioaminergic ligands. (A) Response of HEK293 cells transfected with the F22 GloSensor to various Class A GPCR ligands (10 µM), revealing a lack of responsiveness to serotonergic ligands but robust cAMP generation in response to catecholamines acting on endogenous HEK293 cell GPCRs. (B) Response of HEK293 cells co-expressing Sm.5HTR and the F22 biosensor to various serotonergic and monoaminergic ligands previously identified to lack activity on endogenous $G_s$ coupled GPCRs.

Unlike assays requiring cell lysis for fixed timepoint measurement, the live cell biosensor allowed real time monitoring of cellular cAMP levels throughout ongoing experimental manipulations. FIG. 2G demonstrates antagonism of 5-HT stimulated cAMP generation by the antipsychotic methiothepin (Day et al., 1994), with cellular responsiveness demonstrable by the subsequent addition of forskolin. Dose response analyses also confirmed preferential activation of Sm.5HTR by 5-HT compared with other bioaminergic agonists (FIG. 4). Finally, this assay was used to compare responsiveness from two different isoforms of Sm.5HTR which have been isolated—the originally published sequence Sm.5HTR (Patocka et 2014) and a longer isoform (Sm.5HTR$_L$) containing addition sequence at the $NH_2$-terminus and within the third intracellular loop (FIG. 2H, inset). Both isoforms were activated by 5-HT, with Sm.5HTR$_L$ displaying about 10-fold greater sensitivity ($EC_{50}$ 0.2±0.03 μM vs 2.0±0.2 μM, FIG. 2H) but a similar kinetic response (FIG. 2I).

Pharmacological Profiling of Sm.5HTR Against a GPCR Modulator Library.

Sequence homology identifies Sm.5HTR as a member of the SER7 Glade of serotonin receptors, clustering with planarian S7 receptors (Chan et al., 2015) and with Hs.5HT7R, as the closest human homolog (Patocka et al., 2014). To characterize the extent of pharmacological conservation between the parasite and human serotonin receptor, the miniaturized cAMP assay was used to screen a commercial GPCR compound library (about 250 compounds) for inhibitors of these receptors. An inhibitor screen was prioritized simply because of the improved likelihood of detecting antagonists over agonists (need to exclude false positives from stimulation of endogenous receptors), and the utility of these agents for blocking parasite motility, The protocol for screening is shown schematically in FIG. 5A. HEK293 cells transiently transfected with either the human $5HT_7$ receptor (Hs.5HT7R) or the schistosome receptor (Sm.5HTR) were exposed to test ligands in a 96-well plate format. After addition of test compounds, 5-HT was then added to each well at a concentration corresponding approximately to the $EC_{80}$ of each receptor to assess blockade of 5-HT effects by prior compound addition. Luminescence was then read at a fixed time point (t=60 minutes, FIG. 5A). Hits were assigned as compounds that evoked a ≥50% decrease in luminescence output at the fixed time sampling point (FIG. 5B). These experiments identified 25 compounds as potential antagonists of Sm.5HTR evoked cAMP generation (FIG. 5B).

Figure 5E:
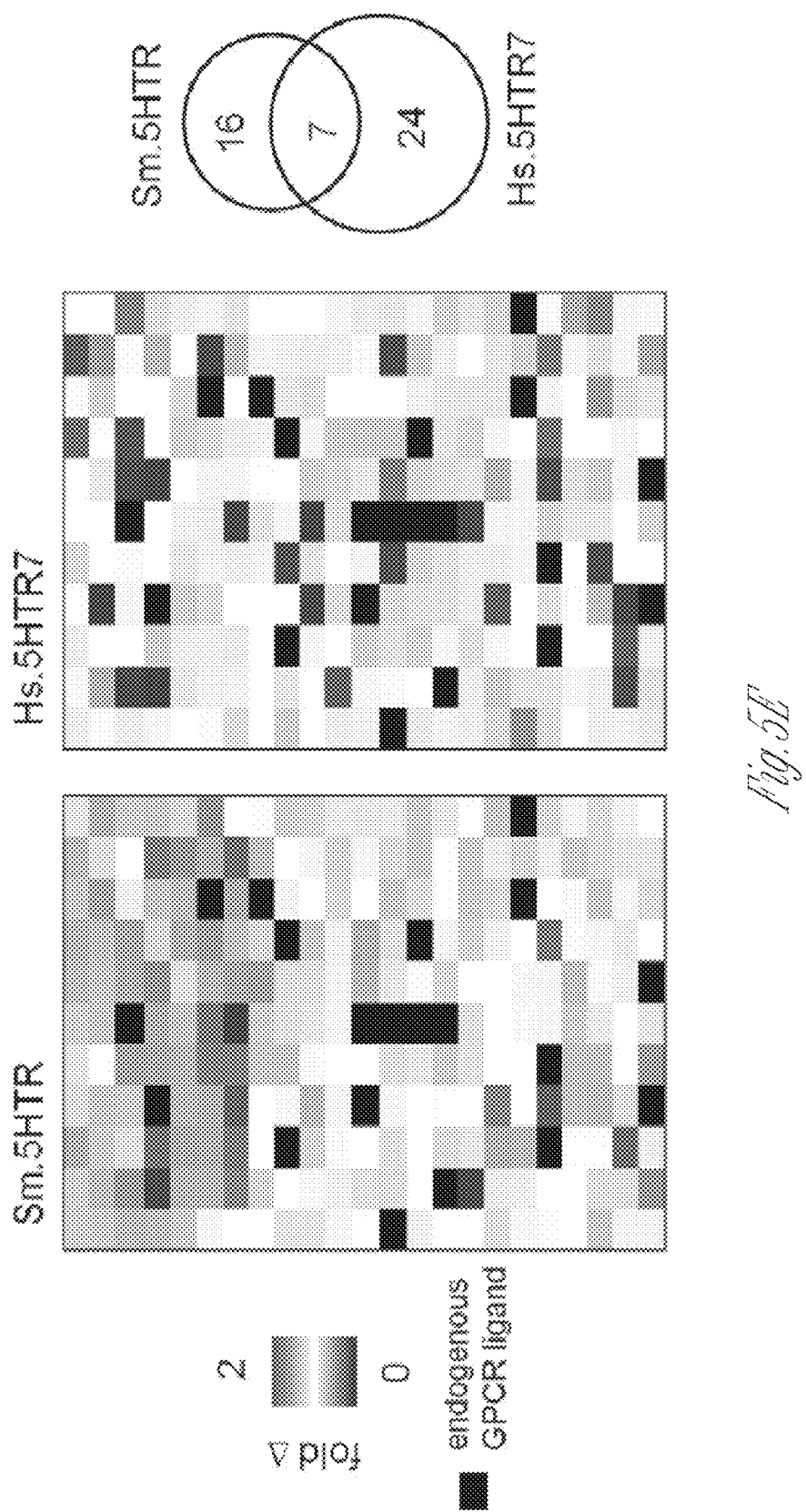

Two sets of validation experiments were then performed in order to remove false 'hits' from the dataset. First, the same library was also screened against naive HEK293 cells as a control for responses resulting from engagement of endogenous GPCRs (FIG. 5C). This analysis identified 14 compounds in the library that activated endogenous $G_s$-coupled GPCRs in HEK293 cells (Fan et al., 2008). Second, to exclude ligands that inhibited either cAMP production (for example, through activation of endogenous $G_i$-coupled GPCRs) or directly impaired the activity of the luciferase biosensor, the library was screened against forskolin-evoked increases in cAMP (FIG. 5D). This analysis identified 7 compounds that decreased luminescence values >2-fold in forskolin-treated control cells. These 21 compounds were 'masked' from the experimental dataset and the overall pharmacological profile of Sm.5HTR and Hs.5HTR7 were then represented as a heat map to depict ligand-evoked changes in cAMP levels (FIG. 5E). This visual representation conveys in a simple manner the extent of pharmacological divergence between the human and schistosome GPCRs. Some drugs displayed a unique affinity for Sm.5HTRs, others preferentially modulated Hs.5HT7R, and some ligands blocked both receptors. Overall, 23 compounds were retained for subsequent validation as antagonists of Sm.5HTR with only a minor proportion of these compounds (7 'hits') showing inhibition at both the human and parasite receptor (FIG. 5E, inset). A simple overview of the pharmacological specificity of the compounds identified as antagonists using the ligand classification key associated with the library was also informative (FIG. 6). The types of ligand classes if not compound identities that inhibited each serotonergic GPCR was broadly similar. The only notable difference was blockade of Sm.5HTR by some cholinergic ligands, which was not apparent for Hs.5HT7R.

Figure 7A:
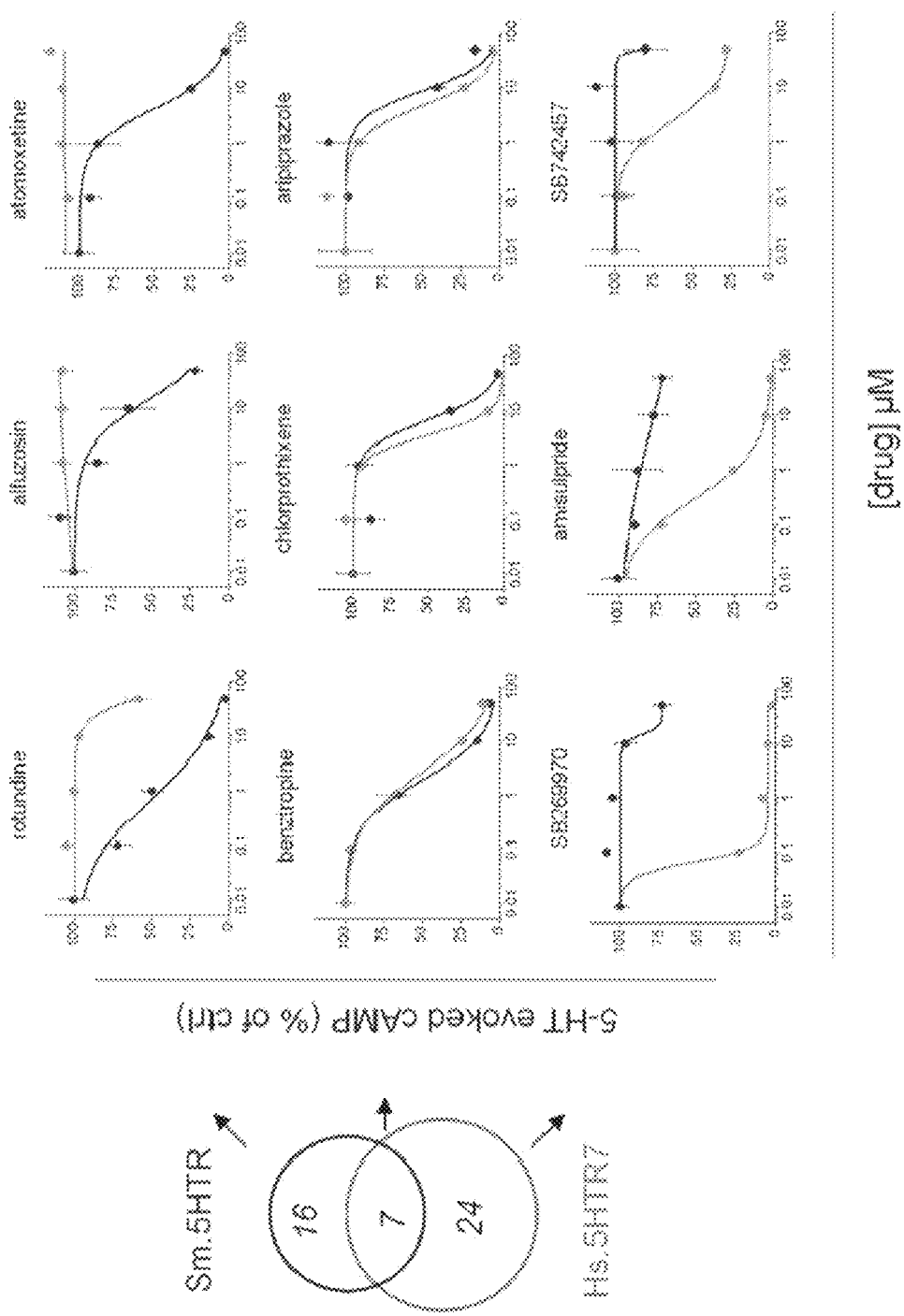
FIGS. 7 A-B. Profiling ligand selectivity for schistosome and human 5HT7 receptors. (A) Dose response relationships for compound antagonism of 5-HT evoked cAMP generation at human Hs.5HT7R (green) or parasite Sm.5HTR (blue) GPCRs. Illustrative data from compounds showing preferential selectivity toward Sm.5HTR (top) or Hs.5HT7R (bottom), or compounds with no selectivity (middle). Data represent mean±s.d, n=3. (B) Schematic representation of ratio of $IC_{50}$s for 'hits' profiled against both Sm.5HTR and Hs.5HT7R expressing HEK293 cells. Compounds exhibiting poor blockade of either GPCR (*) precluded calculation of $IC_{50}$ values, so a minimal ratio estimate is provided. Solid circles represent compounds for which data is shown in 'A'.
Figure 8:
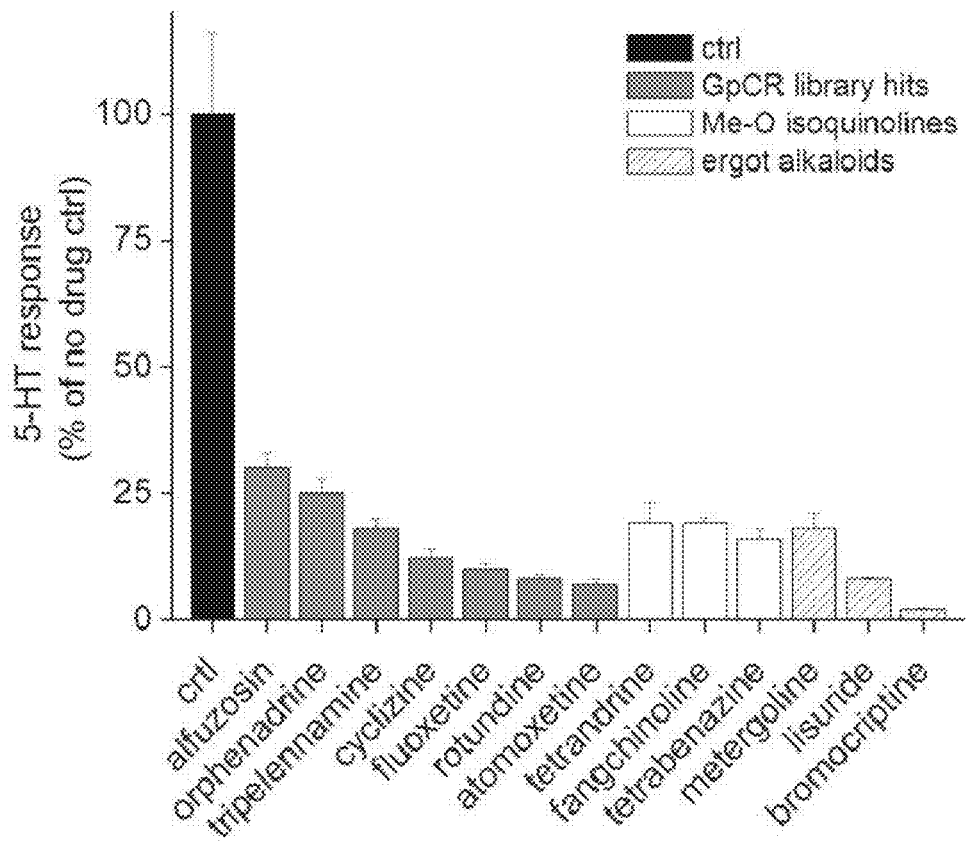
FIG. 8. Effect of Sm.5HTR antagonists on Sm.5HTR$_L$. Luminescence response from Sm.5HTR$_L$ expressing HEK293 cells to 5-HT ($EC_{80}$ dose=0.8 μM) in the presence of indicated antagonists (10 μM). Data are shown relative to control samples unexposed to antagonist (black). Antagonist compounds screen encompass compounds from the GPCR library screen (grey), methoxy-isoquinolines (open), and ergot alkaloids (striped).
Figure 9A:
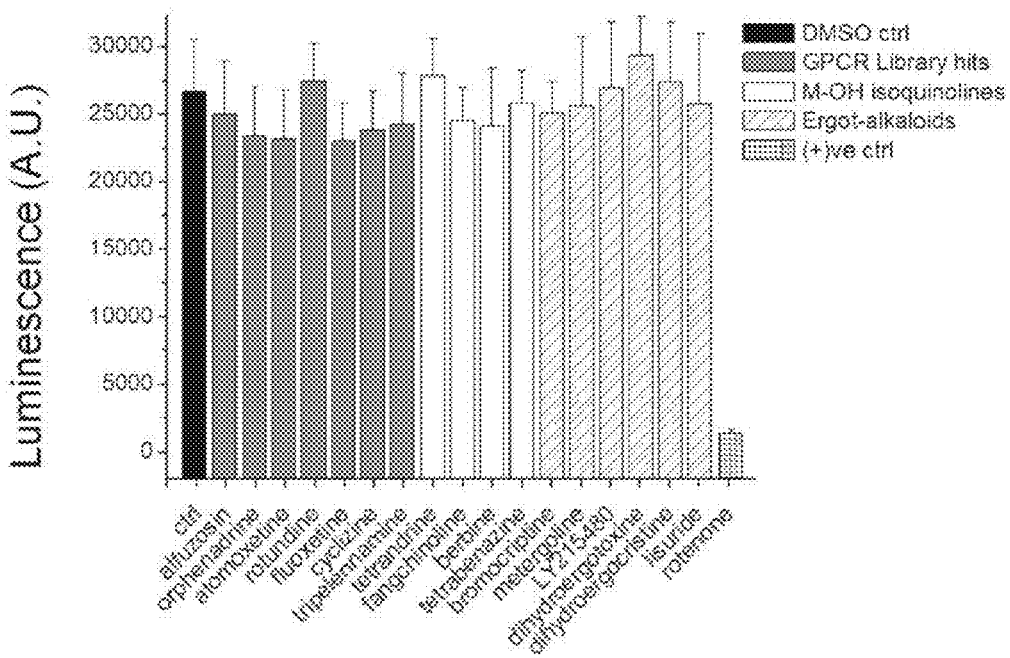
FIGS. 9A-B. Toxicity test for screened compounds. (A) HEK293 cells transiently transfected with the F22 cAMP biosensor were incubated with test compounds (10 μM, 30 minutes) and then assayed for forskolin (2.0 μM, 30 minutes) evoked cAMP generation. Tested ligands showed no effects on luminescence signal values. The mitochondrial complex I inhibitor rotenone served as a positive control. (B) Resazurin reduction assay for cell viability of HEK293 cells exposed to test compounds (10 μM) and resazurin (10 μM) for 3 hours at 37° C. Fluorescence was measured using a 560 nm excitation/590 nm emission filter set. Sodium azide was used as a positive control.
Figure 9B:
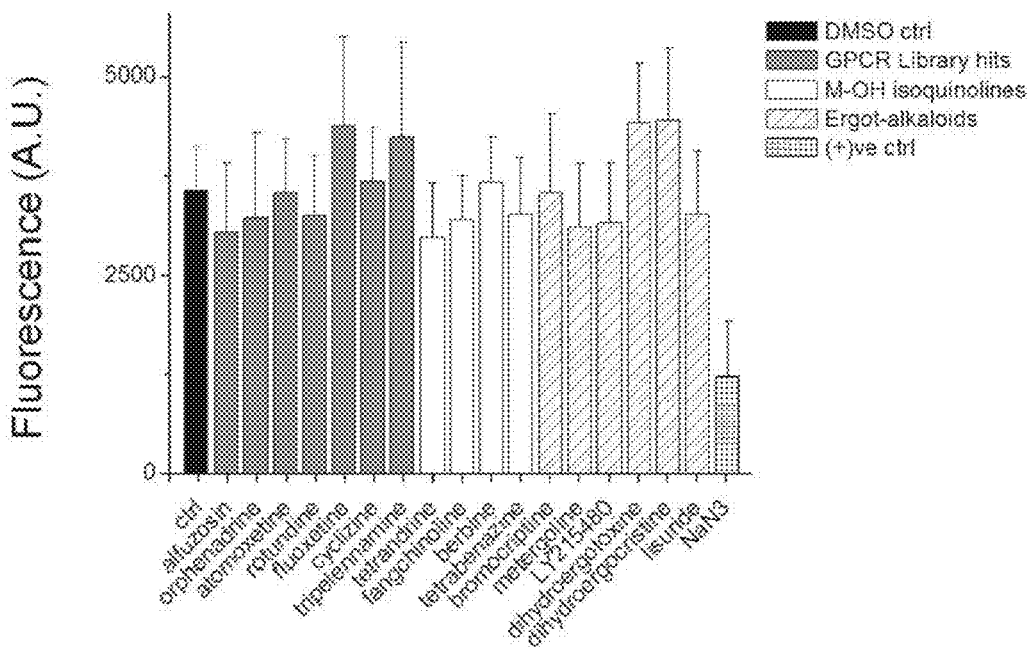

To confirm 'hit' validity, complete dose response relationships were then examined for all compounds that inhibited 5-HT evoked signals by ≥50%. Examples of these assays (FIG. 7) confirm the designation of compounds showing selective inhibition of the parasite serotonin receptor (FIG. 7A, top), blockade of 5-HT receptors from both species (FIG. 7A, middle) and preferential antagonism of the human 5-HT receptor (FIG. 7A, bottom). Calculation of a selectivity ratio ($IC_{50}$ (Hs.5HT7R)/$IC_{50}$ (Sm.5HTR)) for these antagonists (FIG. 7B) revealed a broad continuum of GPCR selectivity among from the screened compounds. Four ligands demonstrated clear selectivity for Sm.5HTR (alfuzosin, orphenadrine, atomoxetine and rotundine, FIGS. 7A and B), of which rotundine displayed the most sensitive $IC_{50}$ value ($IC_{50}$=701±207 nM). These ligands also inhibited 5-HT evoked cAMP generation through Sm.5HTR$_L$ (FIG. 8). However, none of these compounds directly affected biosensor luminescence or cell viability of untransfected cells of at screened dosages (FIG. 9).

Direct Interrogation of Sm.5HTR.

While the above data provide proof of principle for interrogation of a flatworm GPCR against a compound library in a miniaturized format, in was of interest to use the assay to investigate the properties of specific ligands. First, specific ergot alkaloids were profiled on the basis of observations showing these compounds act as efficacious modulators of flatworm physiology (Pax et al., 1984; Semeyn et al., 1982; Tomosky et al., 1974'. Certain ergot alkaloids inhibit schistosomule contractility, while others stimulate hyperactivity (Chan et al., 2015). In regenerating planarians, the ergopeptide bromocriptine evoked bipolarity at concentrations 100-fold less than PZQ (Chan et al., 2014), implying a potency of this class of agents against flatworm bioaminergic receptors. However, the structure-activity relationships (SAR) of ergots at flatworm GPCRs and relative selectivity over human receptors was unknown. Second, there may be an ergomimetic quality to PZQ action, raising the possibility that PZQ itself acts as a direct ligand of flatworm bioaminergic receptors likely as a serotonergic antagonist (Chan et al., 2015). Therefore, screening for PZQ activity against Sm.5HTR was also investigated. Third, Hs.5HTR7 displays a property of pseudo-irreversible antagonism, where a subset of ligands effect a persistent inactivation of the receptor persistent beyond the duration of drug exposure (Smith et al., 2006; Knight et al., 2009). is this phenomenon conserved at Sm.5HTR? Finally, guided by the chemical library data, a secondary screen of compounds structurally related to 'hits' from the initial drug screen ('SAR by commerce') was performed. Each of these experiments are discussed in turn below.

Figure 10A:
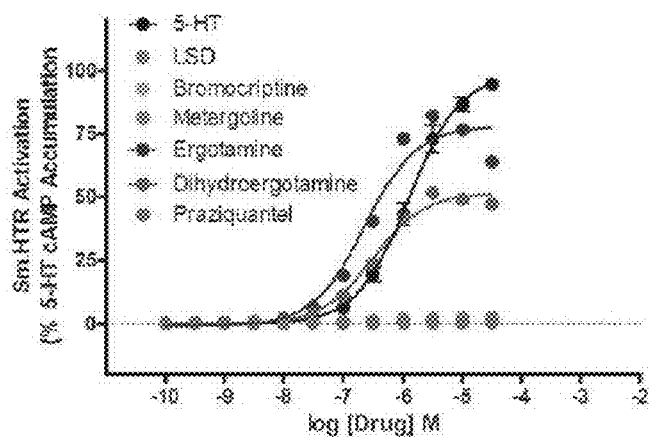
Figure 10B:
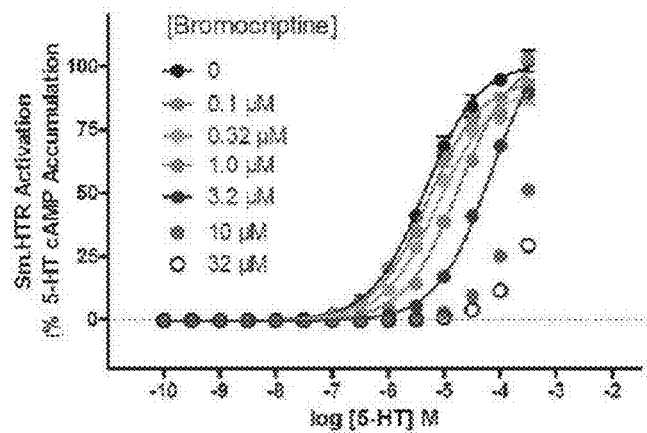
Figure 10C:
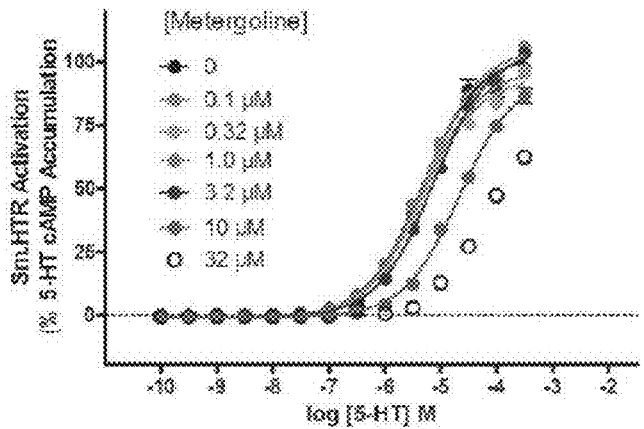
Figure 10D:
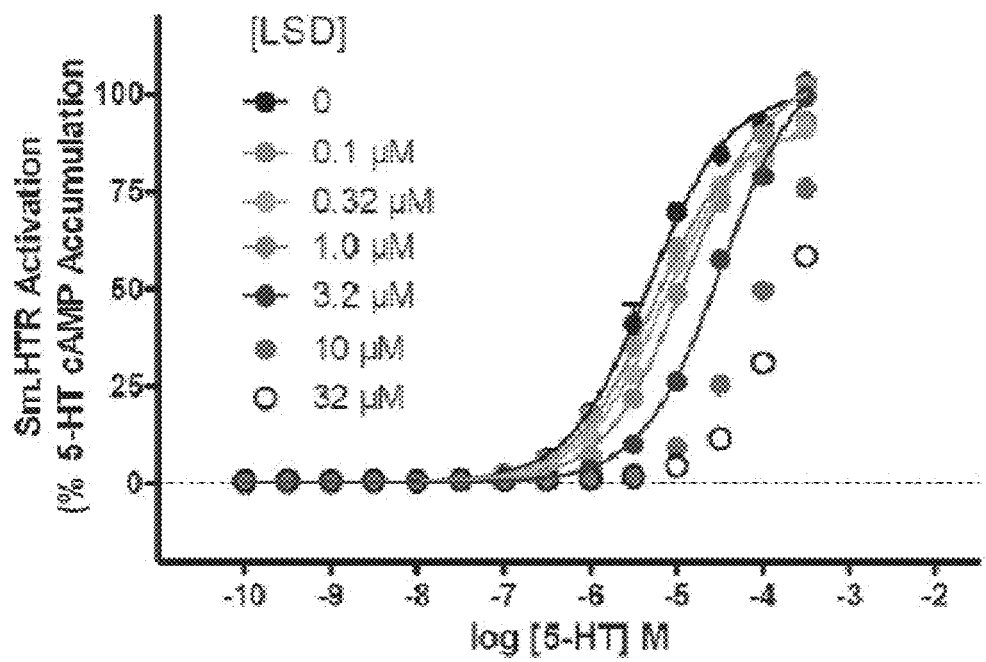
Figure 10E:
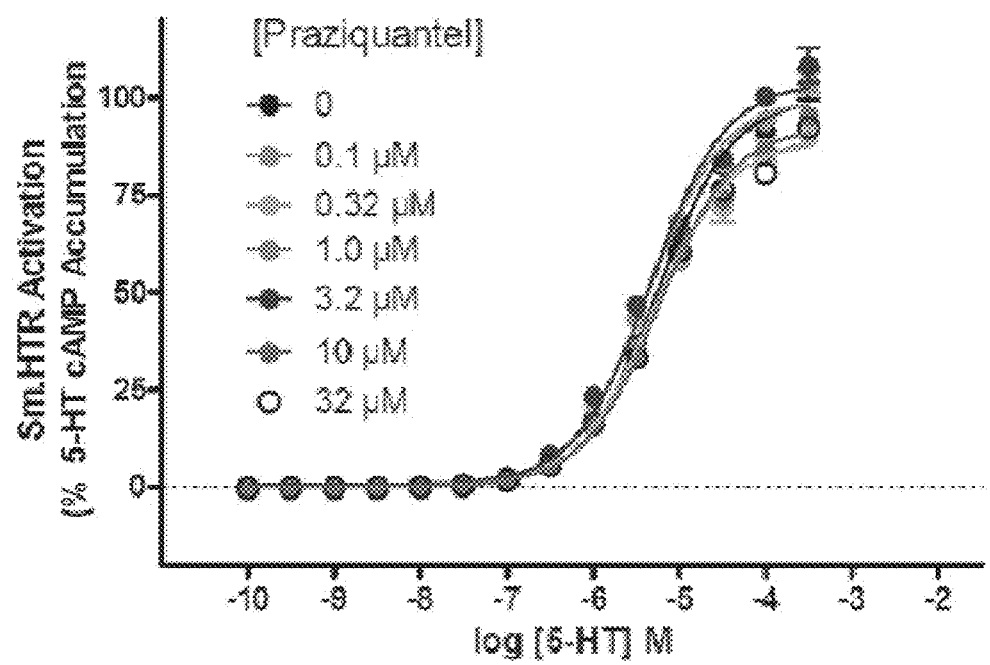
Figure 12A:
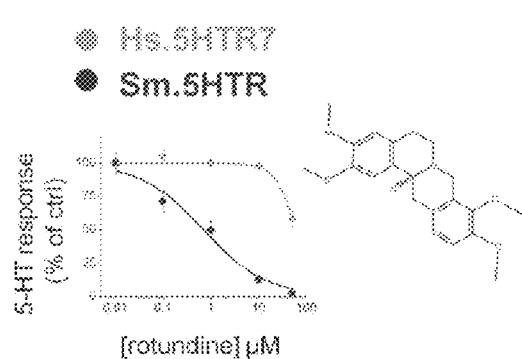
FIGS. 12A-12F. Effects of selected compounds on Sm.5HTR and Hs.5HT7R evoked cAMP generation, (A) inhibition curves shown for the following methoxy-isoquinoline related compounds against Sm.5HTR (blue) and Hs.5HTR7 (green): rotundine (data reproduced from FIG. 4A), (B) palmatine, (C) berberine and (D) tetrebenazine, (E) Comparison of 51-FIR selectivity between the tetrandrine and F berbamine, a structurally related compound.
Figure 12B:
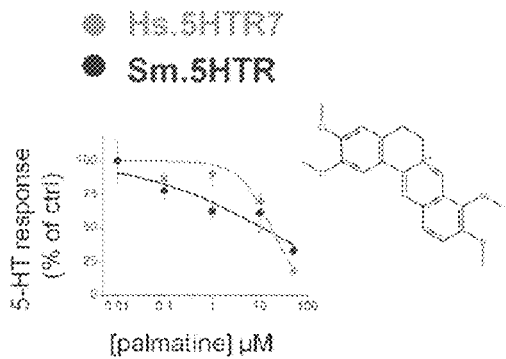
Figure 12C:
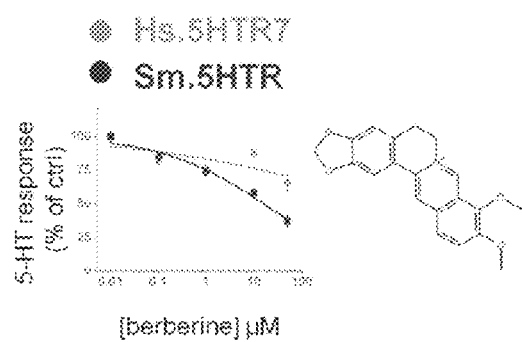
Figure 12D:
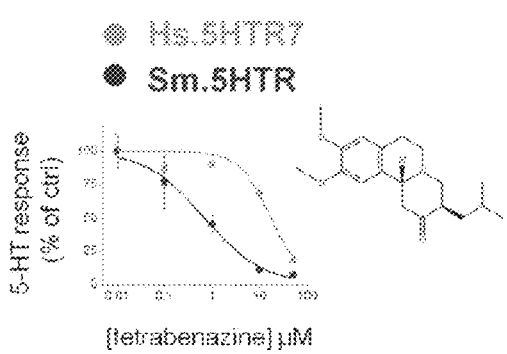
Figure 12E:
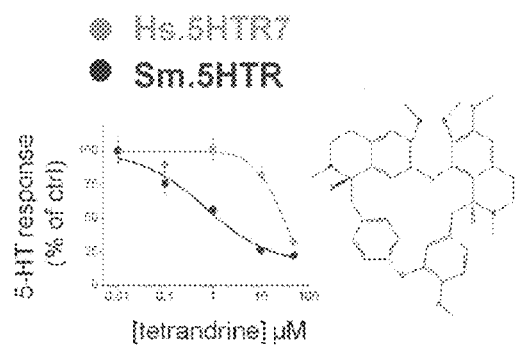
Figure 12F:
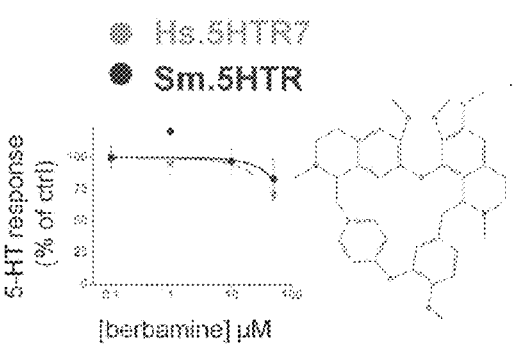

First, is Sm.5HTR activity modulated by ergot alkaloids? Several ergot alkaloids were screened against Sm.5HTR and these experiments revealed agonist activity of ergotamine and dihydroergotamine, which have previously been shown to stimulate the basal contractility of schistosomules (Chan et al., 2015). Ergotamine and dihydroergotamine were more potent ($EC_{50}$ of 232 nM and 315 nM, respectively) than 5-HT ($EC_{50}$ of about 1 µM, FIG. 10A), but with a lower maximal response suggestive of partial agonism. By contrast, other ergoline ligands, bromocriptine, metergoline and the hallucinogen lysergic acid diethylamide (LSD), an agonist at vertebrate $5-HT_{2A}$ receptors, exhibited no efficacy at Sm.5HTR (FIG. 10A). To investigate further the nature of these inactive ligands, the ability of increasing doses of bromocriptine (FIG. 10B), metergoline (FIG. 10C) and LSD (FIG. 10D) to modulate 5-HT evoked cAMP accumulation at the Sm.5HTR was assessed. Each of these ergot ligands caused a right-shift in the 5-HT dose-response relationship consistent with competitive antagonism (FIGS. 10B-D). At higher concentrations (>10 µM) bromocriptine and LSD showed almost complete inhibition of 5-HT evoked cAMP generation. To quantify the extent of antagonism, a Schild regression analysis (Arunlakshana and Schild, 1959; Kenakin, 1990) was performed which yielded affinity constants ($K_B$) of 410 nM for bromocriptine, 629 nM for LSD and 4530 nM for metergoline (FIG. 10F). These data show that ergot alkaloid derivatives can act as potent modulators of schistosome 5-HTRs.

Second, screening of PZQ against Sm.5HTR in this assay did not reveal any modulation of receptor activity over doses that would convey an antiparasitic effect (FIGS. 10A and E).

Third, to investigate the properties of antagonists at Sm.5HTR, the action of bromocriptine (a known 'irreversible antagonist' of Hs.5HTR7 (Knight et al., 2009) was compared with the competitive antagonist cyproheptadine. While both antagonists acutely inhibited Sm.5HTR function (FIG. 11A), inhibition evoked by bromocriptine persisted after antagonist wash-out while cyproheptadine inhibition was fully reversed by 1 hour after ligand removal (FIG. 11B). Expanding this assay to other ligands revealed long-lasting inhibition with several ligands previously established as pseudo-irreversible antagonists at Hs.5HT7R (methiothepin, bromocriptine, lisuride, risperidone and metergoline) but not with the competitive blockers clozapine and cyproheptadine (FIGS. 11C and D). The most potent ligands were bromocriptine, methiothepin and lisuride (FIG. 11E). Therefore, although ligand specificities of these GPCRs are divergent, a unique aspect of receptor phenomenology is conserved between the human and parasite receptor.

Finally, compounds structurally related to those compounds prioritized from the library were profiled screen in terms of parasite selectivity. As two of these top hits were dimethoxyisoquinoline derivatives (rotundine, alfuzosin), agents containing this moiety were analyzed. Slight modifications of rotundine structure were sufficient to alter the GPCR inhibition profile (FIG. 12), as reflected by comparison of berberine/palmatine (decreased potency and selectivity for Sm.5HTR) and tetrabenazine (selectivity for Sm.5HTR retained). Similarly, comparison of the closely related structures tetrandrine and berbamine suggested a discriminating structure-activity profile for Sm.5HTR (FIG. 12).

Figure 13:
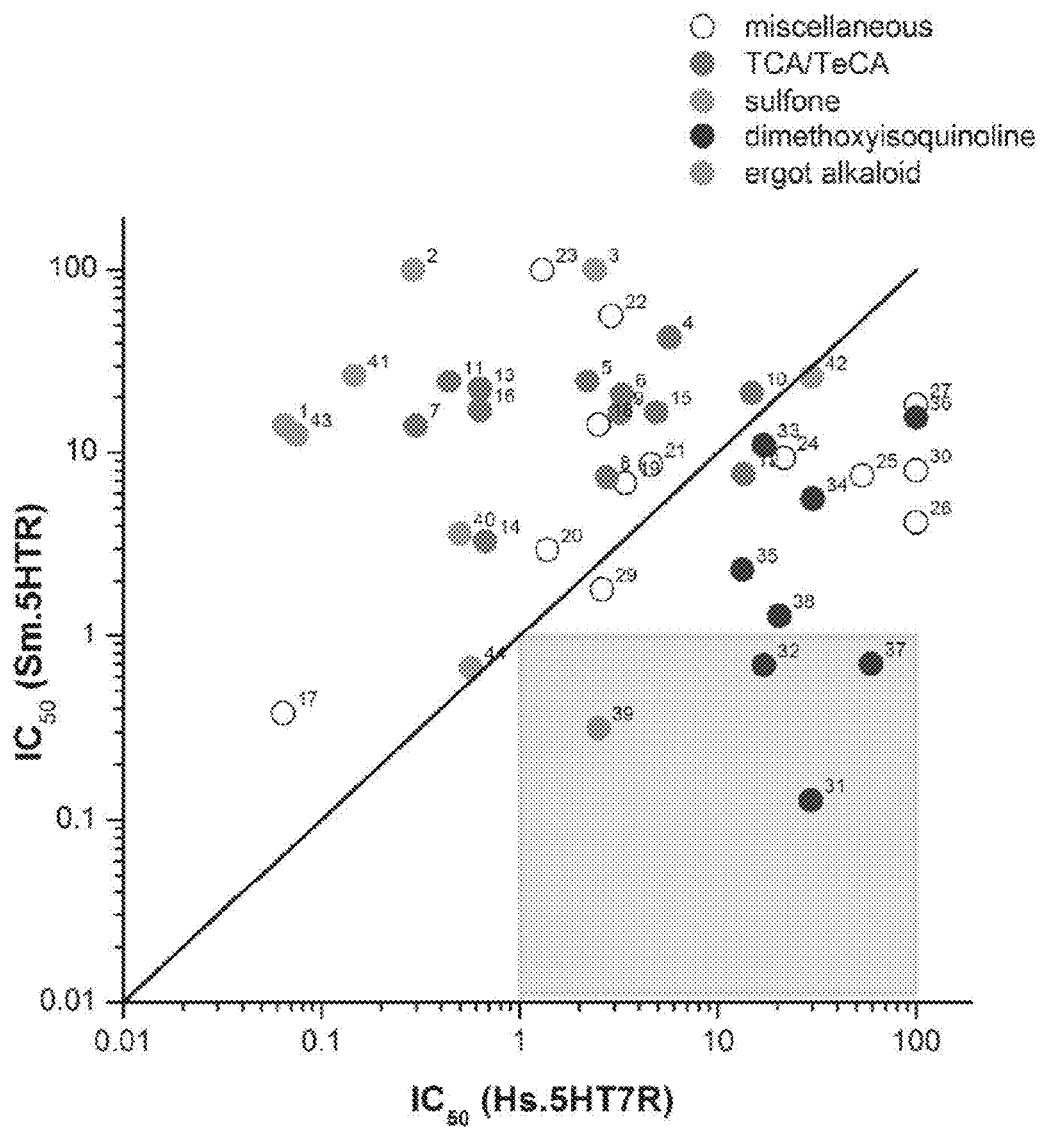
FIG. 13. Structure activity relationships for various drug classes against Hs.5HT7R and Sm.5HTR. Comparison of $IC_{50}$s for compounds inhibiting cAMP generation via Hs.5HT7R (abscissa) or Sm.5HTR (ordinate). Compounds with no preferential selectivity for either receptor, showing similar $IC_{50}$s, would cluster along the solid line. Hits in the lower right quadrant (red square) show sub-μM potency at Sm.5HTR but supra-μM potency at Hs.5HT7R. Four compounds meet this criterion (bromocriptine='39', rotundine='37', tetrandrine='31' and tetrabenazine='32'). Compound classes are indicated as follows: ergot alkaloids (green), isoquinolines (blue), tricyclic and tetracyclic antidepressants (magenta), sulfonyl compounds (orange), miscellaneous structures (open). Individual compounds are: 1, SB269970; 2, amisulpride; 3, SB742457; 4, olanzapine; 5, mianserin; 6, quetiapine; 7, clozapine; 8, cyproheptadine; 9, ketotifen; 10, loratadine; 11, maprotiline; 12, clomipramine.

Evaluation of structural data from all these assays provides insight to the structural selectivity between parasite and human receptors. FIG. 13 arrays worm $IC_{50}$ values versus human $IC_{50}$ values, such that compounds with sub-micromolar $IC_{50}$ values and selectivity for the parasite Sm.5HTR receptor fall into the bottom right quadrant. As expected, given the historical bias in ligand design for affinity toward human receptors, most compounds favor the human receptor (falling 'above the line' in FIG. 13). For example, most of the screened tricyclic and tetracyclic antidepressants show higher affinity for Hs.5HT7R (12/13 compounds screened). Similarly, ligands with phenyl-sulfonyl groups (SB 269970, SB742457) that are potent inhibitors of Hs.5HT7R (Lovell et al., 2000) (FIG. 7), completely lacked activity at Sm.5HTR. In contrast, compounds exhibiting potency and selectivity toward the parasite receptor (bottom right quadrant) were the ergot alkaloid bromocriptine and several dimethoxyisoquinoline compounds revealed by the experiments (rotundine, tetrabenazine, tetrandrine)

Effects of Compounds on Schistosomules.

Do these hits from the Sm.5HTR screen in vitro translate into effectiveness against parasites? To assess this issue, selected compounds were screened for effects on schistosomule contractility. Schistosomules exhibit a basal level of spontaneous contractile activity (FIG. 14A) which provides a simple phenotype for assaying neuromuscular activity. In this system, 5-HT is myoexcitatory: exogenous addition of 5-HT causes an increase in the basal contractile rate in a dose-dependent manner (FIG. 14B). Subsequent addition of the four compounds validated above as potent blockers of Sm.5HTR (rotundine, tetrabenazine, tetrandrine, bromocriptine) were examined. Three of these compounds—rotundine, tetrandrine and bromocriptine—all potently inhibited 5-HT evoked contractions ($IC_{50}$≤1 µM). Tetrabenazine was, however, less efficacious in vivo, effecting only about 50% inhibition of 5-HT evoked contractility at the highest dose (100 µM). Therefore, three of the four compounds prioritized by the Sm.5HTR screening data conferred an inhibitory action against schistosomules.

Figure 15A:
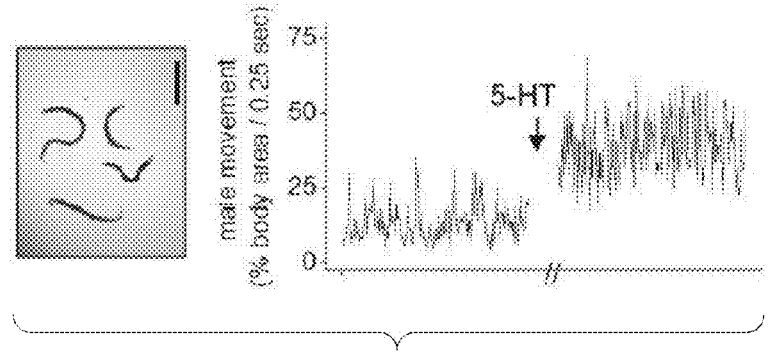
Figure 15B:
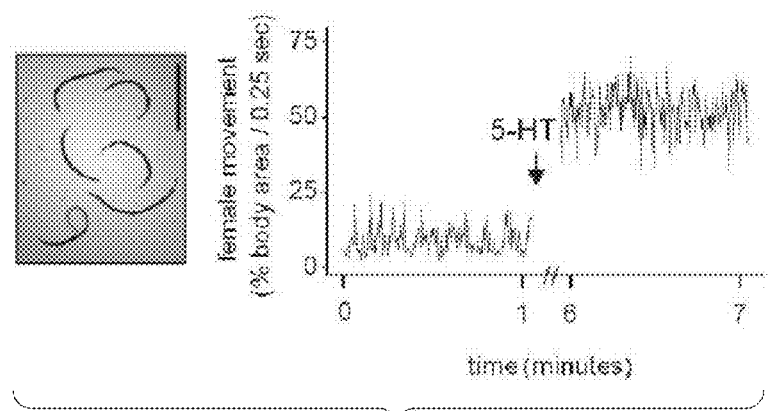
Figure 15C:
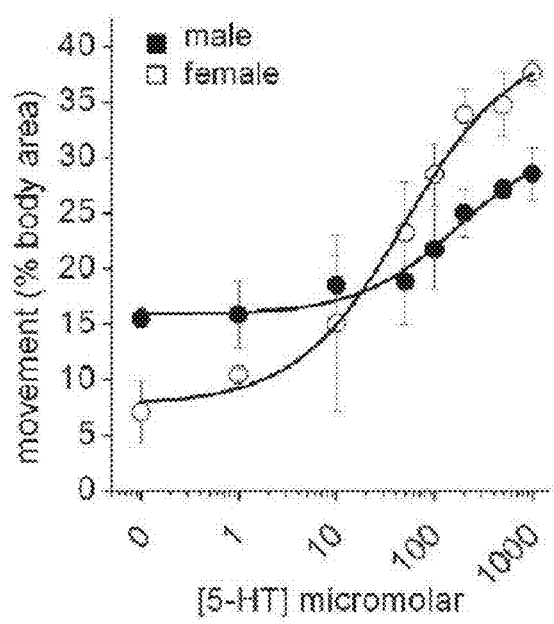
Figure 15D:
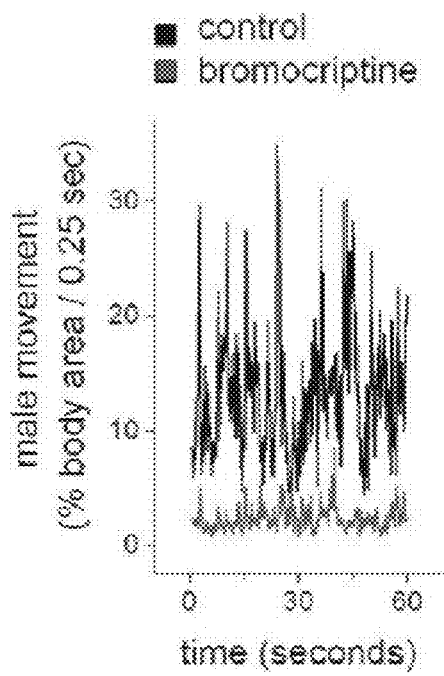
Figure 15E:
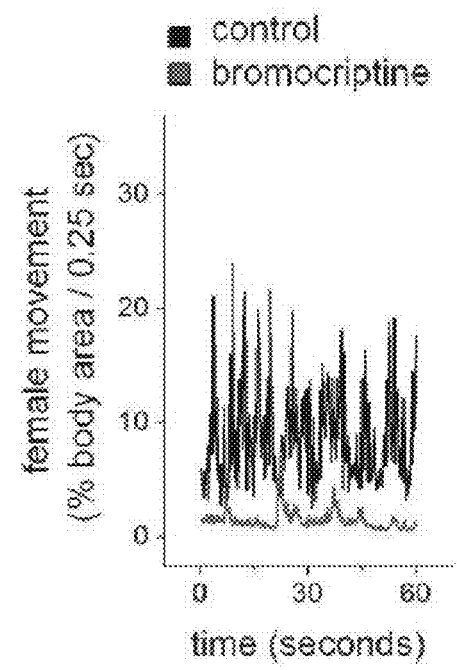
Figure 15F:
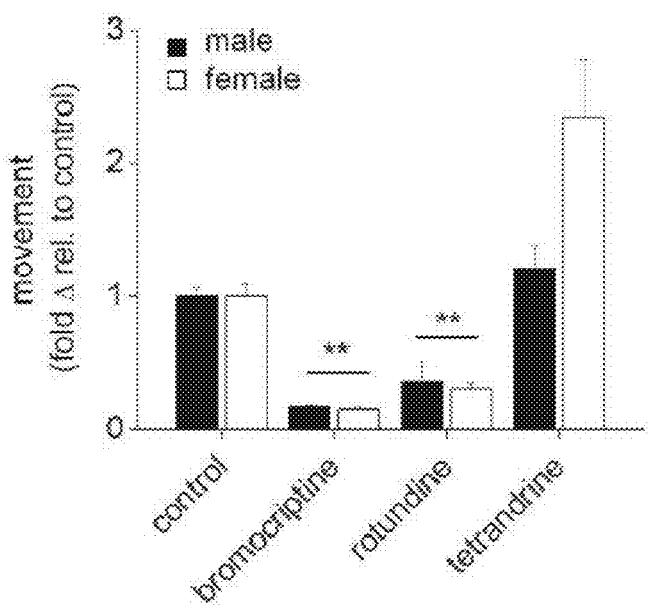
Figure 15G:
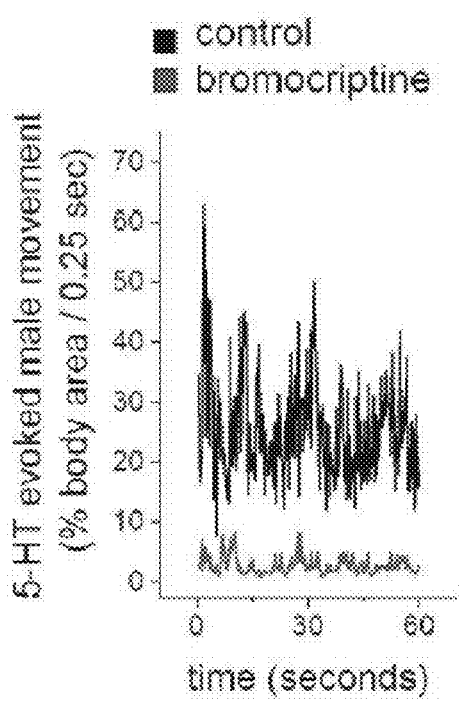
Figure 15H:
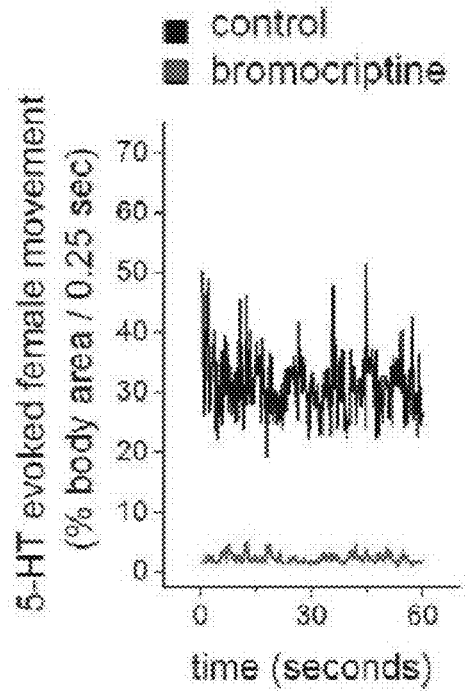
Figure 15I:
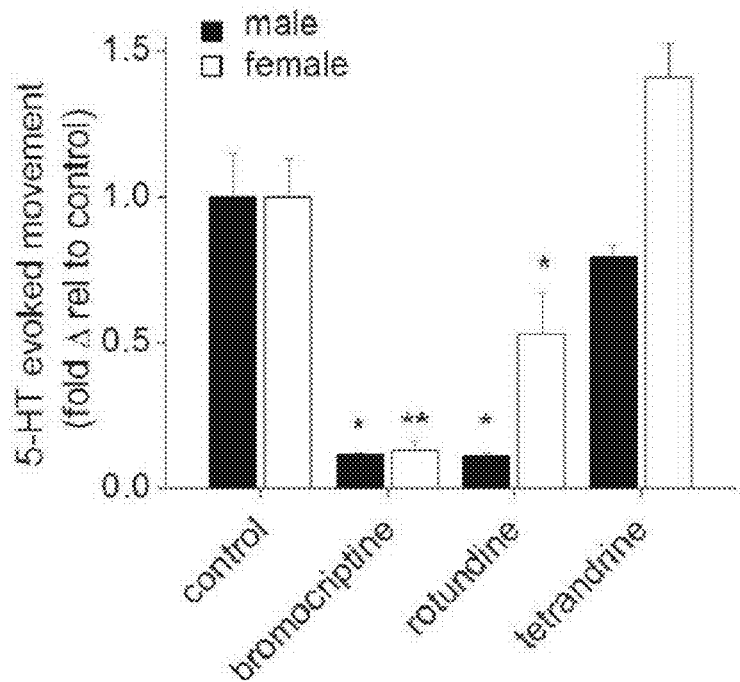

The action of Sm.5HTR ligands was then examined against adult schistosome worms in vitro. Isolated worms exhibited basal mobility, and application of 5-HT significantly increased the movement of unpaired male and female worms (FIG. 15A-B). Basal movement and the magnitude of the 5-HT evoked stimulation differed between males and females (FIG. 15A-B). These effects was quantified by performing dose-response relationships (FIG. 15C). Sex differences in the magnitude of 5-HT evoked cAMP generation (Kasschau et al., 1982), Sm.5HTR transcript and Sm.5HTR protein expression have previously been reported (Patocka et al., 2014; Anderson et al., 2015). The action of rotundine, tetrandrine and bromocriptine were then assessed against basal (FIGS. 15D-F) and 5-HT stimulated worm movement (FIGS. 15G-I). Addition of bromocriptine and rotundine markedly inhibited worm movements at rest whereas tetrandrine enhanced movements of isolated female worms (FIG. 15D-F). Bromocriptine and rotundine also inhibited the 5-HT evoked increases in worm movement, and again tetrandrine lacked an inhibitory effect (FIG. 15G-I). From these experiments, it was concluded bromocriptine and rotundine also act as effective paralytics of adult schistosome worms.

Finally, the kinetics of inhibition caused by bromocriptine and rotundine was examined to probe whether the protracted inhibition of Sm.5HTR observed in vitro (FIG. 11) was manifest in vivo. To do these experiments, worms were exposed to bromocriptine or rotundine, and then challenged with 5-HT at various points after drug removal. As expected both drugs inhibited basal worm movement, and blunted 5-HT evoked stimulation (FIG. 16). The time course of reversal of these effects was then examined. For male worms, which were effectively paralyzed by both drugs (FIG. 15D-F), the paralytic effects of rotundine were reversed within 3 hrs of drug exposure (FIG. 16A). However worms exposed to bromocriptine remained impaired for considerably longer, with recovery of movement being only demonstrable 24 hours after bromocriptine removal (FIG. 16A). A similar timecourse of recovery from bromocriptine exposure was also resolved for female worms (FIG. 16B). These data suggest that bromocriptine exposure evokes a protracted paralysis of adult schistosomes.

Time course of schistosome recovery from exposure to Sm.5HTR antagonists (black=DMSO control, blue=rotundine, red=bromocriptine). Mobility of worms was recorded following exposure to antagonist (10 µM, 'drug', 2 hour exposure) and addition of 5-HT (100 µM, 'drug+5-HT'). Media was then exchanged, and recordings were subsequently made on the same worms stimulated with 5-HT (100 µM) at the indicated timepoints (3, 6, 24 hours after drug washout). Data for males (A) and females (B) is presented normalized to basal movement of control (dorso) worms in the absence of 5-HT.

Discussion

In this study, a screen was employed to evidence the feasibility of pharmacological profiling a flatworm GPCR in HTS format. The assay system employed relied on an genetically encoded luminescent biosensor (Binkowski et al., 2011). This is an appealing approach as this strategy is non-destructive and affords the ability to continually monitor the kinetics of cAMP generation from a single sample. Further, by directly reporting cAMP levels, rather than transcriptional outcomes (e.g., cAMP reporter genes), this approach also reveals proximal receptor activity in real time to help discern how specific compounds are modulating GPCR activity. Acceptable Z' scores were reliably obtained in 384 well format (FIG. 3), and the sensitivity of this approach has permitted responses from endogenous GPCRs to be resolved even in ultra-high throughput screening formats (3456-well plates). Obviously, this particular biosensor is suited only for $G_s$ and $G_i$-coupled GPCRs, but the optimization of other biosensors—for example, genetically-encoded $Ca^{2+}$ indicators (Akerboom et al., 2013), or reporters that are agonist independent (Kroeze et al., 2015)—should aid HTS profiling of other flatworm CiPCRs coupling to different second messenger cascades.

Differences Between Human and Schistosome 5-HT7 Receptors.

The importance of unbiased profiling of flatworm GPCR targets is underscored by visualization of the entire dataset (FIG. 5E) that underscores a divergence in ligand specificities between the schistosome 5-HT receptor (Sm.5HTR) and the closest human homolog (Hs.5HT7R, about 30% amino acid identity). This divergence in ligand specificity evidences concerns over use of established mammalian ligands to infer flatworm physiological mechanisms as many chemical probes used to study human $5HT_7$ receptors have modest effects on Sm.5HTR at similar concentrations. Examples include the sulfonyl derivatives SB269970, SB742457 and amisulpiride (FIG. 7). The fact that 5-HT receptors in different organisms have evolved divergent characteristics profiles is of course unsurprising: the adult schistosome lives within the human host circulatory system, a 5-HT rich environment, where it continuously ingests and cycles 5-HT replete cells. The characteristics of the ligand binding site of Sm.5HTR may therefore necessitate adaptations to this niche. While this pharmacological divergence may limit repurposing efforts for existing serotonergic ligands that have been optimized toward human usage, it is nevertheless encouraging for de novo ligand discovery if pharmacological differences between flatworm and human receptors can be exploited to selectivity target parasite biology.

In this regard, the data identified several ligands were identified with a preference for Sm.5HTR over Hs.5HT7R, and reciprocally several ligand classes were deprioritized owing to an observed preferential selectivity for the human receptor ('above the line' in FIG. 15B). These latter groupings included the sulfonyl derivatives discussed above, as well as tricyclic and tetracyclic antidepressants which have previously been shown to cause schistosomule hyperactivity (Abdulla et al., 2009), likely through inhibition of monoamine transporters (Patocka and Ribeiro, 2013). Although features of these drugs that convey potency in schistosomules have been identified (Abdulla et al., 2009), these features do not necessarily convey selectivity (over Hs.5HT7R, or human 5-HT transporters). A similar case could be made for many ergot alkaloids, with the noted exception of bromocriptine, which was the only ergot screened to date exhibiting higher selectivity (about 10-fold) for the parasitic 5-FIT receptor (FIG. 15). Bromocriptine had been shown to displace $^3$H-dopamine in planarian binding assays (Chan et al., 2014), but clearly bromocriptine also possess potent anti-serotonergic properties in flatworms consistent with the polypharmacology of ergot alkaloids. The antagonist effect of LSD against Sm.5HTR (FIG. 5B) was also unexpected, given LSD action as a serotonergic agonist in mammals. Further attention is needed to identify features of the ergoline scaffold that convey preferential modulation of parasitic 5-HTRs, given the about 100-fold range in $IC_{50}s$ observed (FIG. 13).

Figure 7B:
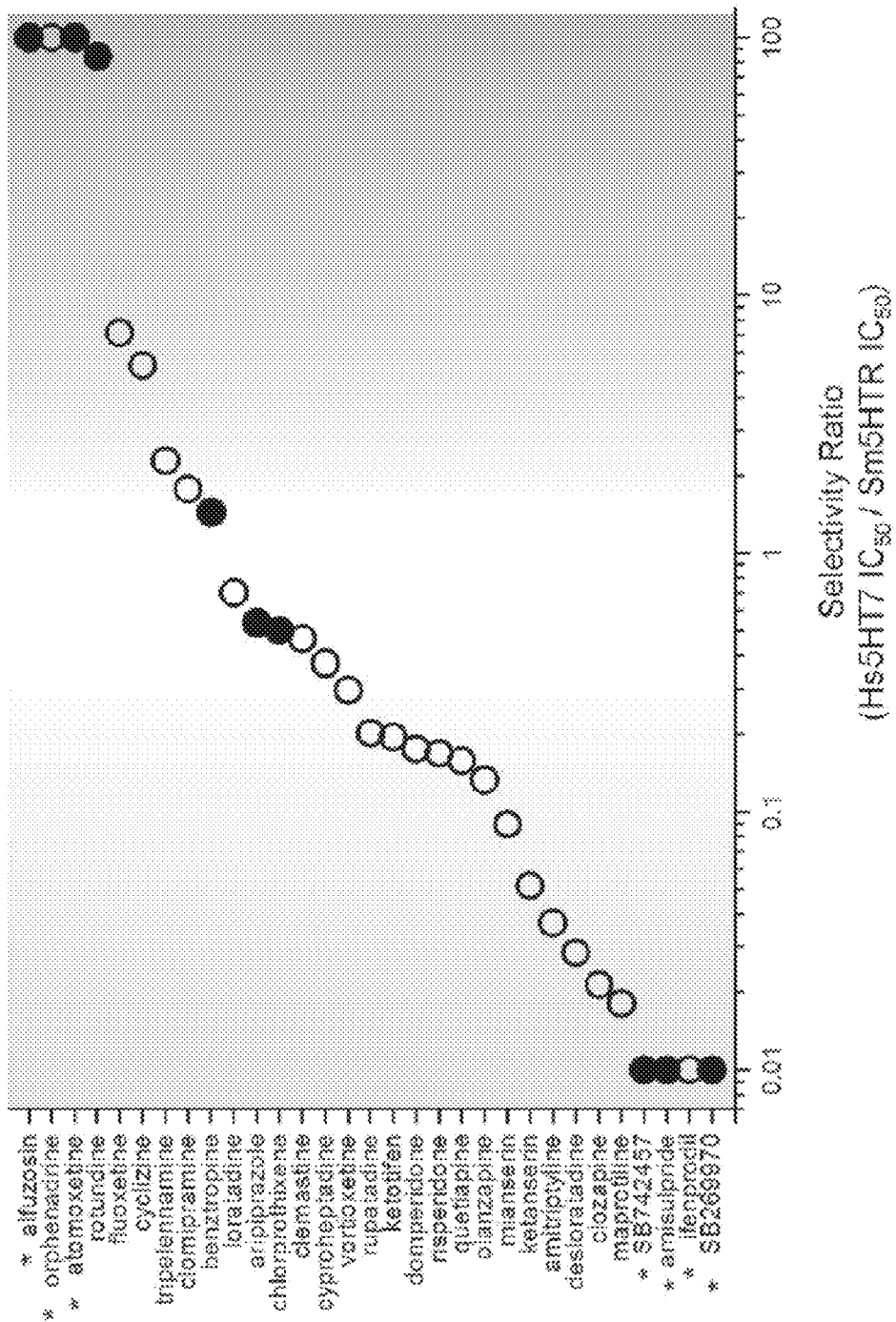

In contrast to the observed human bias of many ligands, several compounds with preferential selectivity toward Sm.5HTR were resolved (FIGS. 7B and 6B). First, several modulators of biogenic amine transport, represented by compounds such as atomoxetine and fluoxetine. Fluoxetine is a serotonin reuptake inhibitor while atomoxetine, a non-halogenated derivative of fluoxetine, is employed as a norepinephrine transporter inhibitor. Compounds of this class are known to block 5-HT GPCRs (Ni et al., 1997). Second, and perhaps most striking, were ligands containing dimethoxyisoquinoline moieties (blue, FIG. 13), several of which exhibited clear bias toward Sm.5HTR. These included two compounds with prior precedent as bioaminergic blockers—alfuzosin, a mammalian adrenergic ($\alpha$1) blocker, and rotundine which inhibits dopamine and serotonin binding at D1, D2 and $5-HT_{1A}$ GPCRs (Wang and Mantsch, 2012). Rotundine potently inhibited Sm.5HTR ($IC_{50}$ about 700 nM) while lacking any effect on Hs.5HT7 at concentrations up to 50 µM. The stalwart anthelmintic PZQ is also a isoquinoline derivative, although direct interrogation of PZQ against Sm.5HTR did not yield any effect (FIGS. 10A and E). This does not preclude the possibility that PZQ acts as a ligand at another flatworm bioaminergic GPCR (Witchley et al., 2013), one explanation for the functional antagonism observed between PZQ and 5-HT in planarians (Chan et al., 2015), schistosomules (Chan et al., 2015) and adult schistosomes (Willcockson and Hillman, 1984; Harder et al., 1987).

Subsequent screening of bromocriptine (the most parasite selective ergot alkaloid, FIG. 13), and the three promising isoquinoline 'hits' against both schistosomules and adult worms (FIGS. 14 and 15) revealed a clear inhibition of 5-HT evoked hypermotility from two of the four compounds (bromocriptine, rotundine) prioritized from the screen of heterologously expressed Sm.5HTR. The two other Sm.5HTR ligands (tetrabenazine, tetrandrine) were less effective. Such attrition of leads is expected when advancing candidates identified in vitro. For example, the stimulatory action of tetrandrine against adult worms (FIG. 15), not observed in the schistosomule dataset (FIG. 14), may reflect a counteracting stimulatory action at other schistosome GPCRs upregulated at the adult stage. Differences in GPCR expression (Anderson et al., 2015) may also contribute to the observed differences in drug and 5-HT action between male and female worms (FIG. 15). Overall, this was an encouraging translation from in vitro data to activity against different parasite life cycle stages, supporting the rational design and development of antiparasitic drugs aimed at schistosomal GPCRs.

Similarities Between Human and Schistosome 5-HT7 Receptors.

Despite the divergence in pharmacological selectivity between the human and schistosome 5-HT GPCRs, it is worthwhile highlighting an important similarity between these receptors which may prove a boon for anthelmintic development. The human Hs.5HT7R is induced into a prolonged inactivated state by exposure to a subset of ligands, termed 'inactivating antagonists' (Smith et al., 2006; Knight et al., 2009). These inactivating antagonists are structurally diverse and include the ergot alkaloid bromocriptine risperidone, methiothepin, lisuride and metergoline (Knight et al., 2009). Application of these ligands caused a prolonged inactivation of Hs.5HT7R activity in heterologous expression systems or in assays on endogenous receptors (Smith et al., 2006; Knight et al., 2009; Smith et al., 2011). Data suggests this aspect of receptor phenomenology may be conserved with Sm.5HTR, the most abundant deorphanized GPCR in adult schistosome worms, when evaluated in receptor level (FIG. 11) and whole organism assays (FIG. 16). The predominant expression of this specific GPCR in this organism, together with conservation of this receptor property, provides a clearly targetable weakness for anthelmintic development. If transient exposure to an inactivating antagonist inhibits parasite mobility well beyond the pharmacokinetic persistence of the drug within an infected individual, this would be clearly be effective for antiparasitic action and serve to minimize dosing requirements in challenging healthcare environments. Sm.5HTR is also expressed at multiple life cycle stages, and is conserved in other PZQ-sensitive parasites. Further exploration of this property and identification of parasitic-selective ligands that convey this effect are warranted, and such activities will be facilitated by the approaches optimized in this study.

In conclusion, these data demonstrate the optimization and application of a real-time biosensor assay for interrogating flatworm GPCRs in vitro, which is capable of scaling to HTS. Application of this approach to profile Sm.5HTR revealed parasitic-selective ligands and ligand series, as well as conservation of a ligand-evoked inactivation mechanism at the most predominantly expressed S. mansoni 5HTR.

Example 2

Materials and Methods
Molecular Cloning.

The sequence for Sm.5HTR (GenBank accession KX150867, PMID: 27187180) was used to BLAST the S. haematobium and S. japonicum genomes for putative homologs. The resulting S. haematobium (NCBI Reference Sequence XM_012944163 and XM_012944164) and S. japonicum (GenBank FN332592.1) hits were used as templates to clone out full length mRNA sequences by 5' and 3' RACE (Marathon cDNA Amplification Kit, Clontech) using S. haematobium and S. japonicum total RNA provided by the Schistosomiasis Resource Center. Plasmids for heterologous expression were generated by codon optimizing the coding sequence of each receptor for mammalian expression and subcloning into pcDNA3.1(−) between NotI and EcoRI and into pEGFP-N3 at EcoRI.

Cell Culture.

HEK293 cells (ATCC CRL-1573.3) were cultured in growth media consisting of DMEM supplemented with GlutaMAX (Gibco cat #10566016)+10% heat inactivated fetal bovine serum and penicillin-streptomycin (100 units/mL, ThermoFisher). Stable cell lines for the pGloSensor-22F cAMP Plasmid (Promega) and schistosome 5HTRs in pcDNA3.1(−) were selected with hygromycin (200 µg/mL) and G418 (400 µg/mL). The correct identity of each stably expressed sequence was verified by isolating total RNA from each stable line (TRIzol Reagent, Ambion) and amplifying the sequence of interest with gene specific primers flanking the 5' and 3' regions of the cds (SuperScript® III One-Step RT-PCR System, Invitrogen). PCR products were ligated into a TA cloning vector (pGEM-T Easy, Promega) and sequenced.

cAMP Luminescence Assays.

HEK293 lines stably expressing both the 22F cAMP sensor and Sm.5HTR were cultured in growth media supplemented with 10% dialyzed FBS. For cAMP assays in 96 well format, cells cultured in T-75 flasks were trypsinized (TrypLE Express, Gibco) and plated in solid white 96 well plates (Costar cat #3917) the day prior to assay at a density of $2.5 \times 10^4$ cells/well. The following day media was removed and replaced with assay buffer consisting of HBSS buffered with HEPES (20 mM, pH 7.4)+BSA (0.1% w/v) and D-luciferin sodium salt (1 mg/mL, Gold Biotechnology). Plates were equilibrated at room temperature for 1 hour, at which point 3-Isobutyl-1-methylxanthine (IBMX 200 µM, Sigma Aldrich) was added. Plates were equilibrated a further 30 minutes prior to test compound addition. Test compounds were added and luminescence was read for 45 minutes on a GloMax®-Multi Detection System plate reader (Promega) to screen for agonists, after which plates were removed, 5-HT was added to each well (500 nM), and plates were read a second time to screen for antagonist activity. Readings performed in 384 well format were modified so that cells were assayed in suspension. Cells were grown to 70% confluence in T-75 flasks, trypsinized and pelleted (300 RCF×5 minutes). Media was removed and cells were resuspended in 25 mL assay buffer supplemented with IBMX (200 µM). A 96 channel semi-automated pipet (Eppendorf epMotion 96) delivered 55 µL of cell suspension per well (5000 cells/well) into solid white 384 plates (Corning 3574). After one hour of equilibration, compounds were added and luminescence was read on a Tecan Infinite M1000 PRO Microplate Reader, with one 45 minute read for agonists followed by 5-HT addition and a second 45 minute read for antagonists.

Compound Sourcing.

The following compounds were sourced from Sigma Aldrich: praziquantel (P4668-1G), ergotamine tartrate (1241506-150MG), dihydroergotamine tartrate (D1952000), bromocriptine (B2134-100MG). Nuciferine was sourced from Cerilliant (PHY83282). Lisuride maleate (4052), dihydroergotoxine mesylate (0474) and methylergometrine maleate (0549) were sourced from Tocris. LSD and BOL-148 were sourced from the National Institute on Drug Abuse (NIDA).

In Vitro Schistosome Assays.

Female Swiss Webster mice infected with *S. mansoni* cerceria (NMRI strain) were sacrificed 49 days post infection by $CO_2$ euthanasia. Adult schistosomes were recovered by perfusion with a solution of 0.85% sodium chloride+0.75% sodium citrate and dissection of the mesenteric vasculature. Harvested schistosomes were washed in RPMI 1640 Medium with GlutaMAX+5% heat inactivated FBS (Gibco) and Penicillin-Streptomycin (final concentration 100 units/mL, ThermoFisher cat #15140122).

For movement assays, worms were cultured 37° C./5% $CO_2$ in vented 100×25 mm petri dishes (ThermoFisher cat #4031) containing 50 mL of media and used between 1-3 days after harvesting. Prior to assessing worm movement, individuals were transferred to a six well dish (4-5 individuals per well) containing 3 mL drug solution in RPMI 1640 supplemented with HEPES (25 mM) and MS (5%). Videos were recorded using a Zeiss Discovery v20 stereomicroscope and a QiCAM 12-bit cooled color CCD camera controlled by metamorph imaging software (version 7.8.1.0). 1 minute recordings were acquired at 4 frames per second, saved as a .TIFF stack, and movement was analyzed using ImageJ software as described in (PMID: 27187180, PMID: 27397763).

For egg laying assays, adult schistosomes were transferred to 24 well plates the day after harvesting from mice (5 worm pairs in 2 mL media per well). Eggs were counted under a stereomicroscope daily, after which worms were transferred to a new well with fresh drug containing media. Egg counts were recorded for five days, and data processed as the mean number of eggs laid per worm pair/day. Measurements of egg dimensions were quantified using the "analyze>measure" function in ImageJ to record the length and width of individual eggs.

In Vivo *Schistosoma mansoni* Screening.

Female Swiss Webster mice were exposed to 200 *S. mansoni* cerceria (NMRI strain) at between 4-6 weeks old. For hepatic shift assays, infections were allowed to mature to 7 weeks, at which point mice were given test compounds by intraperitoneal injection and euthanized 4 hours later. Compounds were solubilized in 50 µL DMSO, and diluted in 200 µL 5% w/v trappsol (Cyclodextrin Technologies Development, THPB-p-31 g)+saline (NaCl 0.9%) solution. Immediately after being euthanized, mice were dissected to remove the liver from the portal vein, and the number of worms recovered from the portal vein, mesenteries and liver was recorded for each mouse.

Assays testing the curative efficacy of compounds against schistosome infection were performed on mice 6 weeks after exposure to cerceria. Drugs were dosed as follows. Ergotamine (95 mg/kg) was solubilized in 50 µL DMSO and diluted in 200 µL trappsol-saline and delivered by intraperitoneal injection twice a day for one week. Praziquantel (50 mg/kg) was similarly solubilized and injected intraperitoneally once a day for one week. The negative control cohort was given twice daily injections of DMSO (50 µL) added to 200 µL trappsol-saline solution. Mice were weighed and euthanized at 49 days post infection. Worms were harvested and counted as in the hepatic shift assay. Spleen and livers were weighed, and a segment of intestine was excised from the most distal region of the rectum to 10 cm above the cecum. The small and large intestines were separated by cutting immediately above and below the cecum. Each was cut lengthwise to expose the lumen and thoroughly washed in NaCl (1.2%) to remove excrement. Intestines were laid flat with the intestinal mucosa facing upwards and clamped between two glass plates to allow visual inspection of eggs using a stereo microscope.

Results

Ergot Alkaloid Structure Activity Relationship at *S. mansoni* 5-HT Receptors

Ergot alkaloids display a range of properties against Sm.5HTR, ranging from full agonism to potent antagonism (FIG. 18A). Two chemical series were studied in detail—the ergopeptines (FIG. 18B) and the lysergic acid amides (FIG. 18C).

The ergopeptine ergotamine acted as a full agonist (Sm.5HTR $E_{max}$ 95±5% of 5-HT, $EC_{50}$ 43±13 nM). The dehydrogenated derivative dihydroergotamine, which is identical to ergotamine except for the reduction of a saturated bond on the ergoline ring (D9-10), was also a potent full agonist (Sm.5HTR $E_{max}$ 103±11% of 5-HT, FIG. 18B). However, compounds with modifications to the R1 group of the amino acid ring system exhibit reduced agonist activity. This is evidenced by replacement of the carbonyl group with an isopropyl group in dihydroergotoxine (Sm.5HTR $E_{max}$ 19±2% of 5-HT) and its constituents dihydroergocristine (Sm.5HTR $E_{max}$ 22±2% of 5-HT) and α-ergocryptine (negligible activity, FIG. 18B). Modifications to the R2 group of these ergopeptines proved important for antagonist activity—dihydroergocristine is an antagonist and possesses a methylphenyl R2. Switching the R2 modification to an isopropyl group, as in α-ergocryptine, results in a loss of antagonist activity. However, the when the inactive α-ergocryptine is modified by bromination of the ergoline ring at the B2 position (bromocriptine), it becomes an effective antagonist ($IC_{50}$ 1.6±0.4 µM).

A similar variation in efficacy depending on amide or ergoline modifications is seen within the lysergic amide series (FIG. 18C). Lysergic acid diethylamide (LSD) acts as a potent partial agonist at Sm.5HTR (Emax 40±26% of 5-HT, $EC_{50}$ 250±150 nM). Modifications of the amide group are capable of altering this profile. For example, replacing the diethylamide groups with one methyl and one propyl group resulted in a reduction of efficacy (lysergic acid methyl propyl amide, LAMPA). Further alterations, as seen with ergometrine and methylergometrine confer an increase in agonist activity (Sm.5HTR $E_{max}$ of 61±4% and 50±17% of 5-HT, respectively). In all three cases, modification of the diethylamide resulted in reduced potency (FIG. 18C), consistent with the effects of similar LSD modifications on mammalian receptors Nichols et al., 1996; Wacker et al., 2017). The impact of modifications to the stereochemistry of the amide group can also be assessed by comparing lisuride and LSD, both of these compounds are potent partial agonists with approximately equivalent efficacy (respective $E_{maxs}$ 59±25% and 40±25% of 5-HT). Modifications to lisuride and LSD also provide a reference for assessing modifications to the ergoline ring system. Terguride differs from lisuride due to hydrogenation of the D9-10 double bond, and this single modification completely eliminates agonist activity while retaining potent antagonist properties (lisuride Sm.5HTR $IC_{50}$=180±270 nM, terguride $IC_{50}$=400±50 nM). Notably, this same hydrogenation differentiating the ergopeptines ergotamine and dihydroergotamine had no effect—possibly due to ergopeptines possessing larger tetracyclic structures corning off of the nearby amide group. On the other hand, bromination of the ergoline B2 position confers the same effect with lysergic acid amdes (creating 2-bromo-lyseric acid diethylamide (BOL-148) from LSD) as with ergopeptines. Agonist activity is eliminated, and BOL-148 is the most potent antagonist identified at Sm.5HTR ($IC_{50}$ 100±20 nM).

Validation of Sm.5HTR Ligands In Vitro

Mobility Assays. The most potent agonist and antagonist hits identified at Sm.5HTR were screened on adult *S. mansoni*. Since the movement of schistosome parasites is Sm.5HTR-dependent, observing the effects of ligands on the movement of cultured worms provides a read-out of efficacy at Sm.5HTR ex vivo (Patocka et al., 2014) (FIG. 19A) and predictive value of anthelmintic activity in vivo.

Screening agonist hits identified in cell-based assays on adult *S. mansoni* confirmed that Sm.5HTR agonists phenocopy serotonin, stimulating parasite movement, while Sm.5HTR antagonists block serotonin. Ergot alkaloid agonists stimulated movement at concentrations several logs more potent than tryptamine agonists (e.g., ergotamine $EC_{50}$=10±3 nM verses 5-HT $EC_{50}$=52±2 μM, FIG. 19B). The efficacy of Sm.5HTR antagonists were assessed by exposing adult schistosomes to drug prior to addition of a maximal concentration of serotonin (200 μM). The ergoline antagonists with the 2-bromo ergoline modification (BOL-148 and bromocriptine) potently inhibited schistosome movement, with respective $IC_{50}$s of 29±23 nM and 251±67 nM (FIG. 19C).

Egg Laying.

In addition to regulating parasite movement, serotonin has an important role in flatworm metabolism (Mansour, 1979; Mansour, 1984; Rahman et al., 1985; 975). The intramammalian adult schistosome can generate the necessary ATP required for survival through glycolysis (Schiller et al., 1975). However, egg production ceases under anaerobic conditions, requiring oxidative phosphorylation (Huang et al., 2012; Pearce et al., 2015; Bueding et al., 1.982). Given that exogenous serotonin increases glucose consumption through glycolysis (Mansour, 1984; Bueding et al., 1982), it was tested whether Sm.5HTR ligands may influence egg production.

In order to assess the effect of Sm.5HTR ligands on egg production, male and female pairs of adult schistosomes were co-cultured in the presence of various compounds and eggs laid in vitro were quantified daily (FIG. 19D-E). Serotonin (100 μM) decreased egg laying by 83% (FIG. 19F). Forskolin (100 μM) also inhibited egg laying by 62%, consistent with serotonin's effects being mediated through cAMP (Kasschau et al., 1982). Parasites were also incubated with the Sm.5HTR ligands that proved most potent in mobility assays. Antagonists (nuciferine, BOL-148) had no effect on egg laying. Nor did the partial agonist LSD, despite being screened at 10 μM—a concentration well above its $EC_{50}$ in cell based. assays and mobility assays. However, exposure to the full agonist ergotamine reduced egg laying 54%, and this effect was dose dependent (FIGS. 19F&G).

Figure 19I:
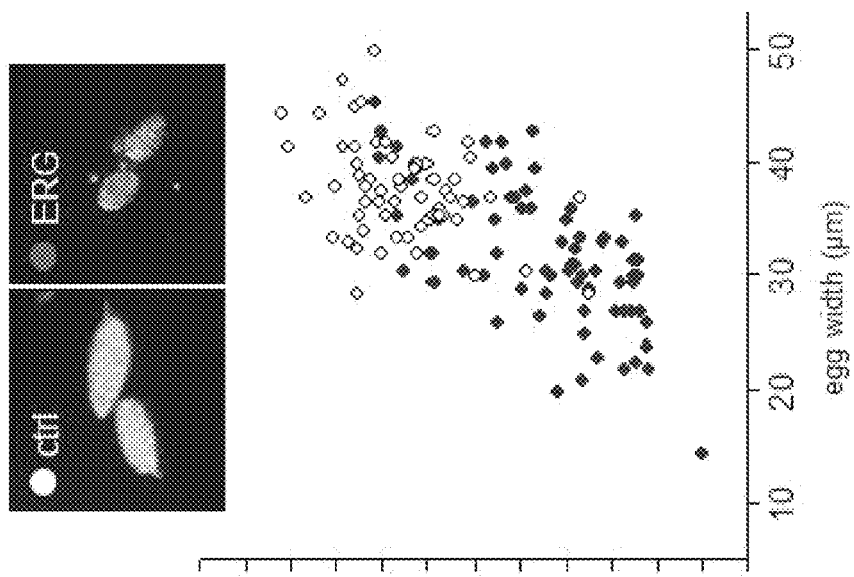
Figure 19H:
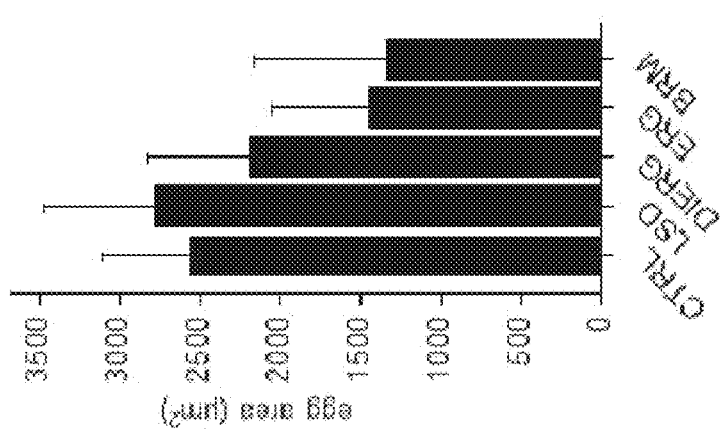

Finally, ergotamine not only reduced the number of eggs laid, but treatment also resulted in aberrant morphology of the eggs that were produced (43% reduction in size, FIGS. 19H&I).

Validation of Sm.5HTR Ligands In Vivo

Acute Effects—Hepatic Shift Assay.

Several experiments using a murine model of schistosomiasis were carried out in order to test the anthelmintic efficacy of Sm.5HTR ligands in vivo. First, the acute effect of drugs were assessed using a "heptic-shift" assay; mature parasites normally reside within the mesenteric vasculature, and upon exposure to anthelmintics they dislodge and are swept to the liver[12,13] where they may be cleared from the host[14] (FIG. 20B-F).

Given that the current anthelmintic therapy, praziquantel, disrupts worms and results in a rapid shift from the mesenteric vasculature to the liver (Melhorn et al., 1981) (FIG. 20B-F), it was hypothesized that Sm.5HTR ligands that disrupt parasite movement would cause a similar hepatic shift. Compounds were delivered by intraperitoneal injection and mice were euthanized three hours later in order to quantify the number of worms found in the mesentaries, portal vein or liver. The Sm.5HTR agonist ergotamine produced a hepatic shift comparable to the current anthelmintic praziquantel (75.1±1.6.9% vs. 68.8±14.1% of worm burden found in the liver, respectively). The effects of partial agonists were more variable-methylergometrine treatment resulted in 50.6±28.5% of worms being found in the liver, while lisuride and dihydroergotoxine treatment showed no difference relative to control animals (FIG. 20B-F).

Efficacy Against Schistosomiasis Infection

On the basis of these results, infected mice with Sm.5HTR ligands were treated to assess whether they are capable of ameliorating schistosomiasis in vivo. Ergotamine was prioritized given its efficacy in vitro (stimulating movement with an $EC_{50}$>1000× more potent than 5-HT and disrupting egg laying) and ability to cause an acute hepatic shift in vivo. Mice were injected with vehicle control (dmso), the current frontline anthelmintic (praziquantel) or ergotamine twice daily for one week at starting 42 days post infection.

Figure 20A:
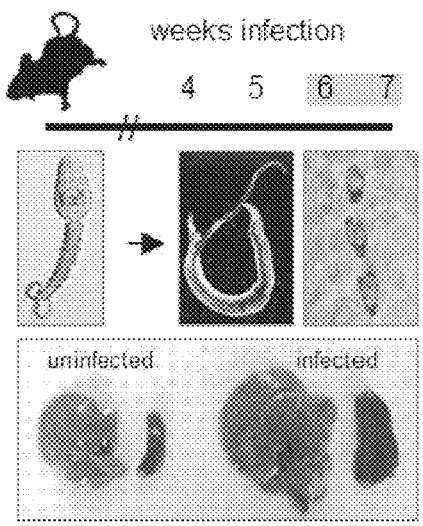
Figure 20B:
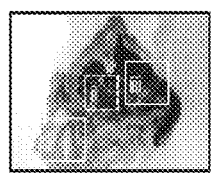
Figure 20C:
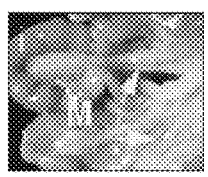
Figure 20D:
Figure 20E:
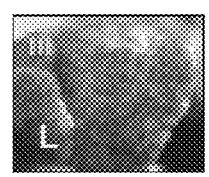
Figure 20F:
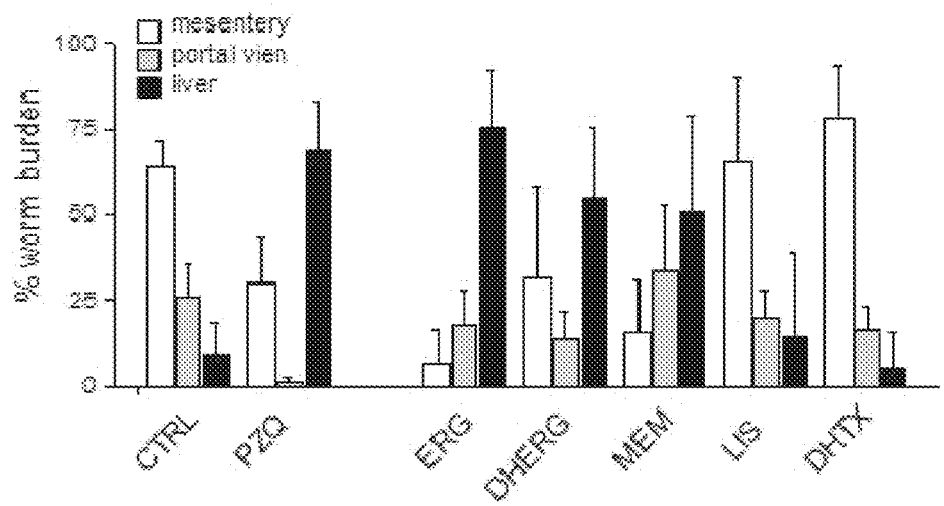
Figure 20K:
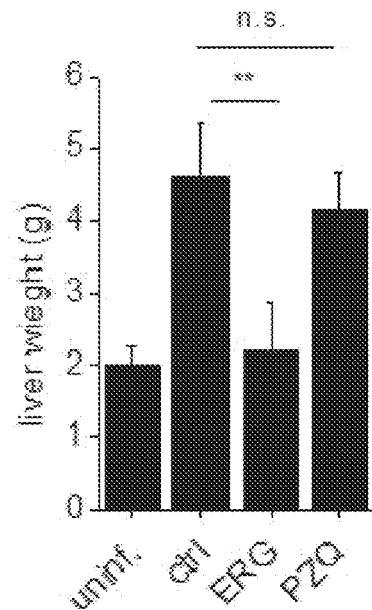
Figure 20L:
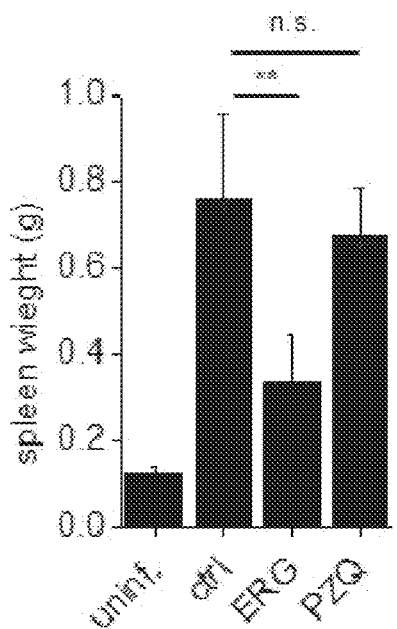

All animals were sacrificed 49 days post infection, and worms were harvested by dissection of the mesenteric vasculature, portal vein and liver. Ergotamine treatment significantly decreased worm burden relative to controls (65±10% reduction, p value=0.002, FIG. 20G), and while the drug reduced but did not eliminate parasite burden at the dosing regimen tested, it proved highly effective at blocking parasite egg production. Schistosomes lay large numbers of eggs within the host mesenteric system, and these progress through stages of development over approximately 5 days which can be scored looking at samples of the intestinal mucosa (Pellegrino et al., 1965). Therefore, it is possible to visually determine whether drug treatment has arrested parasite egg laying by observing a lack of developing eggs. Sections of both the large and small intestines were examined and eggs were manually counted and scored according to developmental stage (representative stages of embryo development shown in FIG. 20H-I, top). While the intestines of mice treated with vehicle control contained large numbers of eggs (average of 2722±1225 eggs per mouse), ergotamine and praziquantel treatment resulted in a 96% and 99% decrease in these counts (FIG. 20H-I), Finally, the liver and spleen enlargement that is characteristic of schistosomiasis was reduced in mice treated with ergotamine. The livers and spleens of infected animals treated with vehicle control were substantially larger than their uninfected littermates (FIG. 20J-L). However, infected mice that were treated with ergotamine exhibited no liver enlargement. While the livers of control infected mice increased 145±48% relative to uninfected littermates, livers of ergotamine treated mice showed a non-significant increase of just 15±34%. Splenomegaly was also reduced with ergotamine treatment. While the spleens of infected mice increased 504±176% relative to uninfected littermates, this was restricted to 151±80% in ergotamine treated animals. This effect is remarkable given that the current standard of care, praziquantel, provided no significant protection from liver and spleen enlargement (FIGS. 20J-L) and highlights the benefit of advancing Sm.5HTR ligands such as ergotamine as anthelmintics with a unique mechanism of action.

REFERENCES

Abdulla et al., *PLoS Neglected Tropical Diseases*, 3:e478 (2009).
Akerboom et al., *Front Mol. Neurosci.*, 6:2 (2013).
Anderson et al., *PLoS Neglected Tropical Diseases*, 9:e0004334 (2015).
Aragon et al., *Mol. Biochem. Parasitology*, 164:57 (2009).
Arunlakshana and Schild, *Br. J. Pharmacol. Chemother.* 14:48 (1959).
Berriman et al., *Nature*, 460:352 (2009).
Binkowski et al., *ACS Chem. Biol.*, 6:1193 (2011).
Bueding & Fisher, *J. Parasitol.*, 68:208 (1982).
Ruffle & Khayyall, *Nature*, 194:780 (1962).
Campos et al., *Parasit. Vectors*, 7:242 (2014).
Chan et al., *Parasitology Int'l.*, 62:619 (2013).
Chan et al., *PLoS Negl. Trop. Dis.*, 9:e0004063 (2015).
Chan et al., *PLoS Pathogens*, 10:e1003942 (2014).
Colley et al., *Lancet*, 383:2253 (2014).
Day et al., *Parasitology*, 108:425 (1994).
El-Shehabi et al., *PLoS Negl. Trop. Dis.*, 6:e1523 (2012).
Fan et al., *ACS Chem. Biol.*, 3:346 (2008).
Gilissen et al., *Biochemical Pharmacology*, 98:381 (2015).
Greenberg, *Parasitology*, 140:1534 (2013).
Harder et al., *Parasitology Research*, 73:442 (1987).
Hines-Kay et al., *Mol. Biochem. Parasitology*, 186:87 (2012).
Huang et al., *PLoS pathogens*, 8:e1002996 (2012).
Kasschau & Mansour, *Nature*, 296:66 (1982).
Kasschau and Mansour, *Molecular and Biochemical Parasitology*, 5:107 (1982).
Kenakin et al., *Drugs*, 40:666 (1990).
King et al., *PLoS Negl. Trop. Dis.*, 5:e1321 (2011).
Knight et al., *Molecular Pharmacology*, 75:374 (2009).
Kroeze et al., *Nat. Struct. Mol. Biol.*, 22:362 (2015).
Lovell et al., *Journal of Medicinal Chemistry*, 43:342 (2000).
MacDonald et al., *Molecular and Biochemical Parasitology*, 202:29 (2015).
Mansour, *Adv. Parasitol.*, 23:1 (1984).
Mansour, *Science*, 205:462 (1979).
Mehlhorn et al., *Arzneimittelforschung.*, 31:544 (1981).
Newmark and Sànchez-Alvarado, *Nature Rev. Genetics*, 3:210 (2002).
Ni and Miledi. *Proceedings of the National Academy of Sciences of the United States of America*, 94:2036 (1997).
Nichols et al., *Behav. Brain Res.*, 73:117 (1996).
Nogi et al., *PLoS Negl. Trop. Dis.*, 3:e464 (2009).
Olliaro et al., *J. Antimic. Chem.*, 69:863 (2014).
Overington et al., *Nat. Rev. Drug Discov.*, 5:993 (2006).
Patocka and Ribeiro, *Molecular and Biochemical Parasitology*, 187:32 (2013).
Patocka et al., *PLoS Pathogens*, 10:e1003878 (2014).
Pax et al., *Experimental Parasitology*, 58:312 (1984).
Pearce & Huang, *Cell Microbiol.*, 17:796 (2015).
Pellegrino & Faria, *Am. J. Trop. Med. Hyg.*, 14:363 (1965).
Pellegrino et al., *Z. Parasitenkd.*, 52:151 (1977).
Protasio et al., *PLoS Negl. Trop. Dis.*, 6:e1455 (2012).
Rahman et al., *Exp. Parasitol.*, 60:10 (1985).
Salvador-Recatala and Greenberg, *Wiley Interdiscip. Rev. Membr. Transp. Signal.*, 1:85 (2012).
Schiller et al., *J. Parasitol.*, 61:385 (1975).
Semeyn et al., *Journal of Parasitology*, 68:353 (1982).
Smith et al., *Molecular Pharmacology*, 70:1264 (2006).
Smith et al., *Molecular Pharmacology*, 79:318 (2011).
Tomosky et al., *Journal of Pharmacology and Experimental Therapeutics*, 190:260 (1974).
Tucker et al., *Curr. Protoc. Immunol.*, 103:Unit 19 11 (2013).
Wacker et al., *Cell.* 168:377 e312, doi:10.1016/j.cell.2016.12.033 (2017).
Wang and Mantsch, *Future Med. Chem.*, 4:177 (2012).
Wang et al., *Parasitology Res.*, 111:1871 (2012).
Willcockson and Hillman, *Comparative Biochemistry and Physiology C: Comparative Pharmacology*, 77:199 (1984).
Witchley et al., *Cell Reports*, 4:633 (2013).
Zamanian et al., *BMC Genomics*, 12:596 (2011).
Zhang et al., *J. Biomol. Screen.* 4:67 (1999).
Zhang et al., *Journal of Neuroscience*, 31:15983 (2011).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method of inhibiting or treating parasitic flatworm infection in a vertebrate, comprising:

administering an effective amount of a composition comprising one or more ergot alkaloids, one or more lysergic acid amides, or any combination thereof, wherein the ergot alkaloid is an agonist or partial agonist of *Schistosoma* serotonergic G-protein coupled receptor.

2. The method of claim 1 wherein the ergot alkaloid or the lysergic acid amide is an agonist or partial agonist of *Schistosoma mansoni* serotonergic G-protein coupled receptor (Sm.5HTR), *Schistosoma japonicum* serotonergic G-protein coupled receptor (Sj.5HTR) or *Schistosoma haematobium* serotonergic G-protein coupled receptor (Sh.5HTR), or any combination thereof.

3. The method of claim 1 wherein the ergot alkaloid comprises an ergopeptine.

4. The method of claim 1 wherein a combination of ergot alkaloids, a combination of lysergic acid amides, or a combination of at least one ergot alkaloid and at least one lysergic acid amide is administered.

5. The method of claim 1 wherein the vertebrate is a human or a non-human mammal.

6. The method of claim 1 wherein the amount inhibits contractility, viability, egg laying (number of eggs laid), or egg production by the flatworm or the amount is effective to reduce schistosomiasis, neurocystcicerosis or clonochiasis.

7. The method of claim 1 wherein the composition comprises a compound of formula (I):

wherein, $R^1$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^2$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^3$ is hydrogen, trifluoromethyl halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^4$ is hydrogen, trifluoromethyl, $C_{1-10}$ alkyl, $C_{2-10}$alkenyl, $C_{2-10}$ alkynyl, $C_{3-10}$ cycloalkyl aryl, or alkylaryl;

$R^5$ is hydrogen, trifluoromethyl halogen, cyano, nitro, $C_{1-10}$ alkyl, $C_{2-10}$ alkenyl, $C_{2-10}$ alkynyl, $C_{3-10}$cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond;

deuterated analogs thereof, or pharmaceutically acceptable salts thereof.

8. The method of claim 1 wherein the composition comprises a compound of formula (II):

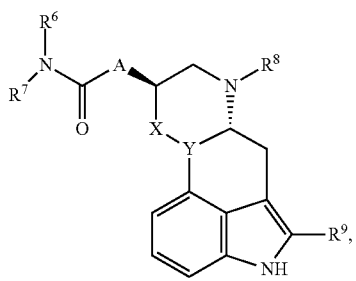

Formula (II)

wherein, $R^6$ is hydrogen, trifluoromethyl, $C_{1-10}$ alkyl, $C_{2-10}$ alkenyl, $C_{2-10}$ alkynyl, $C_{3-10}$ cycloalkyl, aryl, or alkylaryl;

$R^7$ is hydrogen, trifluoromethyl, $C_{1-10}$ alkyl, $C_{2-10}$ alkenyl, $C_{2-10}$ alkynyl, $C_{3-10}$ cycloalkyl aryl, or alkylaryl;

$R^8$ is hydrogen, trifluoromethyl, $C_{1-10}$ alkyl, $C_{2-10}$ alkenyl, $C_{2-10}$ alkynyl $C_{3-10}$ cycloalkyl, aryl, or alkylaryl;

$R^9$ is hydrogen, trifluoromethyl, halogen, cyano, nitro, $C_{1-10}$ alkyl, $C_{2-10}$ alkenyl, $C_{2-10}$ alkynyl, $C_{3-10}$ cycloalkyl, aryl, alkylaryl, $OR^x$, $OCOR^x$, $ONR^xR^y$, $SR^x$, $NR^xR^y$, $NR^xOR^y$, $NR^xNR^xR^y$, $NR^xCOR^y$, $NR^xCO_2R^y$, $NR^xSO_2R^y$, $COR^x$, or $CO_2R^x$;

$R^x$ and $R^y$ are independently at each occurrence hydrogen, $C_{1-10}$ alkyl, $C_{2-10}$ alkenyl, $C_{2-10}$ alkynyl, $C_{3-10}$ cycloalkyl, aryl, or alkylaryl;

X—Y is a carbon-carbon single bond or a carbon-carbon double bond;

A is a bond or $NR^x$;

deuterated analogs thereof, or pharmaceutically acceptable salts thereof.

9. The method of claim 1 wherein the compound is administered weekly.

10. The method of claim 1 wherein the vertebrate is further administered caffeine or praziquantel.

11. The method of claim 1 wherein the composition is orally, intramuscularly, rectally, intravenously or intranasally administered.

12. The method of claim 1 wherein composition is a tablet or animal feed.

13. The method of claim 1 wherein the vertebrate is a human and the parasitic worm or helminth selected from the group consisting of Roundworm, Whipworm, Hookworm, *Ascaris, Pinworm, Strongyloides*, Schistosome, and Trematodes.

14. The method of claim 1 wherein the worm is *S. masoni, S. haemutobium, S. japanicum, S. mekongi* or *S. intercalatum*.

15. The method of claim 1 wherein the worm or helminth is resistant to praziquantel.

16. The method of claim 1 wherein ergotamine, dihydroergotamine and lisuride are administered.

17. The method of claim 16 wherein ergotamine, dihydroergotamine and lisuride are concurrently administered.

18. The method of claim 1 wherein parasitic flatworm infection is inhibited or treated.

19. The method of claim 7 wherein $R^3$ is OH and $R^4$ is $C_{1-10}$ alkyl.

20. The method of claim 8 wherein $R^8$ is $C_{1-10}$ alkyl.

* * * * *